United States Patent
Meng et al.

(10) Patent No.: US 10,857,121 B2
(45) Date of Patent: Dec. 8, 2020

(54) USE OF MALONONITRILE COMPOUNDS FOR PROTECTING ANIMALS FROM PARASITES

(71) Applicants: MERIAL INC., Duluth, GA (US); BASF, SE, Ludwigshafen (DE)

(72) Inventors: Charles Meng, Grayson, GA (US); Christian Miculka, Wiesbaden (DE); Mark Soll, Alpharetta, GA (US); Ralph Paulini, Bad Durkheim (DE); Matthias Pohlman, Freinsheim (DE); Sebastian Sorgel, Ludwigshafen (DE); Henricus Maria Martinus Bastiaans, Chapel Hill, NC (US); Sarah Rachel Devereux, Raleigh, NC (US); Cecille Ebuenga Doyog, Puthotuntungin los Banos (PH); Anna Malveda Umali, Lusacan Tiaong Quezo (PH); Rhoel Suiza Cosare, Calauan Laguna Brgy. Sto. Tomas (PH); Christopher Palmer, San Jose, CA (US); Takeo Hokama, Mountain View, CA (US)

(73) Assignees: MERIAL INC., Duluth, GA (US); BASF, SE, Ludwigshafen (DE)

( * ) Notice: Subject to any disclaimer, the term of this patent is extended or adjusted under 35 U.S.C. 154(b) by 15 days.

(21) Appl. No.: 15/304,018

(22) PCT Filed: Apr. 17, 2015

(86) PCT No.: PCT/US2015/026424
§ 371 (c)(1),
(2) Date: Oct. 13, 2016

(87) PCT Pub. No.: WO2015/161224
PCT Pub. Date: Oct. 22, 2015

(65) Prior Publication Data
US 2017/0027899 A1    Feb. 2, 2017

Related U.S. Application Data

(60) Provisional application No. 61/980,832, filed on Apr. 17, 2014.

(51) Int. Cl.
*A61K 31/277*  (2006.01)
*A01N 37/34*   (2006.01)
*A01K 11/00*   (2006.01)
*A61D 7/00*    (2006.01)
*A61K 9/00*    (2006.01)
*A61K 31/357*  (2006.01)

(52) U.S. Cl.
CPC .......... *A61K 31/277* (2013.01); *A01K 11/001* (2013.01); *A01N 37/34* (2013.01); *A61D 7/00* (2013.01); *A61K 9/0046* (2013.01); *A61K 31/357* (2013.01)

(58) Field of Classification Search
USPC ........................................................ 514/467
See application file for complete search history.

(56) References Cited

U.S. PATENT DOCUMENTS

| | | | |
|---|---|---|---|
| 6,955,818 B1 * | 10/2005 | Hacket ................... | A01N 25/02 119/600 |
| 2015/0282481 A1 * | 10/2015 | Paulini ................... | A01N 37/34 504/100 |

FOREIGN PATENT DOCUMENTS

| | | |
|---|---|---|
| WO | 02/090321 A1 | 11/2002 |
| WO | 2014/064093 A1 | 5/2014 |
| WO | 2014/090700 A1 | 6/2014 |
| WO | 2015/158603 A1 | 10/2015 |

OTHER PUBLICATIONS

"Horn Flies on Cattle: Biology and Management", G. Johnson et al., A Self-Learning Resource from Montana State University, May 1, 2009, pp. 1-4, XP055200465, Retrieved from the Internet: URL:http://store. msuextension.org/publications/AgandNaturalResources/MT200912AG.pdf.
"External Parasites on Beef Cattle", P.E. Kaufman et al., Mar. 1, 2009, pp. 1-24, XP055200466, Retrieved from the Internet: URL:http://web.archive.org/web/20091116205911 /http://edis.ifas.utl.edu/pdffiles/IG/IG13000.pdf [retrieved on Jul. 6, 2015].

* cited by examiner

*Primary Examiner* — Marcos L Sznaidman
(74) *Attorney, Agent, or Firm* — John Ezcurra; Judy Jarecki-Black

(57) ABSTRACT

The present invention provides uses of aryl alkyl malononitrile compounds of formula (I), or veterinarily acceptable salts thereof, for controlling and preventing parasite infestations in animals. The invention also provides methods for controlling and preventing parasite infestation in animals comprising administering an effective amount of at least one aryl alkyl malononitrile compound of formulae (I), or a veterinarily acceptable salt thereof, to the animal.

12 Claims, No Drawings

USE OF MALONONITRILE COMPOUNDS FOR PROTECTING ANIMALS FROM PARASITES

JOINT RESEARCH AGREEMENT

The present application is the subject of a joint research agreement, according to 35 U.S.C. 102(c)(2), between Merial, Inc. and BASF SE which agreement was in effect before the filing date of the present application.

FIELD OF THE INVENTION

The present invention is directed to the use of new aryl alkyl malononitrile compounds with insecticidal and parasiticidal activity and compositions comprising the compounds to protect animals against parasites. The present invention also provides methods for eradicating, controlling, and preventing a parasite infestation and infection in or on animals. The compounds of the invention, or salts thereof, may be administered to animals, particularly mammals, to prevent or treat parasitic infestations and infections.

CROSS REFERENCE TO RELATED APPLICATIONS

This application claims the benefit of priority to U.S. Provisional Application No. 61/980,832 filed Apr. 17, 2014, which is incorporated herein by reference in its entirety.

BACKGROUND OF THE INVENTION

Animals including mammals and birds are often susceptible to parasite infestations/infections. These parasites may be ectoparasites or endoparasites. Domesticated animals, such as cats and dogs, are often infested with one or more of the following ectoparasites:

fleas (e.g. *Ctenocephalides* spp., such as *Ctenocephalides fells* and the like);
ticks (e.g. *Rhipicephalus* spp., *Ixodes* spp., *Dermacentor* spp., *Amblyoma* spp., *Haemaphysalis* spp., and the like);
mites (e.g. *Demodex* spp., *Sarcoptes* spp., *Otodectes* spp., *Cheyletiella* spp., and the like);
lice (e.g. *Trichodectes* spp., *Felicola* spp., *Linognathus* spp., and the like);
mosquitoes (*Aedes* spp., *Culex* spp., *Anopheles* spp. and the like); and
flies (*Musca* spp., *Stomoxys* spp., *Dermatobia* spp., and the like).

Fleas are a problem because not only do they adversely affect the health of the animal or human, but they also cause a great deal of psychological stress. Moreover, fleas may also transmit pathogenic agents to animals and humans, such as tapeworm (*Dipyhdium caninum*).

Similarly, ticks are also harmful to the physical and/or psychological health of the animal or human. However, the most serious problem associated with ticks is that they are vectors of pathogenic agents affecting both humans and animals. Major diseases which may be transmitted by ticks include borreliosis (Lyme disease caused by *Borrelia burgdorferi*), babesiosis (or piroplasmosis caused by *Babesia* spp.) and rickettsioses (e.g. Rocky Mountain spotted fever). Ticks also release toxins which cause inflammation or paralysis in the host. Occasionally, these toxins may be fatal to the host.

Animals and humans also suffer from endoparasitic infections caused by parasitic worms categorized as cestodes (tapeworms), nematodes (roundworms) and trematodes (flatworms or flukes). These parasites cause a variety of pathologic conditions in domestic animals including dogs, cats, pigs, sheep, horses, cattle and poultry. Nematode parasites which occur in the gastrointestinal tract of animals and humans include those of the genera *Ancylostoma, Necator, Ascaris, Strongyloides, Trichinella, Capillaria, Toxocara, Toxascaris, Trichuris, Enterobius, Haemonchus, Trichostrongylus, Ostertagia, Cooperia, Oesophagostomum, Bunostomum, Strongylus, Cyathostomum,* and *Parascaris* among others, and those that are found in the blood vessels or other tissues and organs include *Onchocerca, Dirofilaria, Wuchereria* and the extra intestinal stages of *Strongyloides, Toxocara* and *Trichinella*. Therapeutic agents are administered to animals by a variety of routes. These routes include, for example, oral ingestion, topical application or parenteral administration. The particular route selected by the practitioner depends upon factors such as the physicochemical properties of the pharmaceutical or therapeutic agent, the condition of the host and economics.

Pesticidal compounds having a dicyanoalkane moiety have been disclosed in a number of patent applications, e.g. JP 2002 284608, WO 02/089579, WO 02/090320, WO 02/090321, WO 04/006677, WO 04/020399, JP 2004 99593, JP 2004 99597, WO 05/068432, WO 05/064823, EP 1555259, WO 05/063694, WO 2007/071609, and WO 2007/147888.

It has now been found that particular aryl alkyl malononitriles of formula (I) bearing an additional carbocyclic ring on the alkyl group are particularly useful for treating and protecting animals from parasites.

It is expressly noted that citation or identification of any document in this application is not an admission that such document is available as prior art to the present invention. Any foregoing applications, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

SUMMARY OF THE INVENTION

The invention provides novel and inventive uses of aryl alkyl malononitrile compounds with parasiticidal and insecticidal activity to treat and protect animals from parasites. The invention also provides methods for the treatment and prevention of parasitic infestations and/or infections of animals comprising administration of one or more of the aryl alkyl malononitrile compounds, or a salt thereof, described herein to an animal.

Thus, in one embodiment, the invention provides a method for controlling or preventing the parasitic infestation of an animal by ectoparasites. In one embodiment, the invention provides a method for controlling or preventing a parasitic infestation by *Haematobia irritans* or *Stomoxys calcitrans* flies comprising administering an effective amount of an aryl alkyl malononitrile compound of formula (I), or a salt thereof, to the animal:

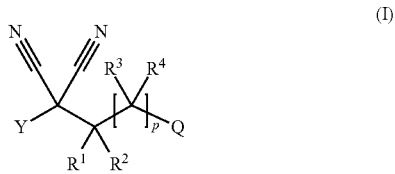

(I)

wherein variables Y, $R^1$, $R^2$, $R^3$, $R^4$, p and Q are as defined below. In another embodiment, the invention provides a method for controlling or preventing a parasitic infestation in animals by lice, mites or ticks comprising administering an effective amount of an aryl alkyl malononitrile compound of formula (I), or a salt thereof to the animal.

It is an object of the invention to not encompass within the invention any previously known product, process of making the product, or method of using the product such that the Applicants reserve the right to this invention and hereby disclose a disclaimer of any previously known product, process, or method.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. Patent law; e.g., they allow for elements not explicitly recited, but exclude elements that are found in the prior art or that affect a basic or novel characteristic of the invention.

These and other embodiments are disclosed or are obvious from, and encompassed by, the following Detailed Description.

DETAILED DESCRIPTION

The present invention provides novel and inventive uses of aryl alkyl malononitrile compounds of formula (I) with insecticidal and parasiticidal activity, or veterinarily acceptable salts thereof, and compositions comprising the compounds or salts thereof, for the treatment or prevention of parasitic infestations in an animal. Also provided are methods for the treatment or prevention of parasitic infestations in animals, comprising administering an effective amount of at least one compound of the invention, or a salt thereof, or compositions comprising the compounds or salts thereof, to the animal.

The compounds of formula (I) described herein and their veterinarily acceptable salts are particularly effective for controlling arthropod pests such as arachnids, myriapods and insects. In other embodiments, the compounds of formula (I) described herein are effective for controlling lice, mites and ticks. Ectoparasites that are particularly well controlled by the compounds of the invention include various species of parasitic flies, and in particular *Stomoxys calcitrans* (stable fly) and *Haematobia irritans* (horn fly). These parasitic flies present a serious problem to the health and wellbeing of many animals, and particularly livestock animals, if left uncontrolled. Therefore, the inventive compounds of formulae (I), veterinarily acceptable salts thereof, and compositions comprising the compounds and salts thereof, have substantial utility in controlling and preventing the infestation of animals by ectoparasites including lice, mites, ticks and parasitic flies.

The invention includes at least the following features:

(a) methods for treating a parasitic infestation by lice, mites, ticks and parasitic flies on an animal are provided, which methods comprise administering a parasiticidally effective amount of a compound of formula (I), or veterinarily acceptable salts thereof, or a composition comprising the compounds or salts to the animal in need thereof;

(b) methods for the prevention of a parasitic infestation by lice, mites, ticks and parasitic flies on an animal, which comprise administering a parasiticidally effective amount of a compound of formula (I), or veterinarily acceptable salts thereof, or a composition comprising the compounds or salts to the animal in need thereof;

(c) the use of the compounds of aryl alkyl malononitrile compounds formula (I), or veterinarily acceptable salts thereof, for controlling lice, mites, ticks and parasitic flies, on an animal; and (d) the use of the compounds of the aryl alkyl malononitrile compounds formula (I), or veterinarily acceptable salts thereof, in the manufacture of a veterinary medicament for controlling lice, mites, ticks and parasitic flies on animals.

Definitions

Terms used herein will have their customary meanings in the art unless specified. The organic moieties mentioned in the definitions of the variables of formula (I) are like the term halogen i.e., collective terms for individual listings of the individual group members. The prefix $C_n$-$C_m$ indicates in each case the possible number of carbon atoms in the group.

The term "halogen" as used herein refers to fluoro, chloro, bromo and iodo.

The term "partially or fully halogenated" as used herein means that 1 or more, e.g. 1, 2, 3, 4 or 5 or all of the hydrogen atoms of a given radical have been replaced by a halogen atom, in particular by fluorine or chlorine.

The term "$C_n$-$C_m$-alkyl" as used herein (and also in $C_n$-$C_m$-alkylamino, di-$C_n$-$C_m$-alkylamino, $C_n$-$C_m$-alkylaminocarbonyl, di-($C_n$-$C_m$-alkylamino)carbonyl, $C_n$-$C_m$-alkylthio, $C_n$-$C_m$-alkylsulfinyl and $C_n$-$C_m$-alkylsulfonyl) refers to a branched or unbranched saturated hydrocarbon group having n to m, e.g. 1 to 10 carbon atoms, preferably 1 to 6 carbon atoms, for example methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

The term "$C_n$-$C_m$-haloalkyl" as used herein (and also in $C_n$-$C_m$-haloalkylsulfinyl and $C_n$-$C_m$-haloalkylsulfonyl) refers to a straight-chain or branched alkyl group having n to m carbon atoms, e.g. 1 to 10, in particular 1 to 6 carbon atoms (as mentioned above), where some or all of the hydrogen atoms in these groups may be replaced by halogen atoms as mentioned above, for example $C_1$-$C_4$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like. The term $C_1$-$C_{10}$-haloalkyl in particular comprises $C_1$-$C_2$-fluoroalkyl, which is synonym with methyl or ethyl, wherein 1, 2, 3, 4 or 5 hydrogen atoms are substituted by fluorine atoms, such as fluoromethyl, difluoromethyl, trifluoromethyl, fluoroethyl, 2-fluoroethyl, 2,2-difluoroethyl, 2,2,2-trifluoroethyl and pentafluoromethyl.

Similarly, the terms "$C_n$-$C_m$-alkoxy" and "$C_n$-$C_m$-alkylthio" (or the term "$C_n$-$C_m$-alkylsulfenyl", respectively) refer to straight-chain or branched alkyl groups having n to m carbon atoms, e.g. 1 to 10, in particular 1 to 6 or 1 to 4 carbon atoms (as mentioned above) bonded through oxygen or sulfur linkages, respectively, at any bond in the alkyl group. Examples include $C_1$-$C_4$-alkoxy such as methoxy, ethoxy, propoxy, isopropoxy, butoxy, sec-butoxy, isobutoxy and tert-butoxy, further $C_1$-$C_4$-alkylthio such as methylthio, ethylthio, propylthio, isopropylthio, and n-butylthio.

Accordingly, the terms "$C_n$-$C_m$-haloalkoxy" and "$C_n$-$C_m$-haloalkylthio" (or the term "$C_n$-$C_m$-haloalkylsulfenyl", respectively) refer to straight-chain or branched alkyl groups having n to m carbon atoms, e.g. 1 to 10, in particular 1 to 6 or 1 to 4 carbon atoms (as mentioned above) bonded through oxygen or sulfur linkages, respectively, at any bond in the alkyl group, where some or all of the hydrogen atoms in these groups may be replaced by halogen atoms as mentioned above, for example $C_1$-$C_2$-haloalkoxy, such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy and pentafluoroethoxy, further $C_1$-$C_2$-haloalkylthio, such as chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio and pentafluoroethylthio and the like. Similarly the terms "$C_1$-$C_2$-fluoroalkoxy" and "$C_1$-$C_2$-fluoroalkylthio" refer to $C_1$-$C_2$-fluoroalkyl which is bound to the remainder of the molecule via an oxygen atom or a sulfur atom, respectively.

The term "$C_2$-$C_m$-alkenyl" as used herein refers to a branched or unbranched unsaturated hydrocarbon group having 2 to m, e.g. 2 to 10 or 2 to 6 carbon atoms and a double bond in any position, such as ethenyl, 1-propenyl, 2-propenyl, 1-methyl-ethenyl, 1-butenyl, 2-butenyl, 3-butenyl, 1-methyl-1-propenyl, 2-methyl-1-prop enyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

The term "$C_2$-$C_m$-alkynyl" as used herein refers to a branched or unbranched unsaturated hydrocarbon group having 2 to m, e.g. 2 to 10 or 2 to 6 carbon atoms and containing at least one triple bond, such as ethynyl, propynyl, 1-butynyl, 2-butynyl and the like.

The term "$C_1$-$C_4$-alkoxy-$C_1$-$C_4$-alkyl" as used herein refers to alkyl having 1 to 4 carbon atoms, e.g. like specific examples mentioned above, wherein one hydrogen atom of the alkyl radical is replaced by an $C_1$-$C_4$-alkoxy group.

The term "$C_3$-$C_m$-cycloalkyl" as used herein refers to a monocyclic 3- to m-membered saturated cycloaliphatic radicals, e.g. cyclopropyl, cyclobutyl, cyclopentyl, cyclohexyl, cycloheptyl, cyclooctyl and cyclodecyl.

The term "aryl" as used herein refers to an aromatic hydrocarbon radical such as naphthyl or in particular phenyl.

The term "naphthyl" as used herein refers to 1-naphthyl and 2-naphthyl.

The term "3- to 6-membered carbocyclic ring" as used herein refers to cyclopropane, cyclobutane, cyclopentane and cyclohexane rings.

The term "3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$," as used herein refers to monocyclic radicals, the monocyclic radicals being saturated, partially unsaturated or aromatic. The heterocyclic radical may be attached to the remainder of the molecule via a carbon ring member or via a nitrogen ring member.

Examples of 3-, 4-, 5-, 6- or 7-membered saturated heterocyclyl include: oxiranyl, aziridinyl, azetidinyl, 2 tetrahydrofuranyl, 3-tetrahydrofuranyl, 2 tetrahydrothienyl, 3 tetrahydrothienyl, 2-pyrrolidinyl, 3-pyrrolidinyl, 3 pyrazolidinyl, 4 pyrazolidinyl, 5-pyrazolidinyl, 2 imidazolidinyl, 4 imidazolidinyl, 2-oxazolidinyl, 4-oxazolidinyl, 5 oxazolidinyl, 3-isoxazolidinyl, 4 isoxazolidinyl, 5 isoxazolidinyl, 2 thiazolidinyl, 4-thiazolidinyl, 5-thiazolidinyl, 3 isothiazolidinyl, 4-isothiazolidinyl, 5 isothiazolidinyl, 1,2,4-oxadiazolidin-3-yl, 1,2,4 oxadiazolidin 5 yl, 1,2,4-thiadiazolidin-3-yl, 1,2,4 thiadiazolidin-5-yl, 1,2,4 triazolidin-3-yl, 1,3,4-oxadiazolidin-2-yl, 1,3,4 thiadiazolidin-2-yl, 1,3,4 triazolidin-2-yl, 2-tetrahydropyranyl, 4 tetrahydropyranyl, 1,3-dioxan-5-yl, 1,4-dioxan-2-yl, 2-piperidinyl, 3-piperidinyl, 4-piperidinyl, 3-hexahydropyridazinyl, 4 hexahydropyridazinyl, 2-hexahydropyrimidinyl, 4-hexahydropyrimidinyl, 5 hexahydropyrimidinyl, 2-piperazinyl, 1,3,5-hexahydrotriazin-2-yl and 1,2,4 hexahydrotriazin-3-yl, 2-morpholinyl, 3-morpholinyl, 2-thiomorpholinyl, 3-thiomorpholinyl, 1-oxothiomorpholin-2-yl, 1-oxothiomorpholin-3-yl, 1,1-dioxothiomorpholin-2-yl, 1,1-dioxothiomorpholin-3-yl, hexahydroazepin-1-, -2-, -3- or -4-yl, hexahydrooxepinyl, hexahydro-1,3-diazepinyl, hexahydro-1,4-diazepinyl, hexahydro-1,3-oxazepinyl, hexahydro-1,4-oxazepinyl, hexahydro-1,3-dioxepinyl, hexahydro-1,4-dioxepinyl and the like.

Examples of 3-, 4-, 5-, 6- or 7-membered partially unsaturated heterocyclyl include:

2,3-dihydrofur-2-yl, 2,3-dihydrofur-3-yl, 2,4-dihydrofur-2-yl, 2,4-dihydrofur-3-yl, 2,3-dihydrothien-2-yl, 2,3 dihydrothien-3-yl, 2,4 dihydrothien-2-yl, 2,4-dihydrothien-3-yl, 2-pyrrolin-2-yl, 2-pyrrolin-3-yl, 3 pyrrolin-2-yl, 3-pyrrolin-3-yl, 2-isoxazolin-3-yl, 3-isoxazolin-3-yl, 4 isoxazolin 3 yl, 2-isoxazolin-4-yl, 3-isoxazolin-4-yl, 4-isoxazolin-4-yl, 2 isoxazolin-5-yl, 3-isoxazolin-5-yl, 4-isoxazolin-5-yl, 2-isothiazolin-3-yl, 3 isothiazolin-3-yl, 4-isothiazolin-3-yl, 2-isothiazolin-4-yl, 3-isothiazolin-4-yl, 4 isothiazolin-4-yl, 2-isothiazolin-5-yl, 3-isothiazolin-5-yl, 4-isothiazolin-5-yl, 2,3 dihydropyrazol-1-yl, 2,3-dihydropyrazol-2-yl, 2,3-dihydropyrazol-3-yl, 2,3 dihydropyrazol-4-yl, 2,3-dihydropyrazol-5-yl, 3,4-dihydropyrazol-1-yl, 3,4 dihydropyrazol-3-yl, 3,4-dihydropyrazol-4-yl, 3,4-dihydropyrazol-5-yl, 4,5 dihydropyrazol-1-yl, 4,5-dihydropyrazol-3-yl, 4,5-dihydropyrazol-4-yl, 4,5 dihydropyrazol-5-yl, 2,3-dihydrooxazol-2-yl, 2,3-dihydrooxazol-3-yl, 2,3 dihydrooxazol-4-yl, 2,3-dihydrooxazol-5-yl, 3,4-dihydrooxazol-2-yl, 3,4 dihydrooxazol-3-yl, 3,4-dihydrooxazol-4-yl, 3,4-dihydrooxazol-5-yl, 3,4 dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4 di- or tetrahydropyridazinyl, 2-di- or tetrahydropyrimidinyl, 4-di- or tetrahydropyrimidinyl, 5 di- or tetrahydropyrimidinyl, di- or tetrahydropyrazinyl, 1,3,5-di- or tetrahydrotriazin-2-yl, 1,2, 4-di- or tetrahydrotriazin-3-yl, 2,3,4,5-tetrahydro[1H]azepin-1-, -2-3-, -4-, -5-, -6- or -7-yl, 3,4,5,6-tetrahydro[2H]azepin-2-, -3-, -4-, -5-, -6- or -7-yl, 2,3,4,7 tetrahydro[1H]azepin-1-, -2-, -3-, -4-, -5-, -6- or -7-yl, 2,3,6,7 tetrahydro[1H]azepin-1-, -2-, -3-, -4-, -5-, -6- or -7-yl, tetrahydrooxepinyl, such as 2,3,4,5-tetrahydro[1H]oxepin-2-, -3-, -4-, -5-, -6- or -7-yl, 2,3,4,7 tetrahydro[1H]oxepin-2-, -3-, -4-, -5-, -6- or -7-yl, 2,3,6,7 tetrahydro[1H]oxepin-2-, -3-, -4-, -5-, -6- or -7-yl, tetrahydro-1,3-diazepinyl, tetrahydro-1,4-diazepinyl, tetrahydro-1,3-oxazepinyl, tetrahydro-1,4-oxazepinyl, tetrahydro-1,3-dioxepinyl and tetrahydro-1,4-dioxepinyl.

3-, 4-, 5-, 6- or 7-membered aromatic heterocyclyl is 5- or 6-membered aromatic heterocyclyl (hetaryl). Examples are: 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 2-thiazolyl, 4 thiazolyl, 5-thiazolyl, 2-imidazolyl, 4-imidazolyl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl and 2-pyrazinyl.

The term "$C_2$-$C_7$-alkylene" as used herein refers to a divalent branched or preferably unbranched saturated aliphatic chain having 2 to 7 carbon atoms, for example $CH_2CH_2$, —$CH(CH_3)$—, $CH_2CH_2CH_2$, $CH(CH_3)CH_2$, $CH_2CH(CH_3)$, $CH_2CH_2CH_2CH_2$, $CH_2CH_2CH_2CH_2CH_2$, $CH_2CH_2CH_2CH_2CH_2CH_2$ and $CH_2CH_2CH_2CH_2CH_2CH_2CH_2$.

The term "tri-($C_1$-$C_4$)silyl-$C_2$-$C_4$-alkynyl" as used herein refers to $C_2$-$C_4$-alkynyl substituted with tri-($C_1$-$C_4$)silyl. The term "(trimethylsilyl)ethynyl" as used herein refers to ethynyl substituted with trimethylsilyl.

The term "$C_1$-$C_6$-alkyl-$C_3$-$C_8$-cycloalkyl" as used herein refers to $C_3$-$C_8$-cycloalkyl substituted with $C_1$-$C_6$-alkyl. The term "$C_1$-$C_4$-alkyl-$C_3$-$C_6$-cycloalkyl" as used herein refers to $C_3$-$C_6$-cycloalkyl substituted with $C_1$-$C_4$-alkyl.

The term "phenyl unsubstituted or substituted with 1, 2, 3, 4 or 5 substituents $R^5$/$R^6$" means "phenyl unsubstituted or substituted with up to 3 or in the case of halogen up to the maximum possible number of substituents $R^5$/$R^6$". This phrase also means "phenyl unsubstituted or substituted with 1, 2, 3 or 4 substituents $R^5$/$R^6$"; "phenyl unsubstituted or substituted with 1, 2 or 3 substituents $R^5$/$R^6$"; "phenyl unsubstituted or substituted with 1 or 2 substituents $R^5$/$R^6$", and also "phenyl unsubstituted or substituted with 1 substituent $R^5$/$R^6$".

Preferably, the term "naphthyl unsubstituted or substituted with 1, 2, 3, 4, 5, 6 or 7 substituents $R^5$" means "naphthyl unsubstituted or substituted with up to 3 or in the case of halogen up to the maximum possible number of substituents $R^5$", more preferably "naphthyl unsubstituted or substituted with up to 3 substituents $R^5$", even more preferably "naphthyl unsubstituted or substituted with up to 2 substituents $R^5$", and particularly preferably "naphthyl unsubstituted or substituted with up to 1 substituent $R^5$".

Preferably, the term "unsubstituted or substituted with up to 5 $R^c$/$R^d$/$R^E$, e.g. in connection with phenyl or a heterocyclic ring, means "unsubstituted or substituted with up to 3 or in the case of halogen up to the maximum possible number of $R^c$/$R^d$/$R^E$", more preferably "unsubstituted or substituted with up to 2 or in the case of halogen up to the maximum possible number of $R^c$/$R^d$/$R^E$", also more preferably "unsubstituted or substituted with up to 3 $R^c$/$R^d$/$R^E$", and even more preferably "unsubstituted or substituted with up to 2 $R^c$/$R^d$/$R^E$".

Preferably, the term "unsubstituted or substituted with one or more", e.g. in connection with substituents $R^6$, $R^a$, $R^b$ or $R^M$, means "unsubstituted or substituted with up to 5 or in the case of halogen up to the maximum possible number of", more preferably "unsubstituted or substituted with up to 3 or in the case of halogen up to the maximum possible number of", even more preferably "unsubstituted or substituted with up to 2 or in the case of halogen up to the maximum possible number of", also more preferably "unsubstituted or substituted with up to 5", also even more preferably "unsubstituted or substituted with up to 3", and particularly preferably "unsubstituted or substituted with up to 2".

The expression "effective amount" as used herein means a sufficient amount of a compound or composition of the invention to eradicate or reduce the number of parasites infesting the animal. In some embodiments, an effective amount of the active agent achieves at least about 50%, at least about 60% or at least about 70% efficacy against the target parasite. In other embodiments, an effective amount of the active agent achieves at least about 80%, or at least about 90% efficacy against the target parasites.

Accordingly, in one aspect the invention provides the use of a compound of formula (I) and a method for controlling parasites comprising administering an effective amount of a compound of formula (I),

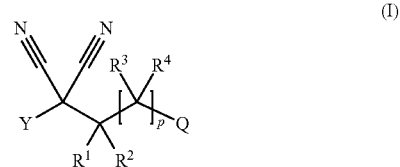

(I)

or a salt thereof, or a composition comprising the compound or salt, for treating and/or protecting an animal from parasites, wherein Y is phenyl unsubstituted or substituted with 1, 2, 3, 4 or 5 substituents $R^5$; or naphthyl unsubstituted or substituted with 1, 2, 3, 4, 5, 6 or 7 substituents $R^5$;

Q is phenyl unsubstituted or substituted with 1, 2, 3, 4 or 5 substituents $R^6$; $C_3$-$C_8$ cycloalkyl unsubstituted or substituted with one or more substituents $R^6$; or $C_3$-$C_8$ cycloalkenyl unsubstituted or substituted with one or more substituents $R^6$;

$R^1$ is hydrogen, halogen, cyano, hydroxy, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, $C_1$-$C_6$-alkoxy, $C_2$-$C_6$-alkenyloxy, $C_1$-$C_6$-alkylthio, ($C_1$-$C_6$-alkoxy)carbonyl, wherein the carbon atoms of the aforementioned aliphatic or cycloaliphatic radicals are unsubstituted or substituted with 1, 2 or 3 substituents $R^7$;

$R^2$ is hydrogen or halogen;

or $R^1$ and $R^2$ form together with the carbon atom to which they are attached a methylene group or a cyclopropyl group;

$R^3$ is hydrogen, halogen, cyano, hydroxy, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, $C_1$-$C_6$-alkoxy, $C_2$-$C_6$-alkenyloxy, $C_1$-$C_6$-alkylthio, ($C_1$-$C_6$-alkoxy)carbonyl, wherein the carbon atoms of the aforementioned aliphatic or cycloaliphatic radicals are unsubstituted or substituted with 1, 2 or 3 substituents $R^7$;

$R^4$ is hydrogen or halogen;

or $R^3$ and $R^4$ form together with the carbon atom to which they are attached a methylene group or a cyclopropyl group;

each $R^5$, $R^6$ is independently halogen, cyano, azido, nitro, —SCN, $SF_5$, $C_1$-$C_6$ alkyl, $C_2$-$C_6$ alkenyl, $C_2$-$C_6$ alkynyl, wherein the carbon atoms of the aforementioned aliphatic radicals are unsubstituted or substituted with one or more $R^d$;

$C_3$-$C_8$ cycloalkyl or $C_3$-$C_8$ cycloalkenyl, wherein the carbon atoms of the aforementioned cycloaliphatic radicals are unsubstituted or substituted with one or more $R^b$;

phenyl unsubstituted or substituted with up to 5 $R^c$;

a 3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$, wherein the aforementioned ring is unsubstituted or substituted with up to 5 $R^d$;

$Si(R^e)_3$, $OR^f$, $SR^f$, $OS(O)_xR^h$, $S(O)_xR^h$, $N(R^i)_2$, $N(R^i)C(=O)R^m$, $OC(=O)R^m$, $C(=O)R^m$, $C(=O)OR^f$, $C(=NR^i)R^m$, $C(=S)R^m$;

or two $R^5$ on two adjacent carbon atoms present on one phenyl ring are together a bridge selected from $CH_2CH_2CH_2CH_2$, N=CH—CH=CH, CH=N—CH=CH, N=CH—N=CH, N=CH—CH=N, $OCH_2CH_2CH_2$, OCH=$CHCH_2$, $CH_2OCH_2CH_2$, $OCH_2CH_2O$, $OCH_2OCH_2$, $CH_2CH_2CH_2$, CH=$CHCH_2$, $CH_2CH_2O$, CH=CHO, $CH_2OCH_2$, $CH_2C(=O)O$, $C(=O)OCH_2$, $O(CH_2)O$, $SCH_2CH_2CH_2$, SCH=$CHCH_2$, $CH_2SCH_2CH_2$, $SCH_2CH_2S$, $SCH_2SCH_2$, $CH_2CH_2S$, CH=CHS, $CH_2SCH_2$, $CH_2C(=S)S$, $C(=S)SCH_2$, $S(CH_2)S$, $CH_2CH_2NR^K$, $CH_2CH$=N, CH=CH—$NR^K$, OCH=N, SCH=N and form together with the carbon atoms the two $R^5$ are bonded to a 5- or 6-membered partially unsaturated or aromatic carbocyclic or heterocyclic ring, wherein the ring is unsubstituted or substituted with 1 or 2 substituents selected from =O, OH, $CH_3$, $OCH_3$, halogen, halomethyl and halomethoxy; preferably are together a bridge selected from $CH_2CH_2CH_2CH_2$, N=CH—CH=CH, CH=N—CH=CH, N=CH—N=CH, $OCH_2CH_2CH_2$, OCH=$CHCH_2$, $CH_2OCH_2CH_2$, $OCH_2CH_2O$, $OCH_2OCH_2$, $CH_2CH_2CH_2$, CH=$CHCH_2$, $CH_2CH_2O$, CH=CHO, $CH_2OCH_2$, $CH_2C(=O)O$, $C(=O)OCH_2$, $O(CH_2)O$, $SCH_2CH_2CH_2$, SCH=$CHCH_2$, $CH_2SCH_2CH_2$, $SCH_2CH_2S$, $SCH_2SCH_2$, $CH_2CH_2S$, CH=CHS, $CH_2SCH_2$, $CH_2C(=S)S$, $C(=S)SCH_2$, $S(CH_2)S$, $CH_2CH_2NR^K$, $CH_2CH$=N, CH=CH—$NR^K$, OCH=N, SCH=N and form together with the carbon atoms the two $R^5$ are bonded to a 5- or 6-membered partially unsaturated or aromatic carbocyclic or heterocyclic ring, wherein the ring is unsubstituted or substituted with 1 or 2 substituents selected from =O, OH, $CH_3$, $OCH_3$, halogen, halomethyl and halomethoxy; each $R^7$ is independently halogen, cyano, hydroxy, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, $C_1$-$C_6$-alkoxy, $C_2$-$C_6$-alkenyloxy, $C_1$-$C_6$-alkylthio, ($C_1$-$C_6$-alkoxy)carbonyl, $OSi(R^e)_3$, wherein the carbon atoms of the aforementioned aliphatic or cycloaliphatic radicals are unsubstituted, partially or fully halogenated and/or oxygenated;

each IV is independently halogen, cyano, azido, nitro, —SCN, $SF_5$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, cycloalkyl, $Si(R^e)_3$, $OR^A$, $SR^A$, $OSO_2R^B$, $S(O)_xR^B$, —$S(O)_xN(R^D)^2$, $N(R^D)_2$, $C(=O)N(R^D)_2$, $C(=S)N(R^D)_2$, $C(=O)OR^A$, phenyl unsubstituted or substituted with up to 5 $R^E$;

a 3-, 4-, 5-, 6- or 7-membered saturated, partially unsaturated or aromatic heterocyclic ring containing 1, 2 or 3 heteroatoms or heteroatom groups selected from N, O, S, NO, SO, $SO_2$, wherein the aforementioned ring is unsubstituted or substituted with up to 5 $R^E$, or two $R^a$ present on one carbon atom are together =O, =$C(R^F)_2$, =$NR^D$, $NOR^A$, =$NNR^D$, or two $R^a$ form a 3-, 4-, 5-, 6-, 7- or 8-membered saturated or partially unsaturated carbocyclic or heterocyclic ring together with the carbon atoms the two $R^a$ are bonded to;

each $R^b$ is independently halogen, cyano, azido, nitro, —SCN, $SF_5$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, $C_1$-$C_6$-alkyl-$C_3$-$C_8$-cycloalkyl, $Si(R^G)_3$, $OR^H$, $SR^H$, $OSO_2R^J$, $S(O)_xR^J$, —$S(O)_xN(R^K)_2$, $N(R^K)_2$, $C(=O)N(R^K)_2$, $C(=S)N(R^K)_2$, $C(=O)OR^H$, or two $R^b$ present on one carbon atom are together =O, =$C(R^L)_2$, =$NR^K$, =$NOR^H$, $NNR^K$, or two $R^b$ form a 3-, 4-, 5-, 6-, 7- or 8-membered saturated or partially unsaturated carbocyclic or heterocyclic ring together with the carbon atoms the two $R^b$ are bonded to;

each $R^c$ is independently halogen, cyano, azido, nitro, —SCN, $SF_5$, $C_1$-$C_6$-alkyl, $C_2$-$C_6$-alkenyl, $C_2$-$C_6$-alkynyl, $C_3$-$C_8$-cycloalkyl, wherein the carbon atoms of the aforementioned aliphatic or cycloaliphatic radicals are unsubstituted or substituted with one or more $R^M$;

Si(R$^G$)$_3$, OR$^H$, SR$^H$, OS(O)$_x$R$^J$, S(O)$_x$R$^J$, —S(O)$_x$N(R$^K$)$_2$, N(R$^K$)$_2$, C(=O)R$^N$, C(=O)OR$^H$, C(=NR$^K$)R$^N$, C(=O)N(R$^K$)$_2$, C(=S)N(R$^K$)$_2$;

each R$^d$ is independently halogen, cyano, azido, nitro, —SCN, SF$_5$, C$_1$-C$_6$-alkyl, C$_2$-C$_6$-alkenyl, C$_2$-C$_6$-alkynyl, C$_3$-C$_8$-cycloalkyl, wherein the carbon atoms of the aforementioned aliphatic or cycloaliphatic radicals are unsubstituted or substituted with one or more R$^M$;

Si(R$^G$)$_3$, OR$^H$, SR$^H$, OS(O)$_x$R$^J$, S(O)$_x$R$^J$, —S(O)$_x$N(R$^K$)$_2$, N(R$^K$)$_2$, C(=O)R$^N$, C(=O)OR$^H$, C(=NR$^K$)R$^N$, C(=O)N(R$^K$)$_2$, C(=S)N(R$^K$)$_2$, or two R$^d$ present on one atom of a saturated or partially unsaturated heterocyclic ring are together =O, =C(R$^L$)$_2$; =NR$^K$, =NOR$^H$ or =NNR$^K$;

each R$^e$ is independently halogen, C$_1$-C$_6$ alkyl, C$_1$-C$_6$ haloalkyl, C$_1$-C$_6$ alkoxyalkyl, C$_2$-C$_6$ alkenyl, C$_2$-C$_6$ haloalkenyl, C$_2$-C$_6$ alkynyl, C$_2$-C$_6$ haloalkynyl, C$_3$-C$_8$ cycloalkyl, C$_3$-C$_8$ halocycloalkyl, C$_1$-C$_6$ haloalkoxyalkyl, phenyl, a 3-, 4-, 5-, 6- or 7-membered saturated, partially unsaturated or aromatic heterocyclic ring containing 1, 2 or 3 heteroatoms or heteroatom groups selected from N, O, S, NO, SO, SO$_2$;

each R$^f$ is independently hydrogen, cyano, C$_1$-C$_6$-alkyl, C$_1$-C$_6$-alkylsulfinyl, C$_1$-C$_6$-alkylsulfonyl, C$_3$-C$_8$-cycloalkyl, C$_2$-C$_6$-alkenyl, C$_2$-C$_6$-alkynyl, wherein the carbon atoms of the aforementioned aliphatic or cycloaliphatic radicals are unsubstituted or substituted with one or more R$^M$;

Si(R$^e$)$_3$, S(O)$_x$R$^B$, —S(O)$_x$N(R$^D$)$_2$, N(R$^D$)$_2$, —N=C(R$^F$)$_2$, C(=O)R$^Q$, C(=O)N(R$^D$)$_2$, C(=S)N(R$^D$)$_2$, C(=O)OR$^A$, phenyl, a 3-, 4-, 5-, 6- or 7-membered saturated, partially unsaturated or aromatic heterocyclic ring containing 1, 2 or 3 heteroatoms or heteroatom groups selected from N, O, S, NO, SO, SO$_2$;

each R$^h$ is independently hydrogen, cyano, C$_1$-C$_6$-alkyl, C$_1$-C$_6$-alkoxy, C$_1$-C$_6$-alkylthio, C$_3$-C$_8$-cycloalkyl, C$_2$-C$_6$-alkenyl, C$_2$-C$_6$-alkynyl, wherein the carbon atoms of the aforementioned aliphatic or cycloaliphatic radicals are unsubstituted or substituted with one or more R$^M$;

N(R$^D$)$_2$, —N=C(R$^F$)$_2$, C(=O)R$^Q$, C(=O)N(R$^D$)$_2$, C(=S)N(R$^D$)$_2$, C(=O)OR$^A$, phenyl, a 3-, 4-, 5-, 6- or 7-membered saturated, partially unsaturated or aromatic heterocyclic ring containing 1, 2 or 3 heteroatoms or heteroatom groups selected from N, O, S, NO, SO, SO$_2$;

each R$^i$ is independently hydrogen, C$_1$-C$_6$-alkyl, C$_1$-C$_6$-alkoxy, C$_1$-C$_6$-alkylthio, C$_3$-C$_8$-cycloalkyl, C$_2$-C$_6$-alkenyl, C$_2$-C$_6$-alkynyl, wherein the carbon atoms of the aforementioned aliphatic or cycloaliphatic radicals are unsubstituted or substituted with one or more R$^M$, S(O)$_x$R$^B$, —S(O)$_x$N(R$^D$)$_2$, C(=O)R$^S$, C(=O)OR$^A$, C(=O)N(R$^D$)$_2$, C(=S)R$^S$, C(=S)SR$^A$, C(=S)N(R$^D$)$_2$, C(=NR$^D$)R$^S$, phenyl unsubstituted or substituted with up to 5 R$^E$;

a 3-, 4-, 5-, 6- or 7-membered saturated, partially unsaturated or aromatic heterocyclic ring containing 1, 2 or 3 heteroatoms or heteroatom groups selected from N, O, S, NO, SO, SO$_2$, wherein the aforementioned ring is unsubstituted or substituted with up to 5 R$^E$, or two R$^i$ on one nitrogen atom are together a C$_2$-C$_7$ alkylene chain and form together with the nitrogen atom they are bonded to a 3-, 4-, 5-, 6-, 7- or 8-membered saturated, partially unsaturated or aromatic ring, wherein the alkylene chain may contain 1 or 2 heteroatoms or heteroatom groups selected from N, O, S, NO, SO, SO$_2$, and wherein the alkylene chain is unsubstituted or substituted with halogen, C$_1$-C$_6$-alkyl, C$_1$-C$_6$-haloalkyl, C$_1$-C$_6$-alkoxy, C$_1$-C$_6$-haloalkoxy, C$_1$-C$_6$-alkylthio, C$_1$-C$_6$-haloalkylthio, C$_2$-C$_6$-alkenyl, C$_2$-C$_6$-haloalkenyl, C$_2$-C$_6$-alkynyl, C$_2$-C$_6$-haloalkynyl;

each R$^m$ is independently hydrogen, —SCN, SF$_5$, C$_1$-C$_6$-alkyl, C$_1$-C$_6$-alkoxy, C$_1$-C$_6$-alkylthio, C$_3$-C$_8$-cycloalkyl, C$_2$-C$_6$-alkenyl, C$_2$-C$_6$-alkynyl, wherein the carbon atoms of the aforementioned aliphatic or cycloaliphatic radicals are unsubstituted or substituted with one or more R$^M$, Si(R$^e$)$_3$, OR$^A$, SR$^A$, OSO$_2$R$^B$, N(R$^D$)$_2$, C(=O)N(R$^D$)$_2$, C(=S)N(R$^D$)$^2$, C(=O)OR$^A$, phenyl unsubstituted or substituted with up to 5 R$^E$;

a 3-, 4-, 5-, 6- or 7-membered saturated, partially unsaturated or aromatic heterocyclic ring containing 1, 2 or 3 heteroatoms or heteroatom groups selected from N, O, S, NO, SO, SO$_2$, wherein the aforementioned ring is unsubstituted or substituted with up to 5 R$^E$;

each R$^A$ is independently hydrogen, cyano, C$_1$-C$_6$-alkylsulfinyl, C$_1$-C$_6$-alkylsulfonyl, trimethylsilyl, triethylsilyl, tert-butyldimethylsilyl, C$_1$-C$_6$-alkyl, C$_2$-C$_6$-alkenyl, C$_2$-C$_6$-alkynyl, C$_3$-C$_8$-cycloalkyl, wherein the four last mentioned radicals are unsubstituted, partially or fully halogenated and/or oxygenated and/or carry 1 or 2 radicals selected from C$_1$-C$_4$ alkoxy;

phenyl, benzyl, pyridyl, phenoxy, wherein the four last mentioned radicals are unsubstituted, partially or fully halogenated and/or carry 1, 2 or 3 substituents selected from C$_1$-C$_6$-alkyl, C$_1$-C$_6$-haloalkyl, C$_1$-C$_6$-alkoxy, C$_1$-C$_6$ haloalkoxy and (C$_1$-C$_6$-alkoxy)carbonyl;

each R$^B$ is independently hydrogen, cyano, C$_1$-C$_6$-alkoxy, C$_1$-C$_6$-haloalkoxy, C$_1$-C$_6$-alkylthio, C$_1$-C$_6$-haloalkylthio, trimethylsilyl, triethylsilyl, tert-butyldimethylsilyl, C$_1$-C$_6$-alkyl, C$_2$-C$_6$-alkenyl, C$_2$-C$_6$-alkynyl, C$_3$-C$_8$-cycloalkyl, wherein the four last mentioned radicals are unsubstituted, partially or fully halogenated and/or oxygenated and/or carry 1 or 2 radicals selected from C$_1$-C$_4$ alkoxy;

phenyl, benzyl, pyridyl, phenoxy, wherein the four last mentioned radicals are unsubstituted, partially or fully halogenated and/or carry 1, 2 or 3 substituents selected from C$_1$-C$_6$-alkyl, C$_1$-C$_6$-haloalkyl, C$_1$-C$_6$-alkoxy, C$_1$-C$_6$ haloalkoxy and (C$_1$-C$_6$-alkoxy)carbonyl;

each R$^D$ is independently hydrogen, cyano, C$_1$-C$_6$-alkoxy, C$_1$-C$_6$-haloalkoxy, C$_1$-C$_6$-alkylthio, C$_1$-C$_6$-alkylsulfinyl, C$_1$-C$_6$-alkylsulfonyl, C$_1$-C$_6$-haloalkylthio, trimethylsilyl, triethylsilyl, tert-butyldimethylsilyl, C$_1$-C$_6$-alkyl, C$_2$-C$_6$-alkenyl, C$_2$-C$_6$-alkynyl, C$_3$-C$_8$-cycloalkyl, wherein the four last mentioned radicals are unsubstituted, partially or fully halogenated and/or oxygenated and/or carry 1 or 2 radicals selected from C$_1$-C$_4$-alkoxy;

phenyl, benzyl, pyridyl, phenoxy, wherein the four last mentioned radicals are unsubstituted, partially or fully halogenated and/or carry 1, 2 or 3 substituents selected from C$_1$-C$_6$-alkyl, C$_1$-C$_6$-haloalkyl, C$_1$-C$_6$-alkoxy, C$_1$-C$_6$ haloalkoxy and (C$_1$-C$_6$-alkoxy)carbonyl, or two R$^D$ on one nitrogen atom are together a C$_2$-C$_6$ alkylene chain and form together with the nitrogen atom they are bonded to a 3-, 4-, 5-, 6-, or 7-membered saturated, partially unsaturated or aromatic ring, wherein the alkylene chain may contain 1 or 2 heteroatoms or heteroatom groups selected from N, O, S, NO, SO, $SO_2$, and wherein the alkylene chain is unsubstituted or substituted with halogen, $C_1$-$C_4$-haloalkyl, $C_1$-$C_4$-alkoxy or $C_1$-$C_4$-haloalkoxy;

each $R^E$ is independently cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, wherein the four last mentioned radicals are unsubstituted, partially or fully halogenated and/or oxygenated and/or carry 1 or 2 radicals selected from $C_1$-$C_4$-alkoxy, or two $R^E$ present on one atom of a saturated or partially unsaturated heterocyclic ring are together =O, =N($C_1$-$C_6$-alkyl), =NO($C_1$-$C_6$-alkyl), =CH($C_1$-$C_4$-alkyl) or =C($C_1$-$C_4$-alkyl)$C_1$-$C_4$-alkyl;

each $R^F$ is independently $C_1$-$C_4$ alkyl, $C_1$-$C_6$ cycloalkyl, $C_1$-$C_4$ alkoxyalkyl, phenyl or benzyl;

each $R^G$ is independently halogen, $C_1$-$C_6$ alkyl, $C_1$-$C_6$ haloalkyl, $C_1$-$C_6$ alkoxyalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ haloalkoxyalkyl;

each $R^H$ is independently hydrogen, cyano, $C_1$-$C_6$-alkylsulfinyl, $C_1$-$C_6$-alkylsulfonyl, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last mentioned radicals are unsubstituted, partially or fully halogenated and/or oxygenated and/or carry 1 or 2 radicals selected from $C_1$-$C_4$-alkoxy;

each $R^J$ is independently hydrogen, cyano, $C_1$-$C_6$-alkoxy, $C_1$-$C_6$-haloalkoxy, $C_1$-$C_6$-alkylthio, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last mentioned radicals are unsubstituted, partially or fully halogenated and/or oxygenated and/or carry 1 or 2 radicals selected from $C_1$-$C_4$ alkoxy;

each $R^K$ is independently hydrogen, cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last mentioned radicals are unsubstituted, partially or fully halogenated and/or oxygenated and/or carry 1 or 2 radicals selected from $C_1$-$C_4$-alkoxy;

each $R^L$ is independently $C_1$-$C_4$ alkyl or $C_1$-$C_4$ alkoxyalkyl;

each $R^M$ is independently halogen, cyano, azido, nitro, OH, SH, —SCN, $SF_5$, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, $C_1$-$C_6$-alkyl-$C_3$-$C_8$-cycloalkyl, wherein the five last mentioned radicals are unsubstituted, partially or fully halogenated and/or oxygenated and/or carry 1 or 2 radicals selected from $C_1$-$C_4$ alkoxy, or two $R^M$ present on one carbon atom are together =O, =CH($C_1$-$C_4$-alkyl), =C($C_1$-$C_4$-alkyl)$C_1$-$C_4$-alkyl, =N($C_1$-$C_6$-alkyl) or =NO($C_1$-$C_6$-alkyl);

each $R^N$ is independently hydrogen, OH, SH, —SCN, $SF_5$, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last mentioned radicals are unsubstituted, partially or fully halogenated and/or oxygenated and/or carry 1 or 2 radicals selected from $C_1$-$C_4$ alkoxy;

each $R^Q$ is independently hydrogen, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$ alkoxy;

phenyl, benzyl, pyridyl, phenoxy, wherein the four last mentioned radicals are unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl;

each $R^S$ is independently hydrogen, OH, SH, —SCN, $SF_5$, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$ alkoxy;

phenyl, benzyl, pyridyl, phenoxy, wherein the four last mentioned radicals are unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy, ($C_1$-$C_6$-alkoxy)carbonyl, ($C_1$-$C_6$-alkyl)amino and di-($C_1$-$C_6$-alkyl)amino;

p is 0 or 1; and x is 1 or 2.

In another embodiment, the invention provides a method for controlling or preventing a parasitic infestation in an animal comprising administering an effective amount of at least one compound of formula (I) as defined above, or a veterinarily acceptable salt thereof, or a composition comprising the compound of formula (I) or salt thereof, to the animal.

In some embodiments, the invention comprises methods of treatment and uses of the compounds of formula (I) wherein Y is phenyl unsubstituted or substituted with 1, 2, 3 or 4 substituents $R^5$; or naphthyl unsubstituted or substituted with 1 or 2 substituents $R^5$.

In other embodiments, the invention comprises methods of treatment and uses of the compounds of formula (I) wherein Q is phenyl unsubstituted or substituted with 1, 2, 3 or 4 substituents $R^6$; cyclohexyl unsubstituted or substituted with 1 or 2 substituents $R^6$; or cyclopentyl unsubstituted or substituted with 1 or 2 substituents $R^6$.

In another embodiment, the invention comprises methods of treatment and uses of compounds of formula (I) wherein $R^1$ is H, halogen, cyano, $C_1$-$C_6$-alkyl, $C_2$-$C_6$-alkenyl, $C_2$-$C_6$-alkynyl, $C_3$-$C_6$-cycloalkyl or ($C_1$-$C_6$-alkoxy)carbonyl, wherein the five radicals last mentioned are unsubstituted or substituted with 1, 2 or 3 substituents selected from halogen, cyano, hydroxy, $OSi(C_1$-$C_6$-alkyl$)_3$, $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy and ($C_1$-$C_6$-alkoxy)carbonyl, wherein the six radicals last mentioned are unsubstituted or partially or fully halogenated, and in particular the ones wherein $R^1$ is H, Me, Et, iPr, cPr, $CH_2CN$, $CF_3$, $CHF_2$, $CH_2F$, $CH_2CH_2F$, $CH_2CHF_2$, $CH_2CF_3$, CN, halogen, $CH_2OH$, $CH_2OMe$, $CH_2OEt$, $CO_2Me$, $CO_2Et$, $CH_2CO_2Me$, $CH_2CO_2Et$, $CH_2OSi(Me)_3$ or $CH_2OSi(Et)_3$.

In one embodiment, preferred are compounds of formula (I) for the methods and uses of the invention are those wherein $R^2$ is H or halogen.

In other embodiments preferred are compounds of formula (I) wherein $R^1$ and $R^2$ form together with the carbon atom to which they are attached a methylene group.

In another embodiment, preferred are compounds of formula (I) for the methods and uses of the invention are those wherein $R^3$ is H, halogen, cyano, $C_1$-$C_6$-alkyl, $C_2$-$C_6$-alkenyl, $C_2$-$C_6$-alkynyl, $C_3$-$C_6$-cycloalkyl or ($C_1$-$C_6$-alkoxy)carbonyl, wherein the five radicals last mentioned are unsubstituted or substituted with 1, 2 or 3 substituents selected from halogen, cyano, hydroxy, $OSi(C_1$-$C_6$-alkyl$)_3$, $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy and ($C_1$-$C_6$-alkoxy)carbonyl, wherein the six radicals last mentioned are unsubstituted or partially or fully halogenated, and in particular the ones wherein $R^3$ is H, Me, Et, iPr, cPr, $CH_2CN$, $CF_3$, $CHF_2$, $CH_2F$, $CH_2CH_2F$, $CH_2CHF_2$, $CH_2CF_3$, CN, halogen, $CH_2OH$, $CH_2OMe$, $CH_2OEt$, $CO_2Me$, $CO_2Et$, $CH_2CO_2Me$, $CH_2CO_2Et$, $CH_2OSi(Me)_3$ or $CH_2OSi(Et)_3$.

In another embodiment, preferred compounds of formula (I) for the methods and uses or the invention are those wherein $R^4$ is H or halogen.

In other embodiments preferred are compounds of formula (I) wherein $R^3$ and $R^4$ form together with the carbon atom to which they are attached a methylene group.

In yet another embodiment, preferred compounds of formula (I) for the methods and uses of the invention are those wherein $R^5$ is halogen, cyano, $SF_5$, tri-($C_1$-$C_4$)silyl-$C_2$-$C_4$-alkynyl, ($C_1$-$C_6$-alkyl)aminocarbonyl, di-($C_1$-$C_6$-alkyl)aminocarbonyl, $C_1$-$C_6$-alkyl, $C_2$-$C_6$-alkenyl, $C_2$-$C_6$-alkynyl, $C_3$-$C_6$-cycloalkyl, phenyl, $C_1$-$C_6$-alkoxy, $C_1$-$C_6$-alkylthio, $C_1$-$C_6$-alkylsulfinyl, $C_1$-$C_6$-alkylsulfonyl, ($C_1$-$C_6$-alkoxy)carbonyl, ($C_1$-$C_6$-alkyl)amino, di-($C_1$-$C_6$-alkyl)amino, ($C_1$-$C_6$-alkyl)carbonyl or ($C_1$-$C_6$-alkyl)carbonyloxy, wherein the 14 radicals last mentioned are unsubstituted or substituted with one or 5 more (particularly up to 3 or in the case of halogen up to the maximum possible number) substituents selected from halogen, cyano, $C_1$-$C_4$-alkyl-$C_3$-$C_6$-cycloalkyl, $C_1$-$C_6$-alkyl, $C_2$-$C_6$-alkenyl, $C_2$-$C_6$-alkynyl, $C_3$-$C_6$-cycloalkyl and $C_1$-$C_6$-alkoxy, wherein the five radicals last mentioned are unsubstituted or partially or fully halogenated, and in particular the ones wherein $R^5$ is halogen (particularly F), Me, Et, iPr, cPr, OMe, OEt, OiPr, ethynyl, (trimethylsilyl)ethynyl, vinyl, Ph, CN, $CF_3$, $OCF_3$, $SF_5$, $CHF_2$, $OCHF_2$, SMe, S(O)Me, $S(O)_2Me$, $SCF_3$, $S(O)CF_3$, $S(O)_2CF_3$, $SCHF_2$, $S(O)CHF_2$, $S(O)_2CHF_2$, $CO_2Me$, $CO_2Et$, C(O)Me, OAc, C(O)NHMe, $C(O)NMe_2$, $CH_2OMe$ or $CH_2OEt$.

In yet another embodiment, preferred compounds of formula (I) for the methods and uses of the invention are those wherein $R^6$ is halogen, cyano, $SF_5$, ($C_1$-$C_6$-alkyl)aminocarbonyl, di-($C_1$-$C_6$-alkyl)aminocarbonyl, $C_1$-$C_6$-alkyl, $C_2$-$C_6$-alkenyl, $C_2$-$C_6$-alkynyl, $C_3$-$C_6$-cycloalkyl, phenyl, $C_1$-$C_6$-alkoxy, $C_1$-$C_6$-alkylsulfinyl, $C_1$-$C_6$-alkylsulfonyl, ($C_1$-$C_6$-alkoxy)carbonyl, ($C_1$-$C_6$-alkyl)amino, di-($C_1$-$C_6$-alkyl)amino, ($C_1$-$C_6$-alkyl)carbonyl or ($C_1$-$C_6$-alkyl)carbonyloxy, wherein the 14 radicals last mentioned are unsubstituted or substituted with one or more (particularly up to 3 or in the case of halogen up to the maximum possible number) substituents selected from halogen, cyano, $C_1$-$C_6$-alkyl, $C_2$-$C_6$-alkenyl, $C_2$-$C_6$-alkynyl, $C_3$-$C_6$-cycloalkyl and $C_1$-$C_6$-alkoxy, wherein the five radicals last mentioned are unsubstituted or partially or fully halogenated, and in particular the ones wherein $R^6$ is halogen (particularly F), Me, Et, iPr, cPr, OMe, OEt, OiPr, ethynyl, (trimethylsilyl)ethynyl, vinyl, Ph, CN, $CF_3$, $OCF_3$, $SF_5$, $CHF_2$, $OCHF_2$, SMe, S(O)Me, $S(O)_2Me$, $SCF_3$, $S(O)CF_3$, $S(O)_2CF_3$, $SCHF_2$, $S(O)CHF_2$, $S(O)_2CHF_2$, $CO_2Me$, $CO_2Et$, C(O)Me, OAc, C(O)NHMe, $C(O)NMe_2$, $CH_2OMe$ or $CH_2OEt$.

In other embodiments for the methods and uses of the invention preferred compounds of formula (I) include those wherein $R^5$ is halogen, Me, Et, iPr, cPr, OMe, OEt, OiPr, ethynyl, (trimethylsilyl)ethynyl, vinyl, Ph, CN, $CF_3$, $OCF_3$, $SF_5$, $CHF_2$, $OCHF_2$, SMe, S(O)Me, $S(O)_2Me$, $SCF_3$, $S(O)CF_3$, $S(O)_2CF_3$, $SCHF_2$, $S(O)CHF_2$, $S(O)_2CHF_2$, $CO_2Me$, $CO_2Et$, C(O)Me, OAc, C(O)NHMe, $C(O)NMe_2$, $CH_2OMe$ or $CH_2OEt$;

or two $R^5$ on two adjacent carbon atoms present on one phenyl ring are together a bridge selected from N=CH—CH=CH, N=CH—CH=N, $OCH_2CH_2O$, $O(CH_2)O$ and form together with the carbon atoms the two $R^5$ are bonded to a 5- or 6-membered partially unsaturated or aromatic heterocyclic ring, wherein the ring is unsubstituted.

In another embodiment, the methods and uses of the invention comprise compounds of formula (I) wherein $R^6$ is halogen, Me, Et, iPr, cPr, tBu, OMe, OEt, OnPr, OiPr, OtBu, OPh, ethynyl, (trimethylsilyl)ethynyl, vinyl, Ph, $NO_2$, CN, $CF_3$, $OCF_3$, $SF_5$, $CHF_2$, $OCHF_2$, SMe, S(O)Me, $S(O)_2Me$, $SCF_3$, $S(O)CF_3$, $S(O)_2CF_3$, $SCHF_2$, $S(O)CHF_2$, $S(O)_2CHF_2$, $CO_2Me$, $CO_2Et$, $CO_2iPr$, C(O)Me, OAc, C(O)NHMe, $C(O)NMe_2$, $CH_2OMe$, $CH_2OEt$, fluoromethyl, 2,2,2-trifluoroethyl, 1,2,2,2-tetrafluoro-1-(trifluoromethyl)ethyl, 2,2,2-trifluoro-1-hydroxy-1-(trifluoromethyl)ethyl, dimethoxymethyl, chloro(difluoro)methoxy, 2,2,2-trifluoroethoxy, 2,2-difluorocyclopropoxy, tert-butylsulfanyl, dimethylcarbamoylsulfanyl, morpholine-4-carbonyl, acetamido, 2-pyridyl, 3-pyridyl, 4-pyridyl, pyrrol-1-yl, pyrazol-1-yl, imidazol-1-yl or 1,2,4-triazol-1-yl.

In another embodiment, the methods and uses of the invention comprise compounds of formula (I) wherein p is 0 or 1, and in particular the ones wherein p is 0.

In another embodiment, the methods and uses of the invention comprise compounds of formula (I) wherein Y is phenyl unsubstituted or substituted with 1, 2 or 3 substituents $R^5$; or naphthyl unsubstituted or substituted with 1 substituent $R^5$.

In yet another embodiment, the methods and uses of the invention comprise compounds of formula (I) wherein Q is phenyl unsubstituted or substituted with 1, 2 or 3 substituents $R^6$; or cyclohexyl unsubstituted or substituted with 1 substituent $R^6$.

In still another embodiment of the invention, the methods and uses comprise compounds of formula (I) wherein $R^1$ is H, Me, Et, CN, $CH_2CN$, $CH_2CF_3$, halogen, $CH_2OH$, $CH_2OMe$, $CH_2OEt$, $CH_2CO_2Me$, $CH_2CO_2Et$, $CH_2OSi(Me)_3$ or $CH_2OSi(Et)_3$.

In another embodiment, the methods and uses comprise compounds of formula (I) wherein $R^2$ is H or halogen.

In another embodiment, the methods and uses of the invention comprise compounds of formula (I) wherein $R^3$ is H, Me, Et, CN, $CH_2CN$, $CH_2CF_3$, halogen, $CH_2OH$, $CH_2OMe$, $CH_2OEt$, $CH_2CO_2Me$, $CH_2CO_2Et$, $CH_2OSi(Me)_3$ or $CH_2OSi(Et)_3$.

In another embodiment of the invention, the methods and uses comprise compounds of formula (I) wherein $R^4$ is H or halogen.

In another embodiment, the methods and uses of the invention comprise compounds of formula (I) wherein $R^5$ is halogen, cyano, tri-$(C_1$-$C_4)$silyl-$C_2$-$C_4$-alkynyl, $C_1$-$C_6$-alkyl, $C_2$-$C_6$-alkenyl, $C_2$-$C_6$-alkynyl, $C_3$-$C_6$-cycloalkyl, phenyl, $C_1$-$C_6$-alkoxy, $C_1$-$C_6$-alkylthio or $(C_1$-$C_6$-alkoxy)carbonyl, wherein the eight radicals last mentioned are unsubstituted or partially or fully halogenated, and in particular the ones wherein $R^5$ is halogen (particularly Cl, F), Me, OMe, CN, $CF_3$, $OCF_3$ or ethynyl.

In yet another embodiment, the methods and uses of the invention are those compounds of formula (I) wherein $R^6$ is halogen, cyano, tri-$(C_1$-$C_4)$silyl-$C_2$-$C_4$-alkynyl, $C_1$-$C_6$-alkyl, $C_2$-$C_6$-alkenyl, $C_2$-$C_6$-alkynyl, $C_3$-$C_6$-cycloalkyl, phenyl, $C_1$-$C_6$-alkoxy, $C_1$-$C_6$-alkylthio or $(C_1$-$C_6$-alkoxy)carbonyl, wherein the eight radicals last mentioned are unsubstituted or partially or fully halogenated, and in particular the ones wherein $R^6$ is halogen (particularly Cl, F), Me, OMe, CN, $CF_3$, $OCF_3$ or ethynyl.

In another embodiment, the methods and uses of the invention comprise compounds of formula (I) wherein p is 0 or 1, and in particular the ones wherein p is 0.

In another embodiment, the methods and uses of the invention comprise compounds of formula (I) wherein Y is phenyl unsubstituted or substituted with 1 or 2 substituents $R^5$.

In another embodiment of the invention, the methods and uses comprise compounds of formula (I) wherein Q is phenyl unsubstituted or substituted with 1 or 2 substituents $R^6$, and in particular the ones wherein Q is phenyl unsubstituted or substituted with 1 substituent $R^6$.

In another embodiment, the methods and uses comprise compounds of formula (I) wherein $R^1$ is H, F, Me, Et, CN, $CH_2CN$ or $CH_2OMe$, and in particular the ones wherein $R^1$ is H.

In another embodiment, the methods and uses comprise compounds of formula (I) wherein $R^2$ is H.

In another embodiment, the methods and uses comprise compounds of formula (I) wherein $R^3$ is H, F, Me, Et, CN, $CH_2CN$ or $CH_2OMe$, and in particular the ones wherein $R^3$ is H.

In yet another embodiment, the methods and uses comprise compounds of formula (I) wherein $R^4$ is H.

In another embodiment, the methods and uses comprise compounds of formula (I) wherein $R^5$ is F, ethynyl or $CF_3$.

In still another embodiment, the methods and uses comprise compounds of formula (I) wherein $R^6$ is F, ethynyl or $CF_3$.

In another embodiment, the methods and uses comprise compounds of formula (I) wherein p is 0 or 1, and in particular the ones wherein p is 0.

In another embodiment, the methods and uses comprise compounds of formula (I) wherein all symbols and indices have the preferred meanings.

In another embodiment of the invention, the methods and uses comprise compounds of formula (I) wherein all symbols and indices have the more preferred meanings.

In another embodiment, the methods and uses comprise compounds of formula (I) wherein all symbols and indices have the even more preferred meanings.

In another embodiment of the invention, the methods and uses comprise compounds of formula (I) wherein Y is phenyl unsubstituted or substituted with 1, 2, 3, 4 or 5 substituents $R^5$; or naphthyl unsubstituted or substituted with 1 or 2 substituents $R^5$;

Q is phenyl unsubstituted or substituted with 1, 2, 3 or 4 substituents $R^6$; cyclohexyl unsubstituted or substituted with 1 or 2 substituents $R^6$; or cyclopentyl unsubstituted or substituted with 1 or 2 substituents $R^6$;

$R^1$ is H, halogen, cyano, $C_2$-$C_6$-alkenyl, $C_2$-$C_6$-alkynyl, $C_3$-$C_6$-cycloalkyl or $(C_1$-$C_6$-alkoxy)carbonyl, wherein the five radicals last mentioned are unsubstituted or substituted with 1, 2 or 3 substituents selected from halogen, cyano, hydroxy, $OSi(C_1$-$C_6$-alkyl)$_3$, $C_2$-$C_6$-alkenyl, $C_2$-$C_6$-alkynyl, $C_3$-$C_6$-cycloalkyl, $C_1$-$C_6$-alkoxy and $(C_1$-$C_6$-alkoxy)carbonyl, wherein the six radicals last mentioned are unsubstituted or partially or fully halogenated;

$R^2$ is H or halogen;

or $R^1$ and $R^2$ form together with the carbon atom to which they are attached a methylene group;

$R^3$ is H, halogen, cyano, $C_2$-$C_6$-alkenyl, $C_2$-$C_6$-alkynyl, $C_3$-$C_6$-cycloalkyl or $(C_1$-$C_6$-alkoxy)carbonyl, wherein the five radicals last mentioned are unsubstituted or substituted with 1, 2 or 3 substituents selected from halogen, cyano, hydroxy, $OSi(C_1$-$C_6$-alkyl)$_3$, $C_2$-$C_6$-alkenyl, $C_2$-$C_6$-alkynyl, $C_3$-$C_6$-cycloalkyl, $C_1$-$C_6$-alkoxy and $(C_1$-$C_6$-alkoxy)carbonyl, wherein the six radicals last mentioned are unsubstituted or partially or fully halogenated;

$R^4$ is H or halogen;

or $R^3$ and $R^4$ form together with the carbon atom to which they are attached a methylene group;

$R^5$ is halogen, cyano, $SF_5$, $(C_1$-$C_6$-alkyl)aminocarbonyl, di-$(C_1$-$C_6$-alkyl)aminocarbonyl, $C_1$-$C_6$-alkyl, $C_2$-$C_6$-alkenyl, $C_2$-$C_6$-alkynyl, $C_3$-$C_6$-cycloalkyl, phenyl, $C_1$-$C_6$-alkoxy, $C_1$-$C_6$-alkylsulfonyl, $(C_1$-$C_6$-alkoxy)carbonyl, $(C_1$-$C_6$-alkyl)amino, di-$(C_1$-$C_6$-alkyl)amino, $(C_1$-$C_6$-alkyl)carbonyl or $(C_1$-$C_6$-alkyl)carbonyloxy, wherein the 14 radicals last mentioned are unsubstituted or substituted with one or more substituents selected from halogen, cyano, $C_1$-$C_6$-alkyl, $C_2$-$C_6$-alkenyl, $C_2$-$C_6$-alkynyl, $C_3$-$C_6$-cycloalkyl and $C_1$-$C_6$-alkoxy, wherein the five radicals last mentioned are unsubstituted or partially or fully halogenated;

or two $R^5$ on two adjacent carbon atoms present on one phenyl ring are together a bridge selected from N=CH—CH=CH, N=CH—CH=N, $OCH_2CH_2O$, $O(CH_2)O$ and form together with the carbon atoms the two $R^5$ are bonded to a 5- or 6-membered partially unsaturated or aromatic heterocyclic ring, wherein the ring is unsubstituted;

$R^6$ is halogen, nitro, cyano, $SF_5$, 2,2,2-trifluoro-1-hydroxy-1-(trifluoromethyl)ethyl, $(C_1$-$C_6$-alkyl)aminocarbonyl, di-$(C_1$-$C_6$-alkyl)aminocarbonyl, dimethylcarbamoylsulfanyl, morpholine-4-carbonyl, acetamido, pyridyl, pyrrolyl, pyrazolyl, imidazolyl, triazolyl, $C_1$-$C_6$-alkyl, $C_2$-$C_6$-alkenyl, $C_2$-$C_6$-alkynyl, $C_3$-$C_6$-cycloalkyl, phenyl, $C_1$-$C_6$-alkoxy, $C_3$-$C_6$-cycloalkoxy, phenoxy, $C_1$-$C_6$-alkylthio, $C_1$-$C_6$-alkylsulfinyl, $C_1$-$C_6$-alkylsulfonyl, $(C_1$-$C_6$-alkoxy)carbonyl, $(C_1$-$C_6$-alkyl)amino, di-$(C_1$-$C_6$-alkyl)amino, $(C_1$-$C_6$-alkyl)carbonyl or $(C_1$-$C_6$-alkyl)carbonyloxy, wherein the 16 radicals last mentioned are unsubstituted or substituted with one or more substituents selected from halogen, cyano, $C_1$-$C_6$-alkyl, $C_2$-$C_6$-alkenyl, $C_2$-$C_6$-alkynyl, $C_3$-$C_6$-cycloalkyl and $C_1$-$C_6$-alkoxy, wherein the five radicals last mentioned are unsubstituted or partially or fully halogenated;

p is 0 or 1.

In other embodiments preferred are compounds of formula (I) for the methods and uses of the invention are those wherein Y is phenyl unsubstituted or substituted with 1, 2, 3 or 4 substituents $R^5$; or naphthyl unsubstituted or substituted with 1 or 2 substituents $R^5$;

Q is phenyl unsubstituted or substituted with 1, 2, 3 or 4 substituents $R^6$; cyclohexyl unsubstituted or substituted with 1 or 2 substituents $R^6$; or cyclopentyl unsubstituted or substituted with 1 or 2 substituents $R^6$;

$R^1$ is H, halogen, cyano, $C_1$-$C_6$-alkyl, $C_2$-$C_6$-alkenyl, $C_2$-$C_6$-alkynyl, $C_3$-$C_6$-cycloalkyl or ($C_1$-$C_6$-alkoxy)carbonyl, wherein the five radicals last mentioned are unsubstituted or substituted with 1, 2 or 3 substituents selected from halogen, cyano, hydroxy, $OSi(C_1$-$C_6$-alkyl$)_3$, $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy and ($C_1$-$C_6$-alkoxy)carbonyl, wherein the six radicals last mentioned are unsubstituted or partially or fully halogenated;

$R^2$ is H or halogen;

or $R^1$ and $R^2$ form together with the carbon atom to which they are attached a methylene group;

$R^3$ is H, halogen, cyano, $C_1$-$C_6$-alkyl, $C_2$-$C_6$-alkenyl, $C_2$-$C_6$-alkynyl, $C_3$-$C_6$-cycloalkyl or ($C_1$-$C_6$-alkoxy)carbonyl, wherein the five radicals last mentioned are unsubstituted or substituted with 1, 2 or 3 substituents selected from halogen, cyano, hydroxy, $OSi(C_1$-$C_6$-alkyl$)_3$, $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy and ($C_1$-$C_6$-alkoxy)carbonyl, wherein the six radicals last mentioned are unsubstituted or partially or fully halogenated;

$R^4$ is H or halogen;

or $R^3$ and $R^4$ form together with the carbon atom to which they are attached a methylene group;

$R^5$ is halogen, cyano, $SF_5$, ($C_1$-$C_6$-alkyl)aminocarbonyl, di-($C_1$-$C_6$-alkyl)aminocarbonyl, $C_1$-$C_6$-alkyl, $C_2$-$C_6$-alkenyl, $C_2$-$C_6$-alkynyl, $C_3$-$C_6$-cycloalkyl, phenyl, $C_1$-$C_6$-alkoxy, $C_1$-$C_6$-alkylthio, $C_1$-$C_6$-alkylsulfinyl, $C_1$-$C_6$-alkylsulfonyl ($C_1$-$C_6$-alkoxy)carbonyl, ($C_1$-$C_6$-alkyl)amino, di-($C_1$-$C_6$-alkyl)amino, ($C_1$-$C_6$-alkyl)carbonyl or ($C_1$-$C_6$-alkyl)carbonyloxy, wherein the 14 radicals last mentioned are unsubstituted or substituted with one or more substituents selected from halogen, cyano, $C_1$-$C_4$-alkyl-$C_3$-$C_6$-cycloalkyl, $C_1$-$C_6$-alkyl, $C_2$-$C_6$-alkenyl, $C_2$-$C_6$-alkynyl, $C_3$-$C_6$-cycloalkyl and $C_1$-$C_6$-alkoxy, wherein the five radicals last mentioned are unsubstituted or partially or fully halogenated;

$R^6$ is halogen, cyano, $SF_5$, tri-($C_1$-$C_4$)silyl-$C_2$-$C_4$-alkynyl, ($C_1$-$C_6$-alkyl)aminocarbonyl, di-($C_1$-$C_6$-alkyl)aminocarbonyl, $C_1$-$C_6$-alkyl, $C_2$-$C_6$-alkenyl, $C_2$-$C_6$-alkynyl, $C_3$-$C_6$-cycloalkyl, phenyl, $C_1$-$C_6$-alkoxy, $C_1$-$C_6$-alkylthio, $C_1$-$C_6$-alkylsulfinyl, $C_1$-$C_6$-alkyl sulfonyl, ($C_1$-$C_6$-alkoxy)carbonyl, ($C_1$-$C_6$-alkyl)amino, di-($C_1$-$C_6$-alkyl)amino, ($C_1$-$C_6$-alkyl)carbonyl or ($C_1$-$C_6$-alkyl)carbonyloxy, wherein the 14 radicals last mentioned are unsubstituted or substituted with one or more substituents selected from halogen, cyano, $C_1$-$C_4$-alkyl-$C_3$-$C_6$-cycloalkyl, $C_1$-$C_6$-alkyl, $C_2$-$C_6$-alkenyl, $C_2$-$C_6$-alkynyl, $C_3$-$C_6$-cycloalkyl and $C_1$-$C_6$-alkoxy, wherein the five radicals last mentioned are unsubstituted or partially or fully halogenated;

p is 0 or 1.

In another embodiment, the methods and uses of the invention comprise compounds of formula (I) wherein Y is phenyl unsubstituted or substituted with 1, 2, 3, 4 or 5 substituents $R^5$; or naphthyl unsubstituted or substituted with 1 substituent $R^5$;

Q is phenyl unsubstituted or substituted with 1, 2 or 3 substituents $R^6$; or cyclohexyl unsubstituted or substituted with 1 substituent $R^6$;

$R^1$ is H, Me, Et, CN, $CH_2CN$, $CH_2CF_3$, halogen, $CH_2OH$, $CH_2OMe$, $CH_2OEt$, $CH_2CO_2Me$, $CH_2CO_2Et$, $CH_2OSi(Me)_3$ or $CH_2OSi(Et)_3$;

$R^2$ is H or halogen;

$R^3$ is H, Me, Et, CN, $CH_2CN$, $CH_2CF_3$, halogen, $CH_2OH$, $CH_2OMe$, $CH_2OEt$, $CH_2CO_2Me$, $CH_2CO_2Et$, $CH_2OSi(Me)_3$ or $CH_2OSi(Et)_3$;

$R^4$ is H or halogen;

$R^5$ is halogen, cyano, $C_1$-$C_6$-alkyl, $C_2$-$C_6$-alkenyl, $C_2$-$C_6$-alkynyl, $C_3$-$C_6$-cycloalkyl, phenyl, $C_1$-$C_6$-alkoxy, $C_1$-$C_6$-alkylthio or ($C_1$-$C_6$-alkoxy)carbonyl, wherein the eight radicals last mentioned are unsubstituted or partially or fully halogenated;

or two $R^5$ on two adjacent carbon atoms present on one phenyl ring are together a bridge selected from N=CH—CH=CH, N=CH—CH=N, $OCH_2CH_2O$, $O(CH_2)O$ and form together with the carbon atoms the two $R^5$ are bonded to a 5- or 6-membered partially unsaturated or aromatic heterocyclic ring, wherein the ring is unsubstituted;

$R^6$ is halogen, nitro, cyano, 2,2,2-trifluoro-1-hydroxy-1-(trifluoromethyl)ethyl, dimethoxymethyl, dimethylcarbamoylsulfanyl, morpholine-4-carbonyl, acetamido, pyridyl, pyrrolyl, pyrazolyl, imidazolyl, triazolyl, $C_1$-$C_6$-alkyl, $C_2$-$C_6$-alkenyl, $C_2$-$C_6$-alkynyl, $C_3$-$C_6$-cycloalkyl, phenyl, $C_1$-$C_6$-alkoxy, $C_3$-$C_6$-cycloalkoxy, phenoxy, $C_1$-$C_6$-alkylsulfonyl or ($C_1$-$C_6$-alkoxy)carbonyl, wherein the eleven radicals last mentioned are unsubstituted or partially or fully halogenated;

p is 0 or 1.

In yet another embodiment of the invention, the methods and uses comprise compounds of formula (I) wherein Y is phenyl unsubstituted or substituted with 1, 2 or 3 substituents $R^5$; or naphthyl unsubstituted or substituted with 1 substituent $R^5$;

Q is phenyl unsubstituted or substituted with 1, 2 or 3 substituents $R^6$; or cyclohexyl unsubstituted or substituted with 1 substituent $R^6$;

$R^1$ is H, Me, Et, CN, $CH_2CN$, $CH_2CF_3$, halogen, $CH_2OH$, $CH_2OMe$, $CH_2OEt$, $CH_2CO_2Me$, $CH_2CO_2Et$, $CH_2OSi(Me)_3$ or $CH_2OSi(Et)_3$;

$R^2$ is H or halogen;

$R^3$ is H, Me, Et, CN, $CH_2CN$, $CH_2CF_3$, halogen, $CH_2OH$, $CH_2OMe$, $CH_2OEt$, $CH_2CO_2Me$, $CH_2CO_2Et$, $CH_2OSi(Me)_3$ or $CH_2OSi(Et)_3$;

$R^4$ is H or halogen;

$R^5$ is halogen, cyano, $C_1$-$C_6$-alkyl, $C_2$-$C_6$-alkenyl, $C_2$-$C_6$-alkynyl, $C_3$-$C_6$-cycloalkyl, phenyl, $C_1$-$C_6$-alkoxy, $C_1$-$C_6$-alkylthio or ($C_1$-$C_6$-alkoxy)carbonyl, wherein the eight radicals last mentioned are unsubstituted or partially or fully halogenated;

$R^6$ is halogen, cyano, $C_1$-$C_6$-alkyl, $C_2$-$C_6$-alkenyl, $C_2$-$C_6$-alkynyl, $C_3$-$C_6$-cycloalkyl, phenyl, $C_1$-$C_6$-alkoxy, $C_1$-$C_6$-alkylthio or ($C_1$-$C_6$-alkoxy)carbonyl, wherein the eight radicals last mentioned are unsubstituted or partially or fully halogenated;

p is 0 or 1.

In another embodiment, the methods and uses comprise compounds of formula (I) wherein Y is phenyl unsubstituted or substituted with 1, 2 or 3 substituents $R^5$;

Q is phenyl unsubstituted or substituted with 1 or 2 substituents $R^6$;

$R^1$ is H, F, Me, Et, CN, $CH_2CN$ or $CH_2OMe$;

$R^2$ is H;

$R^3$ is H, F, Me, Et, CN, $CH_2CN$ or $CH_2OMe$;

$R^4$ is H;

$R^5$ is F, ethynyl or $CF_3$;

$R^6$ is F, ethynyl or $CF_3$;

p is 0 or 1.

In another embodiment, the methods and uses comprise compounds of formula (I) wherein Y is phenyl unsubstituted or substituted with 1 or 2 substituents $R^5$;

Q is phenyl unsubstituted or substituted with 1 or 2 substituents $R^6$;

$R^1$ is H, F, Me, Et, CN, $CH_2CN$ or $CH_2OMe$;

$R^2$ is H;

$R^3$ is H, F, Me, Et, CN, $CH_2CN$ or $CH_2OMe$;

$R^4$ is H;

$R^5$ is F, ethynyl or $CF_3$;

$R^6$ is F, ethynyl or $CF_3$;

p is 0 or 1.

In another embodiment, the methods and uses comprise compounds of formula (I) wherein Y is 4-fluorophenyl, 3-fluorophenyl, 4-ethynylphenyl, 4-trifluoromethylphenyl, 3,5-difluorophenyl or 3,4,5-trifluorophenyl.

In another embodiment, the methods and uses comprise compounds of formula (I) wherein Y is 4-fluorophenyl, 3-fluorophenyl, 4-ethynylphenyl, 4-trifluoromethylphenyl or 3,5-difluorophenyl.

In another embodiment, the methods and uses comprise compounds of formula (I) wherein Y is 3,4,5-trifluorophenyl.

In another embodiment, the methods and uses comprise compounds of formula (I) wherein Q is 4-fluorophenyl, 4-ethynylphenyl or 4-trifluoromethylphenyl.

In another embodiment, the methods and uses comprise compounds of formula (I) wherein $R^1$, $R^2$, $R^3$ and $R^4$ are H.

In yet another embodiment of the invention, the methods and uses comprise compounds of formula (I) wherein $R^1$ and $R^2$ are H; and p is 0.

In another embodiment, the methods and uses comprise compounds wherein Q is phenyl unsubstituted or substituted with one or more $R^6$.

In another embodiment, the methods and uses comprise compounds wherein $R^1$ and $R^2$ do not form together with the carbon atom to which they are attached a methylene group.

In another embodiment, the methods and uses comprise compounds wherein $R^3$ and $R^4$ do not form together with the carbon atom to which they are attached a methylene group.

In yet another embodiment of the invention, the methods and uses comprise compounds wherein neither $R^1$ and $R^2$ nor $R^3$ and $R^4$ form together with the carbon atom to which they are attached a methylene group.

In another embodiment, the methods and uses of the invention comprise compounds of formula (I) wherein the compounds are those of formulae (Ia-1), (Ia-2) or (Ia-3),

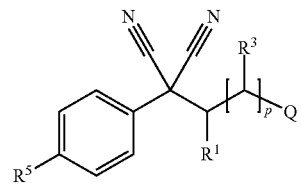

(Ia-1)

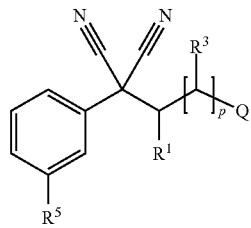

(Ia-2)

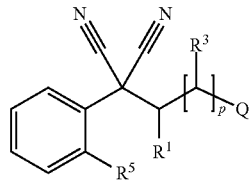

(Ia-3)

wherein Y is phenyl substituted with 1 substituent $R^5$; $R^2$ is H; $R^4$ is H; Q is as defined in formula (I); and p, $R^3$ and $R^5$ are as defined in Table A.

In still other embodiments, the methods and uses of the invention comprise compounds of formulae (Ia-1), (Ia-2) or (Ia-3) wherein Y=unsubstituted phenyl. In line with this, the symbol "-" in column "$R^5$" in table A means that the corresponding compounds do not carry a substituent $R^5$, i.e. Y=unsubstituted phenyl.

TABLE A

| No. | p | $R^1$ | $R^3$ | $R^5$ |
|---|---|---|---|---|
| A-001 | 0 | H | — | — |
| A-002 | 0 | H | — | F |
| A-003 | 0 | H | — | Cl |
| A-004 | 0 | H | — | Br |
| A-005 | 0 | H | — | Me |
| A-006 | 0 | H | — | Et |
| A-007 | 0 | H | — | iPr |
| A-008 | 0 | H | — | cPr |
| A-009 | 0 | H | — | tBu |
| A-010 | 0 | H | — | OMe |
| A-011 | 0 | H | — | OEt |
| A-012 | 0 | H | — | OiPr |
| A-013 | 0 | H | — | vinyl |
| A-014 | 0 | H | — | ethynyl |
| A-015 | 0 | H | — | CN |
| A-016 | 0 | H | — | $CF_3$ |
| A-017 | 0 | H | — | $OCF_3$ |
| A-018 | 0 | H | — | $CHF_2$ |
| A-019 | 0 | H | — | $CH_2F$ |
| A-020 | 0 | H | — | $OCHF_2$ |
| A-021 | 0 | H | — | $OCH_2F$ |
| A-022 | 1 | H | H | — |
| A-023 | 1 | H | H | F |
| A-024 | 1 | H | H | Cl |
| A-025 | 1 | H | H | Br |
| A-026 | 1 | H | H | Me |
| A-027 | 1 | H | H | Et |
| A-028 | 1 | H | H | iPr |
| A-029 | 1 | H | H | cPr |
| A-030 | 1 | H | H | tBu |
| A-031 | 1 | H | H | OMe |
| A-032 | 1 | H | H | OEt |

TABLE A-continued

| No. | p | R¹ | R³ | R⁵ |
|---|---|---|---|---|
| A-033 | 1 | H | H | OiPr |
| A-034 | 1 | H | H | vinyl |
| A-035 | 1 | H | H | ethynyl |
| A-036 | 1 | H | H | CN |
| A-037 | 1 | H | H | $CF_3$ |
| A-038 | 1 | H | H | $OCF_3$ |
| A-039 | 1 | H | H | $CHF_2$ |
| A-040 | 1 | H | H | $CH_2F$ |
| A-041 | 1 | H | H | $OCHF_2$ |
| A-042 | 1 | H | H | $OCH_2F$ |
| A-043 | 0 | Me | — | — |
| A-044 | 0 | Me | — | F |
| A-045 | 0 | Me | — | Cl |
| A-046 | 0 | Me | — | Br |
| A-047 | 0 | Me | — | Me |
| A-048 | 0 | Me | — | Et |
| A-049 | 0 | Me | — | iPr |
| A-050 | 0 | Me | — | cPr |
| A-051 | 0 | Me | — | tBu |
| A-052 | 0 | Me | — | OMe |
| A-053 | 0 | Me | — | OEt |
| A-054 | 0 | Me | — | OiPr |
| A-055 | 0 | Me | — | vinyl |
| A-056 | 0 | Me | — | ethynyl |
| A-057 | 0 | Me | — | CN |
| A-058 | 0 | Me | — | $CF_3$ |
| A-059 | 0 | Me | — | $OCF_3$ |
| A-060 | 0 | Me | — | $CHF_2$ |
| A-061 | 0 | Me | — | $CH_2F$ |
| A-062 | 0 | Me | — | $OCHF_2$ |
| A-063 | 0 | Me | — | $OCH_2F$ |
| A-064 | 0 | Et | — | — |
| A-065 | 0 | Et | — | F |
| A-066 | 0 | Et | — | Cl |
| A-067 | 0 | Et | — | Br |
| A-068 | 0 | Et | — | Me |
| A-069 | 0 | Et | — | Et |
| A-070 | 0 | Et | — | iPr |
| A-071 | 0 | Et | — | cPr |
| A-072 | 0 | Et | — | tBu |
| A-073 | 0 | Et | — | OMe |
| A-074 | 0 | Et | — | OEt |
| A-075 | 0 | Et | — | OiPr |
| A-076 | 0 | Et | — | vinyl |
| A-077 | 0 | Et | — | ethynyl |
| A-078 | 0 | Et | — | CN |
| A-079 | 0 | Et | — | $CF_3$ |
| A-080 | 0 | Et | — | $OCF_3$ |
| A-081 | 0 | Et | — | $CHF_2$ |
| A-082 | 0 | Et | — | $CH_2F$ |
| A-083 | 0 | Et | — | $OCHF_2$ |
| A-084 | 0 | Et | — | $OCH_2F$ |
| A-085 | 0 | CN | — | — |
| A-086 | 0 | CN | — | F |
| A-087 | 0 | CN | — | Cl |
| A-088 | 0 | CN | — | Br |
| A-089 | 0 | CN | — | Me |
| A-090 | 0 | CN | — | Et |
| A-091 | 0 | CN | — | iPr |
| A-092 | 0 | CN | — | cPr |
| A-093 | 0 | CN | — | tBu |
| A-094 | 0 | CN | — | OMe |
| A-095 | 0 | CN | — | OEt |
| A-096 | 0 | CN | — | OiPr |
| A-097 | 0 | CN | — | vinyl |
| A-098 | 0 | CN | — | ethynyl |
| A-099 | 0 | CN | — | CN |
| A-100 | 0 | CN | — | $CF_3$ |
| A-101 | 0 | CN | — | $OCF_3$ |
| A-102 | 0 | CN | — | $CHF_2$ |
| A-103 | 0 | CN | — | $CH_2F$ |
| A-104 | 0 | CN | — | $OCHF_2$ |
| A-105 | 0 | CN | — | $OCH_2F$ |
| A-106 | 0 | $CF_3$ | — | — |
| A-107 | 0 | $CF_3$ | — | F |
| A-108 | 0 | $CF_3$ | — | Cl |
| A-109 | 0 | $CF_3$ | — | Br |
| A-110 | 0 | $CF_3$ | — | Me |
| A-111 | 0 | $CF_3$ | — | Et |
| A-112 | 0 | $CF_3$ | — | iPr |
| A-113 | 0 | $CF_3$ | — | cPr |
| A-114 | 0 | $CF_3$ | — | tBu |
| A-115 | 0 | $CF_3$ | — | OMe |
| A-116 | 0 | $CF_3$ | — | OEt |
| A-117 | 0 | $CF_3$ | — | OiPr |
| A-118 | 0 | $CF_3$ | — | vinyl |
| A-119 | 0 | $CF_3$ | — | ethynyl |
| A-120 | 0 | $CF_3$ | — | CN |
| A-121 | 0 | $CF_3$ | — | $CF_3$ |
| A-122 | 0 | $CF_3$ | — | $OCF_3$ |
| A-123 | 0 | $CF_3$ | — | $CHF_2$ |
| A-124 | 0 | $CF_3$ | — | $CH_2F$ |
| A-125 | 0 | $CF_3$ | — | $OCHF_2$ |
| A-126 | 0 | $CF_3$ | — | $OCH_2F$ |
| A-127 | 0 | $CH_2CN$ | — | — |
| A-128 | 0 | $CH_2CN$ | — | F |
| A-129 | 0 | $CH_2CN$ | — | Cl |
| A-130 | 0 | $CH_2CN$ | — | Br |
| A-131 | 0 | $CH_2CN$ | — | Me |
| A-132 | 0 | $CH_2CN$ | — | Et |
| A-133 | 0 | $CH_2CN$ | — | iPr |
| A-134 | 0 | $CH_2CN$ | — | cPr |
| A-135 | 0 | $CH_2CN$ | — | tBu |
| A-136 | 0 | $CH_2CN$ | — | OMe |
| A-137 | 0 | $CH_2CN$ | — | OEt |
| A-138 | 0 | $CH_2CN$ | — | OiPr |
| A-139 | 0 | $CH_2CN$ | — | vinyl |
| A-140 | 0 | $CH_2CN$ | — | ethynyl |
| A-141 | 0 | $CH_2CN$ | — | CN |
| A-142 | 0 | $CH_2CN$ | — | $CF_3$ |
| A-143 | 0 | $CH_2CN$ | — | $OCF_3$ |
| A-144 | 0 | $CH_2CN$ | — | $CHF_2$ |
| A-145 | 0 | $CH_2CN$ | — | $CH_2F$ |
| A-146 | 0 | $CH_2CN$ | — | $OCHF_2$ |
| A-147 | 0 | $CH_2CN$ | — | $OCH_2F$ |
| A-148 | 0 | $CH_2OMe$ | — | — |
| A-149 | 0 | $CH_2OMe$ | — | F |
| A-150 | 0 | $CH_2OMe$ | — | Cl |
| A-151 | 0 | $CH_2OMe$ | — | Br |
| A-152 | 0 | $CH_2OMe$ | — | Me |
| A-153 | 0 | $CH_2OMe$ | — | Et |
| A-154 | 0 | $CH_2OMe$ | — | iPr |
| A-155 | 0 | $CH_2OMe$ | — | cPr |
| A-156 | 0 | $CH_2OMe$ | — | tBu |
| A-157 | 0 | $CH_2OMe$ | — | OMe |
| A-158 | 0 | $CH_2OMe$ | — | OEt |
| A-159 | 0 | $CH_2OMe$ | — | OiPr |
| A-160 | 0 | $CH_2OMe$ | — | vinyl |
| A-161 | 0 | $CH_2OMe$ | — | ethynyl |
| A-162 | 0 | $CH_2OMe$ | — | CN |
| A-163 | 0 | $CH_2OMe$ | — | $CF_3$ |
| A-164 | 0 | $CH_2OMe$ | — | $OCF_3$ |
| A-165 | 0 | $CH_2OMe$ | — | $CHF_2$ |
| A-166 | 0 | $CH_2OMe$ | — | $CH_2F$ |
| A-167 | 0 | $CH_2OMe$ | — | $OCHF_2$ |
| A-168 | 0 | $CH_2OMe$ | — | $OCH_2F$ |
| A-169 | 1 | Me | H | — |
| A-170 | 1 | Me | H | F |
| A-171 | 1 | Me | H | Cl |
| A-172 | 1 | Me | H | Br |
| A-173 | 1 | Me | H | Me |
| A-174 | 1 | Me | H | Et |
| A-175 | 1 | Me | H | iPr |
| A-176 | 1 | Me | H | cPr |
| A-177 | 1 | Me | H | tBu |
| A-178 | 1 | Me | H | OMe |
| A-179 | 1 | Me | H | OEt |
| A-180 | 1 | Me | H | OiPr |
| A-181 | 1 | Me | H | vinyl |
| A-182 | 1 | Me | H | ethynyl |
| A-183 | 1 | Me | H | CN |
| A-184 | 1 | Me | H | $CF_3$ |
| A-185 | 1 | Me | H | $OCF_3$ |
| A-186 | 1 | Me | H | $CHF_2$ |
| A-187 | 1 | Me | H | $CH_2F$ |
| A-188 | 1 | Me | H | $OCHF_2$ |

TABLE A-continued

| No. | p | R¹ | R³ | R⁵ |
|---|---|---|---|---|
| A-189 | 1 | Me | H | OCH₂F |
| A-190 | 1 | Et | H | — |
| A-191 | 1 | Et | H | F |
| A-192 | 1 | Et | H | Cl |
| A-193 | 1 | Et | H | Br |
| A-194 | 1 | Et | H | Me |
| A-195 | 1 | Et | H | Et |
| A-196 | 1 | Et | H | iPr |
| A-197 | 1 | Et | H | cPr |
| A-198 | 1 | Et | H | tBu |
| A-199 | 1 | Et | H | OMe |
| A-200 | 1 | Et | H | OEt |
| A-201 | 1 | Et | H | OiPr |
| A-202 | 1 | Et | H | vinyl |
| A-203 | 1 | Et | H | ethynyl |
| A-204 | 1 | Et | H | CN |
| A-205 | 1 | Et | H | CF₃ |
| A-206 | 1 | Et | H | OCF₃ |
| A-207 | 1 | Et | H | CHF₂ |
| A-208 | 1 | Et | H | CH₂F |
| A-209 | 1 | Et | H | OCHF₂ |
| A-210 | 1 | Et | H | OCH₂F |
| A-211 | 1 | CN | H | — |
| A-212 | 1 | CN | H | F |
| A-213 | 1 | CN | H | Cl |
| A-214 | 1 | CN | H | Br |
| A-215 | 1 | CN | H | Me |
| A-216 | 1 | CN | H | Et |
| A-217 | 1 | CN | H | iPr |
| A-218 | 1 | CN | H | cPr |
| A-219 | 1 | CN | H | tBu |
| A-220 | 1 | CN | H | OMe |
| A-221 | 1 | CN | H | OEt |
| A-222 | 1 | CN | H | OiPr |
| A-223 | 1 | CN | H | vinyl |
| A-224 | 1 | CN | H | ethynyl |
| A-225 | 1 | CN | H | CN |
| A-226 | 1 | CN | H | CF₃ |
| A-227 | 1 | CN | H | OCF₃ |
| A-228 | 1 | CN | H | CHF₂ |
| A-229 | 1 | CN | H | CH₂F |
| A-230 | 1 | CN | H | OCHF₂ |
| A-231 | 1 | CN | H | OCH₂F |
| A-232 | 1 | CF₃ | H | — |
| A-233 | 1 | CF₃ | H | F |
| A-234 | 1 | CF₃ | H | Cl |
| A-235 | 1 | CF₃ | H | Br |
| A-236 | 1 | CF₃ | H | Me |
| A-237 | 1 | CF₃ | H | Et |
| A-238 | 1 | CF₃ | H | iPr |
| A-239 | 1 | CF₃ | H | cPr |
| A-240 | 1 | CF₃ | H | tBu |
| A-241 | 1 | CF₃ | H | OMe |
| A-242 | 1 | CF₃ | H | OEt |
| A-243 | 1 | CF₃ | H | OiPr |
| A-244 | 1 | CF₃ | H | vinyl |
| A-245 | 1 | CF₃ | H | ethynyl |
| A-246 | 1 | CF₃ | H | CN |
| A-247 | 1 | CF₃ | H | CF₃ |
| A-248 | 1 | CF₃ | H | OCF₃ |
| A-249 | 1 | CF₃ | H | CHF₂ |
| A-250 | 1 | CF₃ | H | CH₂F |
| A-251 | 1 | CF₃ | H | OCHF₂ |
| A-252 | 1 | CF₃ | H | OCH₂F |
| A-253 | 1 | CH₂CN | H | — |
| A-254 | 1 | CH₂CN | H | F |
| A-255 | 1 | CH₂CN | H | Cl |
| A-256 | 1 | CH₂CN | H | Br |
| A-257 | 1 | CH₂CN | H | Me |
| A-258 | 1 | CH₂CN | H | Et |
| A-259 | 1 | CH₂CN | H | iPr |
| A-260 | 1 | CH₂CN | H | cPr |
| A-261 | 1 | CH₂CN | H | tBu |
| A-262 | 1 | CH₂CN | H | OMe |
| A-263 | 1 | CH₂CN | H | OEt |
| A-264 | 1 | CH₂CN | H | OiPr |
| A-265 | 1 | CH₂CN | H | vinyl |
| A-266 | 1 | CH₂CN | H | ethynyl |
| A-267 | 1 | CH₂CN | H | CN |
| A-268 | 1 | CH₂CN | H | CF₃ |
| A-269 | 1 | CH₂CN | H | OCF₃ |
| A-270 | 1 | CH₂CN | H | CHF₂ |
| A-271 | 1 | CH₂CN | H | CH₂F |
| A-272 | 1 | CH₂CN | H | OCHF₂ |
| A-273 | 1 | CH₂CN | H | OCH₂F |
| A-274 | 1 | CH₂OMe | H | — |
| A-275 | 1 | CH₂OMe | H | F |
| A-276 | 1 | CH₂OMe | H | Cl |
| A-277 | 1 | CH₂OMe | H | Br |
| A-278 | 1 | CH₂OMe | H | Me |
| A-279 | 1 | CH₂OMe | H | Et |
| A-280 | 1 | CH₂OMe | H | iPr |
| A-281 | 1 | CH₂OMe | H | cPr |
| A-282 | 1 | CH₂OMe | H | tBu |
| A-283 | 1 | CH₂OMe | H | OMe |
| A-284 | 1 | CH₂OMe | H | OEt |
| A-285 | 1 | CH₂OMe | H | OiPr |
| A-286 | 1 | CH₂OMe | H | vinyl |
| A-287 | 1 | CH₂OMe | H | ethynyl |
| A-288 | 1 | CH₂OMe | H | CN |
| A-289 | 1 | CH₂OMe | H | CF₃ |
| A-290 | 1 | CH₂OMe | H | OCF₃ |
| A-291 | 1 | CH₂OMe | H | CHF₂ |
| A-292 | 1 | CH₂OMe | H | CH₂F |
| A-293 | 1 | CH₂OMe | H | OCHF₂ |
| A-294 | 1 | CH₂OMe | H | OCH₂F |
| A-295 | 1 | H | Me | — |
| A-296 | 1 | H | Me | F |
| A-297 | 1 | H | Me | Cl |
| A-298 | 1 | H | Me | Br |
| A-299 | 1 | H | Me | Me |
| A-300 | 1 | H | Me | Et |
| A-301 | 1 | H | Me | iPr |
| A-302 | 1 | H | Me | cPr |
| A-303 | 1 | H | Me | tBu |
| A-304 | 1 | H | Me | OMe |
| A-305 | 1 | H | Me | OEt |
| A-306 | 1 | H | Me | OiPr |
| A-307 | 1 | H | Me | vinyl |
| A-308 | 1 | H | Me | ethynyl |
| A-309 | 1 | H | Me | CN |
| A-310 | 1 | H | Me | CF₃ |
| A-311 | 1 | H | Me | OCF₃ |
| A-312 | 1 | H | Me | CHF₂ |
| A-313 | 1 | H | Me | CH₂F |
| A-314 | 1 | H | Me | OCHF₂ |
| A-315 | 1 | H | Me | OCH₂F |
| A-316 | 1 | H | Et | — |
| A-317 | 1 | H | Et | F |
| A-318 | 1 | H | Et | Cl |
| A-319 | 1 | H | Et | Br |
| A-320 | 1 | H | Et | Me |
| A-321 | 1 | H | Et | Et |
| A-322 | 1 | H | Et | iPr |
| A-323 | 1 | H | Et | cPr |
| A-324 | 1 | H | Et | tBu |
| A-325 | 1 | H | Et | OMe |
| A-326 | 1 | H | Et | OEt |
| A-327 | 1 | H | Et | OiPr |
| A-328 | 1 | H | Et | vinyl |
| A-329 | 1 | H | Et | ethynyl |
| A-330 | 1 | H | Et | CN |
| A-331 | 1 | H | Et | CF₃ |
| A-332 | 1 | H | Et | OCF₃ |
| A-333 | 1 | H | Et | CHF₂ |
| A-334 | 1 | H | Et | CH₂F |
| A-335 | 1 | H | Et | OCHF₂ |
| A-336 | 1 | H | Et | OCH₂F |
| A-337 | 1 | H | CN | H |
| A-338 | 1 | H | CN | F |
| A-339 | 1 | H | CN | Cl |
| A-340 | 1 | H | CN | Br |
| A-341 | 1 | H | CN | Me |
| A-342 | 1 | H | CN | Et |
| A-343 | 1 | H | CN | iPr |
| A-344 | 1 | H | CN | cPr |

TABLE A-continued

| No. | p | R$^1$ | R$^3$ | R$^5$ |
|---|---|---|---|---|
| A-345 | 1 | H | CN | tBu |
| A-346 | 1 | H | CN | OMe |
| A-347 | 1 | H | CN | OEt |
| A-348 | 1 | H | CN | OiPr |
| A-349 | 1 | H | CN | vinyl |
| A-350 | 1 | H | CN | ethynyl |
| A-351 | 1 | H | CN | CN |
| A-352 | 1 | H | CN | CF$_3$ |
| A-353 | 1 | H | CN | OCF$_3$ |
| A-354 | 1 | H | CN | CHF$_2$ |
| A-355 | 1 | H | CN | CH$_2$F |
| A-356 | 1 | H | CN | OCHF$_2$ |
| A-357 | 1 | H | CN | OCH$_2$F |
| A-358 | 1 | H | CF$_3$ | — |
| A-359 | 1 | H | CF$_3$ | F |
| A-360 | 1 | H | CF$_3$ | Cl |
| A-361 | 1 | H | CF$_3$ | Br |
| A-362 | 1 | H | CF$_3$ | Me |
| A-363 | 1 | H | CF$_3$ | Et |
| A-364 | 1 | H | CF$_3$ | iPr |
| A-365 | 1 | H | CF$_3$ | cPr |
| A-366 | 1 | H | CF$_3$ | tBu |
| A-367 | 1 | H | CF$_3$ | OMe |
| A-368 | 1 | H | CF$_3$ | OEt |
| A-369 | 1 | H | CF$_3$ | OiPr |
| A-370 | 1 | H | CF$_3$ | vinyl |
| A-371 | 1 | H | CF$_3$ | ethynyl |
| A-372 | 1 | H | CF$_3$ | CN |
| A-373 | 1 | H | CF$_3$ | CF$_3$ |
| A-374 | 1 | H | CF$_3$ | OCF$_3$ |
| A-375 | 1 | H | CF$_3$ | CHF$_2$ |
| A-376 | 1 | H | CF$_3$ | CH$_2$F |
| A-377 | 1 | H | CF$_3$ | OCHF$_2$ |
| A-378 | 1 | H | CF$_3$ | OCH$_2$F |
| A-379 | 1 | H | CH$_2$CN | — |
| A-380 | 1 | H | CH$_2$CN | F |
| A-381 | 1 | H | CH$_2$CN | Cl |
| A-382 | 1 | H | CH$_2$CN | Br |
| A-383 | 1 | H | CH$_2$CN | Me |
| A-384 | 1 | H | CH$_2$CN | Et |
| A-385 | 1 | H | CH$_2$CN | iPr |
| A-386 | 1 | H | CH$_2$CN | cPr |
| A-387 | 1 | H | CH$_2$CN | tBu |
| A-388 | 1 | H | CH$_2$CN | OMe |
| A-389 | 1 | H | CH$_2$CN | OEt |
| A-390 | 1 | H | CH$_2$CN | OiPr |
| A-391 | 1 | H | CH$_2$CN | vinyl |
| A-392 | 1 | H | CH$_2$CN | ethynyl |
| A-393 | 1 | H | CH$_2$CN | CN |
| A-394 | 1 | H | CH$_2$CN | CF$_3$ |
| A-395 | 1 | H | CH$_2$CN | OCF$_3$ |
| A-396 | 1 | H | CH$_2$CN | CHF$_2$ |
| A-397 | 1 | H | CH$_2$CN | CH$_2$F |
| A-398 | 1 | H | CH$_2$CN | OCHF$_2$ |
| A-399 | 1 | H | CH$_2$CN | OCH$_2$F |
| A-400 | 1 | H | CH$_2$OMe | — |
| A-401 | 1 | H | CH$_2$OMe | F |
| A-402 | 1 | H | CH$_2$OMe | Cl |
| A-403 | 1 | H | CH$_2$OMe | Br |
| A-404 | 1 | H | CH$_2$OMe | Me |
| A-405 | 1 | H | CH$_2$OMe | Et |
| A-406 | 1 | H | CH$_2$OMe | iPr |
| A-407 | 1 | H | CH$_2$OMe | cPr |
| A-408 | 1 | H | CH$_2$OMe | tBu |
| A-409 | 1 | H | CH$_2$OMe | OMe |
| A-410 | 1 | H | CH$_2$OMe | OEt |
| A-411 | 1 | H | CH$_2$OMe | OiPr |
| A-412 | 1 | H | CH$_2$OMe | vinyl |
| A-413 | 1 | H | CH$_2$OMe | ethynyl |
| A-414 | 1 | H | CH$_2$OMe | CN |
| A-415 | 1 | H | CH$_2$OMe | CF$_3$ |
| A-416 | 1 | H | CH$_2$OMe | OCF$_3$ |
| A-417 | 1 | H | CH$_2$OMe | CHF$_2$ |
| A-418 | 1 | H | CH$_2$OMe | CH$_2$F |
| A-419 | 1 | H | CH$_2$OMe | OCHF$_2$ |
| A-420 | 1 | H | CH$_2$OMe | OCH$_2$F |

In another embodiment of the invention, the methods and uses comprise compounds of formula (I), wherein the compounds have formulae (Ib-1), (Ib-2), (Ib-3), (Ib-4), (Ib-5) or (Ib-6),

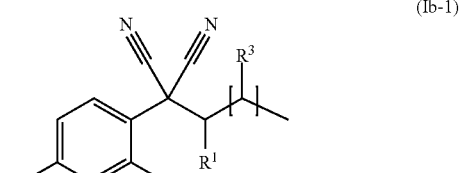
(Ib-1)

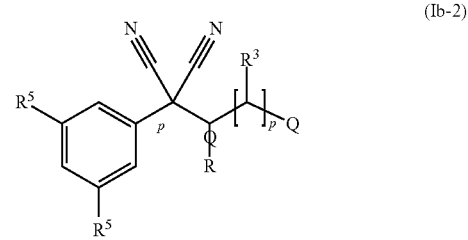
(Ib-2)

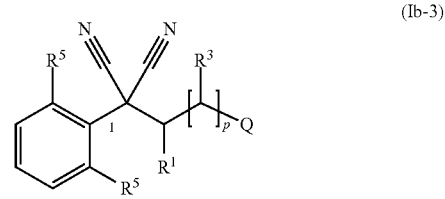
(Ib-3)

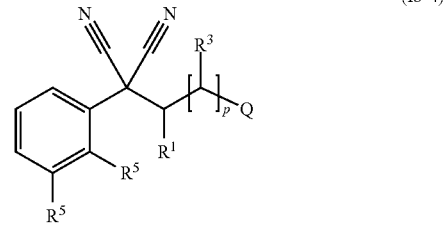
(Ib-4)

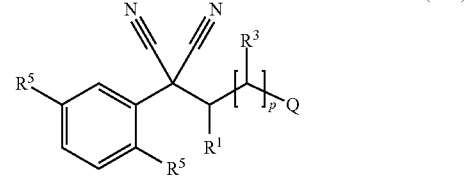
(Ib-5)

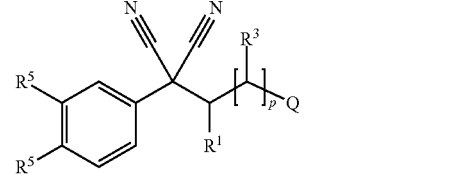
(Ib-6)

wherein Y is phenyl substituted with 2 substituents R$^5$; R$^2$ is H; R$^4$ is H; Q is as defined in formula (I); and p, R$^3$ and R$^5$ are as defined in Table B.

In another embodiment, the methods and uses of the invention comprise compounds of formula (I), wherein the compounds have formulae (Ib-7), (Ib-8), (Ib-9), (Ib-10), (Ib-11) or (Ib-12),

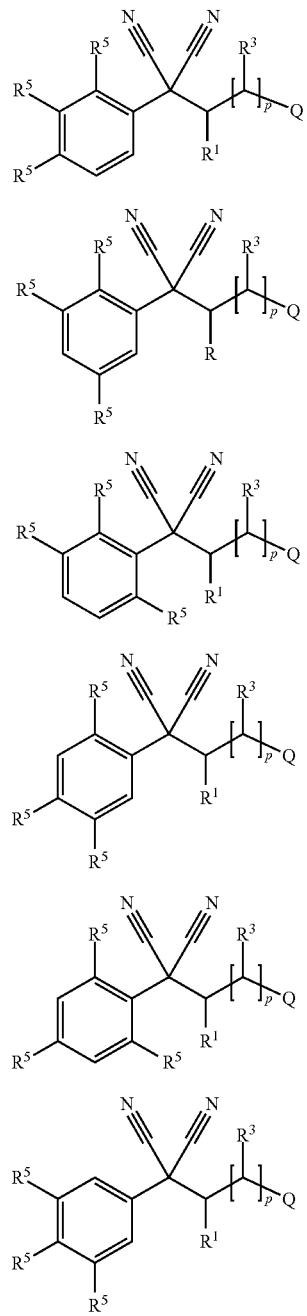

wherein Y is phenyl substituted with 3 substituents $R^5$; $R^2$ is H; $R^4$ is H; Q is as defined in formula (I); and p, $R^1$, $R^3$ and $R^5$ are as defined in Table B.

TABLE B

| No. | p | $R^1$ | $R^3$ | $R^5$ |
|---|---|---|---|---|
| B-001 | 0 | H | — | F |
| B-002 | 0 | H | — | Cl |
| B-003 | 0 | H | — | Br |
| B-004 | 0 | H | — | Me |
| B-005 | 0 | H | — | Et |
| B-006 | 0 | H | — | iPr |
| B-007 | 0 | H | — | cPr |

TABLE B-continued

| No. | p | $R^1$ | $R^3$ | $R^5$ |
|---|---|---|---|---|
| B-008 | 0 | H | — | OMe |
| B-009 | 0 | H | — | OEt |
| B-010 | 0 | H | — | $CF_3$ |
| B-011 | 0 | H | — | $OCF_3$ |
| B-012 | 1 | H | H | F |
| B-013 | 1 | H | H | Cl |
| B-014 | 1 | H | H | Br |
| B-015 | 1 | H | H | Me |
| B-016 | 1 | H | H | Et |
| B-017 | 1 | H | H | iPr |
| B-018 | 1 | H | H | cPr |
| B-019 | 1 | H | H | OMe |
| B-020 | 1 | H | H | OEt |
| B-021 | 1 | H | H | $CF_3$ |
| B-022 | 1 | H | H | $OCF_3$ |
| B-023 | 0 | Me | — | F |
| B-024 | 0 | Me | — | Cl |
| B-025 | 0 | Me | — | Br |
| B-026 | 0 | Me | — | Me |
| B-027 | 0 | Me | — | Et |
| B-028 | 0 | Me | — | iPr |
| B-029 | 0 | Me | — | cPr |
| B-030 | 0 | Me | — | OMe |
| B-031 | 0 | Me | — | OEt |
| B-032 | 0 | Me | — | $CF_3$ |
| B-033 | 0 | Me | — | $OCF_3$ |
| B-034 | 0 | Et | — | F |
| B-035 | 0 | Et | — | Cl |
| B-036 | 0 | Et | — | Br |
| B-037 | 0 | Et | — | Me |
| B-038 | 0 | Et | — | Et |
| B-039 | 0 | Et | — | iPr |
| B-040 | 0 | Et | — | cPr |
| B-041 | 0 | Et | — | OMe |
| B-042 | 0 | Et | — | OEt |
| B-043 | 0 | Et | — | $CF_3$ |
| B-044 | 0 | Et | — | $OCF_3$ |
| B-045 | 0 | CN | — | F |
| B-046 | 0 | CN | — | Cl |
| B-047 | 0 | CN | — | Br |
| B-048 | 0 | CN | — | Me |
| B-049 | 0 | CN | — | Et |
| B-050 | 0 | CN | — | iPr |
| B-051 | 0 | CN | — | cPr |
| B-052 | 0 | CN | — | OMe |
| B-053 | 0 | CN | — | OEt |
| B-054 | 0 | CN | — | $CF_3$ |
| B-055 | 0 | CN | — | $OCF_3$ |
| B-056 | 0 | $CF_3$ | — | F |
| B-057 | 0 | $CF_3$ | — | Cl |
| B-058 | 0 | $CF_3$ | — | Br |
| B-059 | 0 | $CF_3$ | — | Me |
| B-060 | 0 | $CF_3$ | — | Et |
| B-061 | 0 | $CF_3$ | — | iPr |
| B-062 | 0 | $CF_3$ | — | cPr |
| B-063 | 0 | $CF_3$ | — | OMe |
| B-064 | 0 | $CF_3$ | — | OEt |
| B-065 | 0 | $CF_3$ | — | $CF_3$ |
| B-066 | 0 | $CF_3$ | — | $OCF_3$ |
| B-067 | 0 | $CH_2CN$ | — | F |
| B-068 | 0 | $CH_2CN$ | — | Cl |
| B-069 | 0 | $CH_2CN$ | — | Br |
| B-070 | 0 | $CH_2CN$ | — | Me |
| B-071 | 0 | $CH_2CN$ | — | Et |
| B-072 | 0 | $CH_2CN$ | — | iPr |
| B-073 | 0 | $CH_2CN$ | — | cPr |
| B-074 | 0 | $CH_2CN$ | — | OMe |
| B-075 | 0 | $CH_2CN$ | — | OEt |
| B-076 | 0 | $CH_2CN$ | — | $CF_3$ |
| B-077 | 0 | $CH_2CN$ | — | $OCF_3$ |
| B-078 | 0 | $CH_2OMe$ | — | F |
| B-079 | 0 | $CH_2OMe$ | — | Cl |
| B-080 | 0 | $CH_2OMe$ | — | Br |
| B-081 | 0 | $CH_2OMe$ | — | Me |
| B-082 | 0 | $CH_2OMe$ | — | Et |
| B-083 | 0 | $CH_2OMe$ | — | iPr |
| B-084 | 0 | $CH_2OMe$ | — | cPr |
| B-085 | 0 | $CH_2OMe$ | — | OMe |

TABLE B-continued

| No. | p | R¹ | R³ | R⁵ |
|---|---|---|---|---|
| B-086 | 0 | CH₂OMe | — | OEt |
| B-087 | 0 | CH₂OMe | — | CF₃ |
| B-088 | 0 | CH₂OMe | — | OCF₃ |
| B-089 | 1 | Me | H | F |
| B-090 | 1 | Me | H | Cl |
| B-091 | 1 | Me | H | Br |
| B-092 | 1 | Me | H | Me |
| B-093 | 1 | Me | H | Et |
| B-094 | 1 | Me | H | iPr |
| B-095 | 1 | Me | H | cPr |
| B-096 | 1 | Me | H | OMe |
| B-097 | 1 | Me | H | OEt |
| B-098 | 1 | Me | H | CF₃ |
| B-099 | 1 | Me | H | OCF₃ |
| B-100 | 1 | Et | H | F |
| B-101 | 1 | Et | H | Cl |
| B-102 | 1 | Et | H | Br |
| B-103 | 1 | Et | H | Me |
| B-104 | 1 | Et | H | Et |
| B-105 | 1 | Et | H | iPr |
| B-106 | 1 | Et | H | cPr |
| B-107 | 1 | Et | H | OMe |
| B-108 | 1 | Et | H | OEt |
| B-109 | 1 | Et | H | CF₃ |
| B-110 | 1 | Et | H | OCF₃ |
| B-111 | 1 | CN | H | F |
| B-112 | 1 | CN | H | Cl |
| B-113 | 1 | CN | H | Br |
| B-114 | 1 | CN | H | Me |
| B-115 | 1 | CN | H | Et |
| B-116 | 1 | CN | H | iPr |
| B-117 | 1 | CN | H | cPr |
| B-118 | 1 | CN | H | OMe |
| B-119 | 1 | CN | H | OEt |
| B-120 | 1 | CN | H | CF₃ |
| B-121 | 1 | CN | H | OCF₃ |
| B-122 | 1 | CF₃ | H | F |
| B-123 | 1 | CF₃ | H | Cl |
| B-124 | 1 | CF₃ | H | Br |
| B-125 | 1 | CF₃ | H | Me |
| B-126 | 1 | CF₃ | H | Et |
| B-127 | 1 | CF₃ | H | iPr |
| B-128 | 1 | CF₃ | H | cPr |
| B-129 | 1 | CF₃ | H | OMe |
| B-130 | 1 | CF₃ | H | OEt |
| B-131 | 1 | CF₃ | H | CF₃ |
| B-132 | 1 | CF₃ | H | OCF₃ |
| B-133 | 1 | CH₂CN | H | F |
| B-134 | 1 | CH₂CN | H | Cl |
| B-135 | 1 | CH₂CN | H | Br |
| B-136 | 1 | CH₂CN | H | Me |
| B-137 | 1 | CH₂CN | H | Et |
| B-138 | 1 | CH₂CN | H | iPr |
| B-139 | 1 | CH₂CN | H | cPr |
| B-140 | 1 | CH₂CN | H | OMe |
| B-141 | 1 | CH₂CN | H | OEt |
| B-142 | 1 | CH₂CN | H | CF₃ |
| B-143 | 1 | CH₂CN | H | OCF₃ |
| B-144 | 1 | CH₂OMe | H | F |
| B-145 | 1 | CH₂OMe | H | Cl |
| B-146 | 1 | CH₂OMe | H | Br |
| B-147 | 1 | CH₂OMe | H | Me |
| B-148 | 1 | CH₂OMe | H | Et |
| B-149 | 1 | CH₂OMe | H | iPr |
| B-150 | 1 | CH₂OMe | H | cPr |
| B-151 | 1 | CH₂OMe | H | OMe |
| B-152 | 1 | CH₂OMe | H | OEt |
| B-153 | 1 | CH₂OMe | H | CF₃ |
| B-154 | 1 | CH₂OMe | H | OCF₃ |
| B-155 | 1 | H | Me | F |
| B-156 | 1 | H | Me | Cl |
| B-157 | 1 | H | Me | Br |
| B-158 | 1 | H | Me | Me |
| B-159 | 1 | H | Me | Et |
| B-160 | 1 | H | Me | iPr |
| B-161 | 1 | H | Me | cPr |
| B-162 | 1 | H | Me | OMe |
| B-163 | 1 | H | Me | OEt |
| B-164 | 1 | H | Me | CF₃ |
| B-165 | 1 | H | Me | OCF₃ |
| B-166 | 1 | H | Et | F |
| B-167 | 1 | H | Et | Cl |
| B-168 | 1 | H | Et | Br |
| B-169 | 1 | H | Et | Me |
| B-170 | 1 | H | Et | Et |
| B-171 | 1 | H | Et | iPr |
| B-172 | 1 | H | Et | cPr |
| B-173 | 1 | H | Et | OMe |
| B-174 | 1 | H | Et | OEt |
| B-175 | 1 | H | Et | CF₃ |
| B-176 | 1 | H | Et | OCF₃ |
| B-177 | 1 | H | CN | F |
| B-178 | 1 | H | CN | Cl |
| B-179 | 1 | H | CN | Br |
| B-180 | 1 | H | CN | Me |
| B-181 | 1 | H | CN | Et |
| B-182 | 1 | H | CN | iPr |
| B-183 | 1 | H | CN | cPr |
| B-184 | 1 | H | CN | OMe |
| B-185 | 1 | H | CN | OEt |
| B-186 | 1 | H | CN | CF₃ |
| B-187 | 1 | H | CN | OCF₃ |
| B-188 | 1 | H | CF₃ | F |
| B-189 | 1 | H | CF₃ | Cl |
| B-190 | 1 | H | CF₃ | Br |
| B-191 | 1 | H | CF₃ | Me |
| B-192 | 1 | H | CF₃ | Et |
| B-193 | 1 | H | CF₃ | iPr |
| B-194 | 1 | H | CF₃ | cPr |
| B-195 | 1 | H | CF₃ | OMe |
| B-196 | 1 | H | CF₃ | OEt |
| B-197 | 1 | H | CF₃ | CF₃ |
| B-198 | 1 | H | CF₃ | OCF₃ |
| B-199 | 1 | H | CH₂CN | F |
| B-200 | 1 | H | CH₂CN | Cl |
| B-201 | 1 | H | CH₂CN | Br |
| B-202 | 1 | H | CH₂CN | Me |
| B-203 | 1 | H | CH₂CN | Et |
| B-204 | 1 | H | CH₂CN | iPr |
| B-205 | 1 | H | CH₂CN | cPr |
| B-206 | 1 | H | CH₂CN | OMe |
| B-207 | 1 | H | CH₂CN | OEt |
| B-208 | 1 | H | CH₂CN | CF₃ |
| B-209 | 1 | H | CH₂CN | OCF₃ |
| B-210 | 1 | H | CH₂OMe | F |
| B-211 | 1 | H | CH₂OMe | Cl |
| B-212 | 1 | H | CH₂OMe | Br |
| B-213 | 1 | H | CH₂OMe | Me |
| B-214 | 1 | H | CH₂OMe | Et |
| B-215 | 1 | H | CH₂OMe | iPr |
| B-216 | 1 | H | CH₂OMe | cPr |
| B-217 | 1 | H | CH₂OMe | OMe |
| B-218 | 1 | H | CH₂OMe | OEt |
| B-219 | 1 | H | CH₂OMe | CF₃ |
| B-220 | 1 | H | CH₂OMe | OCF₃ |

In another embodiment, the methods and uses of the invention comprise compounds of formula (I), wherein the compounds have formulae (Ic-1), (Ic-2), (Ic-3), (Ic-4), (Ic-5) (Ic-6), (Ic-7), (Ic-8) or (Ic-9),

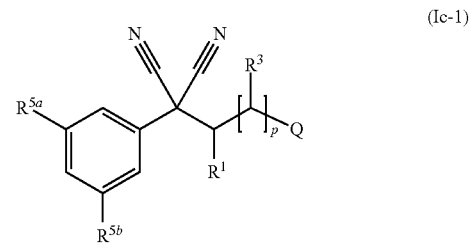

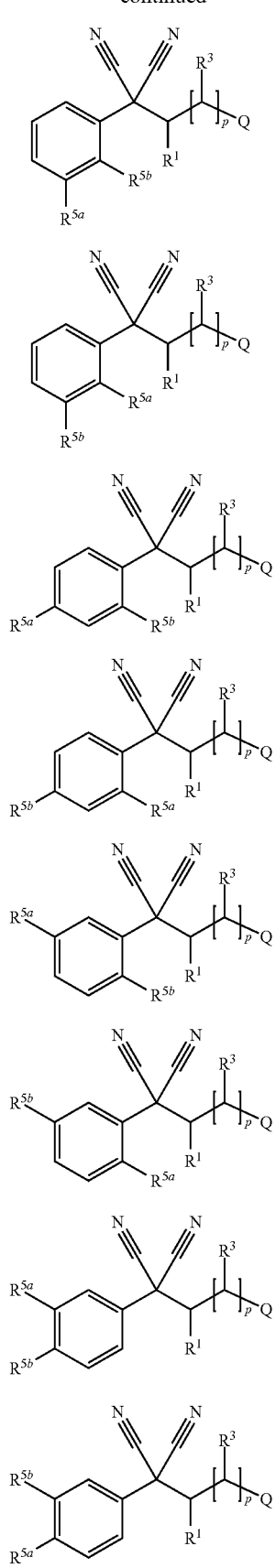

wherein Y is phenyl substituted with 2 substituents $R^5$; one $R^5$ is $R^{5a}$ and the other $R^5$ is $R^{5b}$; $R^2$ is H; $R^4$ is H; Q is as defined in formula (I); and p, $R^1$, $R^3$, $R^{5a}$ and $R^{5b}$ are as defined in Table C.

TABLE C

| No. | p | $R^1$ | $R^3$ | $R^{5a}$ | $R^{5b}$ |
|---|---|---|---|---|---|
| C-001 | 0 | H | — | F | Cl |
| C-002 | 0 | H | — | F | Me |
| C-003 | 0 | H | — | Cl | Me |
| C-004 | 0 | H | — | $CF_3$ | F |
| C-005 | 0 | H | — | $CF_3$ | Cl |
| C-006 | 0 | H | — | $CF_3$ | Me |
| C-007 | 0 | H | — | CN | F |
| C-008 | 0 | H | — | CN | Cl |
| C-009 | 0 | H | — | ethynyl | F |
| C-010 | 0 | H | — | ethynyl | Cl |
| C-011 | 0 | H | — | ethynyl | Me |
| C-012 | 0 | H | — | ethynyl | $CF_3$ |
| C-013 | 0 | H | — | $OCF_3$ | F |
| C-014 | 0 | H | — | $OCF_3$ | Cl |
| C-015 | 0 | H | — | $OCF_3$ | Me |
| C-016 | 0 | H | — | $OCF_3$ | ethynyl |
| C-017 | 1 | H | H | F | Cl |
| C-018 | 1 | H | H | F | Me |
| C-019 | 1 | H | H | Cl | Me |
| C-020 | 1 | H | H | $CF_3$ | F |
| C-021 | 1 | H | H | $CF_3$ | Cl |
| C-022 | 1 | H | H | $CF_3$ | Me |
| C-023 | 1 | H | H | CN | F |
| C-024 | 1 | H | H | CN | Cl |
| C-025 | 1 | H | H | ethynyl | F |
| C-026 | 1 | H | H | ethynyl | Cl |
| C-027 | 1 | H | H | ethynyl | Me |
| C-028 | 1 | H | H | ethynyl | $CF_3$ |
| C-029 | 1 | H | H | $OCF_3$ | F |
| C-030 | 1 | H | H | $OCF_3$ | Cl |
| C-031 | 1 | H | H | $OCF_3$ | Me |
| C-032 | 1 | H | H | $OCF_3$ | ethynyl |
| C-033 | 0 | Me | — | F | Cl |
| C-034 | 0 | Me | — | F | Me |
| C-035 | 0 | Me | — | Cl | Me |
| C-036 | 0 | Me | — | $CF_3$ | F |
| C-037 | 0 | Me | — | $CF_3$ | Cl |
| C-038 | 0 | Me | — | $CF_3$ | Me |
| C-039 | 0 | Me | — | CN | F |
| C-040 | 0 | Me | — | CN | Cl |
| C-041 | 0 | Me | — | ethynyl | F |
| C-042 | 0 | Me | — | ethynyl | Cl |
| C-043 | 0 | Me | — | ethynyl | Me |
| C-044 | 0 | Me | — | ethynyl | $CF_3$ |
| C-045 | 0 | Me | — | $OCF_3$ | F |
| C-046 | 0 | Me | — | $OCF_3$ | Cl |
| C-047 | 0 | Me | — | $OCF_3$ | Me |
| C-048 | 0 | Me | — | $OCF_3$ | ethynyl |
| C-049 | 0 | Et | — | F | Cl |
| C-050 | 0 | Et | — | F | Me |
| C-051 | 0 | Et | — | Cl | Me |
| C-052 | 0 | Et | — | $CF_3$ | F |
| C-053 | 0 | Et | — | $CF_3$ | Cl |
| C-054 | 0 | Et | — | $CF_3$ | Me |
| C-055 | 0 | Et | — | CN | F |
| C-056 | 0 | Et | — | CN | Cl |
| C-057 | 0 | Et | — | CN | Me |
| C-058 | 0 | Et | — | ethynyl | F |
| C-059 | 0 | Et | — | ethynyl | Cl |
| C-060 | 0 | Et | — | ethynyl | Me |
| C-061 | 0 | Et | — | ethynyl | $CF_3$ |
| C-062 | 0 | Et | — | $OCF_3$ | F |
| C-063 | 0 | Et | — | $OCF_3$ | Cl |
| C-064 | 0 | Et | — | $OCF_3$ | Me |
| C-065 | 0 | Et | — | $OCF_3$ | ethynyl |
| C-066 | 0 | CN | — | F | Cl |
| C-067 | 0 | CN | — | F | Me |
| C-068 | 0 | CN | — | Cl | Me |
| C-069 | 0 | CN | — | $CF_3$ | F |
| C-070 | 0 | CN | — | $CF_3$ | Cl |
| C-071 | 0 | CN | — | $CF_3$ | Me |
| C-072 | 0 | CN | — | CN | F |

TABLE C-continued

| No. | p | R¹ | R³ | R⁵ᵃ | R⁵ᵇ |
| --- | --- | --- | --- | --- | --- |
| C-073 | 0 | CN | — | CN | Cl |
| C-074 | 0 | CN | — | ethynyl | F |
| C-075 | 0 | CN | — | ethynyl | Cl |
| C-076 | 0 | CN | — | ethynyl | Me |
| C-077 | 0 | CN | — | ethynyl | CF₃ |
| C-078 | 0 | CN | — | OCF₃ | F |
| C-079 | 0 | CN | — | OCF₃ | Cl |
| C-080 | 0 | CN | — | OCF₃ | Me |
| C-081 | 0 | CN | — | OCF₃ | ethynyl |
| C-082 | 0 | CF₃ | — | F | Cl |
| C-083 | 0 | CF₃ | — | F | Me |
| C-084 | 0 | CF₃ | — | Cl | Me |
| C-085 | 0 | CF₃ | — | CF₃ | F |
| C-086 | 0 | CF₃ | — | CF₃ | Cl |
| C-087 | 0 | CF₃ | — | CF₃ | Me |
| C-088 | 0 | CF₃ | — | CN | F |
| C-089 | 0 | CF₃ | — | CN | Cl |
| C-090 | 0 | CF₃ | — | ethynyl | F |
| C-091 | 0 | CF₃ | — | ethynyl | Cl |
| C-092 | 0 | CF₃ | — | ethynyl | Me |
| C-093 | 0 | CF₃ | — | ethynyl | CF₃ |
| C-094 | 0 | CF₃ | — | OCF₃ | F |
| C-095 | 0 | CF₃ | — | OCF₃ | Cl |
| C-096 | 0 | CF₃ | — | OCF₃ | Me |
| C-097 | 0 | CF₃ | — | OCF₃ | ethynyl |
| C-098 | 0 | CH₂CN | — | F | Cl |
| C-099 | 0 | CH₂CN | — | F | Me |
| C-100 | 0 | CH₂CN | — | Cl | Me |
| C-101 | 0 | CH₂CN | — | CF₃ | F |
| C-102 | 0 | CH₂CN | — | CF₃ | Cl |
| C-103 | 0 | CH₂CN | — | CF₃ | Me |
| C-104 | 0 | CH₂CN | — | CN | F |
| C-105 | 0 | CH₂CN | — | CN | Cl |
| C-106 | 0 | CH₂CN | — | ethynyl | F |
| C-107 | 0 | CH₂CN | — | ethynyl | Cl |
| C-108 | 0 | CH₂CN | — | ethynyl | Me |
| C-109 | 0 | CH₂CN | — | ethynyl | CF₃ |
| C-110 | 0 | CH₂CN | — | OCF₃ | F |
| C-111 | 0 | CH₂CN | — | OCF₃ | Cl |
| C-112 | 0 | CH₂CN | — | OCF₃ | Me |
| C-113 | 0 | CH₂CN | — | OCF₃ | ethynyl |
| C-114 | 0 | CH₂OMe | — | F | Cl |
| C-115 | 0 | CH₂OMe | — | F | Me |
| C-116 | 0 | CH₂OMe | — | Cl | Me |
| C-117 | 0 | CH₂OMe | — | CF₃ | F |
| C-118 | 0 | CH₂OMe | — | CF₃ | Cl |
| C-119 | 0 | CH₂OMe | — | CF₃ | Me |
| C-120 | 0 | CH₂OMe | — | CN | F |
| C-121 | 0 | CH₂OMe | — | CN | Cl |
| C-122 | 0 | CH₂OMe | — | ethynyl | F |
| C-123 | 0 | CH₂OMe | — | ethynyl | Cl |
| C-124 | 0 | CH₂OMe | — | ethynyl | Me |
| C-125 | 0 | CH₂OMe | — | ethynyl | CF₃ |
| C-126 | 0 | CH₂OMe | — | OCF₃ | F |
| C-127 | 0 | CH₂OMe | — | OCF₃ | Cl |
| C-128 | 0 | CH₂OMe | — | OCF₃ | Me |
| C-129 | 0 | CH₂OMe | — | OCF₃ | ethynyl |
| C-130 | 1 | Me | H | F | Cl |
| C-131 | 1 | Me | H | F | Me |
| C-132 | 1 | Me | H | Cl | Me |
| C-133 | 1 | Me | H | CF₃ | F |
| C-134 | 1 | Me | H | CF₃ | Cl |
| C-135 | 1 | Me | H | CF₃ | Me |
| C-136 | 1 | Me | H | CN | F |
| C-137 | 1 | Me | H | CN | Cl |
| C-138 | 1 | Me | H | ethynyl | F |
| C-139 | 1 | Me | H | ethynyl | Cl |
| C-140 | 1 | Me | H | ethynyl | Me |
| C-141 | 1 | Me | H | ethynyl | CF₃ |
| C-142 | 1 | Me | H | OCF₃ | F |
| C-143 | 1 | Me | H | OCF₃ | Cl |
| C-144 | 1 | Me | H | OCF₃ | Me |
| C-145 | 1 | Me | H | OCF₃ | ethynyl |
| C-146 | 1 | Et | H | F | Cl |
| C-147 | 1 | Et | H | F | Me |
| C-148 | 1 | Et | H | Cl | Me |
| C-149 | 1 | Et | H | CF₃ | F |
| C-150 | 1 | Et | H | CF₃ | Cl |
| C-151 | 1 | Et | H | CF₃ | Me |
| C-152 | 1 | Et | H | CN | F |
| C-153 | 1 | Et | H | CN | Cl |
| C-154 | 1 | Et | H | ethynyl | F |
| C-155 | 1 | Et | H | ethynyl | Cl |
| C-156 | 1 | Et | H | ethynyl | Me |
| C-157 | 1 | Et | H | ethynyl | CF₃ |
| C-158 | 1 | Et | H | OCF₃ | F |
| C-159 | 1 | Et | H | OCF₃ | Cl |
| C-160 | 1 | Et | H | OCF₃ | Me |
| C-161 | 1 | Et | H | OCF₃ | ethynyl |
| C-162 | 1 | CN | H | F | Cl |
| C-163 | 1 | CN | H | F | Me |
| C-164 | 1 | CN | H | Cl | Me |
| C-165 | 1 | CN | H | CF₃ | F |
| C-166 | 1 | CN | H | CF₃ | Cl |
| C-167 | 1 | CN | H | CF₃ | Me |
| C-168 | 1 | CN | H | CN | F |
| C-169 | 1 | CN | H | CN | Cl |
| C-170 | 1 | CN | H | ethynyl | F |
| C-171 | 1 | CN | H | ethynyl | Cl |
| C-172 | 1 | CN | H | ethynyl | Me |
| C-173 | 1 | CN | H | ethynyl | CF₃ |
| C-174 | 1 | CN | H | OCF₃ | F |
| C-175 | 1 | CN | H | OCF₃ | Cl |
| C-176 | 1 | CN | H | OCF₃ | Me |
| C-177 | 1 | CN | H | OCF₃ | ethynyl |
| C-178 | 1 | CF₃ | H | F | Cl |
| C-179 | 1 | CF₃ | H | F | Me |
| C-180 | 1 | CF₃ | H | Cl | Me |
| C-181 | 1 | CF₃ | H | CF₃ | F |
| C-182 | 1 | CF₃ | H | CF₃ | Cl |
| C-183 | 1 | CF₃ | H | CF₃ | Me |
| C-184 | 1 | CF₃ | H | CN | F |
| C-185 | 1 | CF₃ | H | CN | Cl |
| C-186 | 1 | CF₃ | H | ethynyl | F |
| C-187 | 1 | CF₃ | H | ethynyl | Cl |
| C-188 | 1 | CF₃ | H | ethynyl | Me |
| C-189 | 1 | CF₃ | H | ethynyl | CF₃ |
| C-190 | 1 | CF₃ | H | OCF₃ | F |
| C-191 | 1 | CF₃ | H | OCF₃ | Cl |
| C-192 | 1 | CF₃ | H | OCF₃ | Me |
| C-193 | 1 | CF₃ | H | OCF₃ | ethynyl |
| C-194 | 1 | CH₂CN | H | F | Cl |
| C-195 | 1 | CH₂CN | H | F | Me |
| C-196 | 1 | CH₂CN | H | Cl | Me |
| C-197 | 1 | CH₂CN | H | CF₃ | F |
| C-198 | 1 | CH₂CN | H | CF₃ | Cl |
| C-199 | 1 | CH₂CN | H | CF₃ | Me |
| C-200 | 1 | CH₂CN | H | CN | F |
| C-201 | 1 | CH₂CN | H | CN | Cl |
| C-202 | 1 | CH₂CN | H | ethynyl | F |
| C-203 | 1 | CH₂CN | H | ethynyl | Cl |
| C-204 | 1 | CH₂CN | H | ethynyl | Me |
| C-205 | 1 | CH₂CN | H | ethynyl | CF₃ |
| C-206 | 1 | CH₂CN | H | OCF₃ | F |
| C-207 | 1 | CH₂CN | H | OCF₃ | Cl |
| C-208 | 1 | CH₂CN | H | OCF₃ | Me |
| C-209 | 1 | CH₂CN | H | OCF₃ | ethynyl |
| C-210 | 1 | CH₂OMe | H | F | Cl |
| C-211 | 1 | CH₂OMe | H | F | Me |
| C-212 | 1 | CH₂OMe | H | Cl | Me |
| C-213 | 1 | CH₂OMe | H | CF₃ | F |
| C-214 | 1 | CH₂OMe | H | CF₃ | Cl |
| C-215 | 1 | CH₂OMe | H | CF₃ | Me |
| C-216 | 1 | CH₂OMe | H | CN | F |
| C-217 | 1 | CH₂OMe | H | CN | Cl |
| C-218 | 1 | CH₂OMe | H | ethynyl | F |
| C-219 | 1 | CH₂OMe | H | ethynyl | Cl |
| C-220 | 1 | CH₂OMe | H | ethynyl | Me |
| C-221 | 1 | CH₂OMe | H | ethynyl | CF₃ |
| C-222 | 1 | CH₂OMe | H | OCF₃ | F |
| C-223 | 1 | CH₂OMe | H | OCF₃ | Cl |
| C-224 | 1 | CH₂OMe | H | OCF₃ | Me |
| C-225 | 1 | CH₂OMe | H | OCF₃ | ethynyl |
| C-226 | 1 | H | Me | F | Cl |
| C-227 | 1 | H | Me | F | Me |
| C-228 | 1 | H | Me | Cl | Me |

TABLE C-continued

| No. | p | R¹ | R³ | R⁵ᵃ | R⁵ᵇ |
|---|---|---|---|---|---|
| C-229 | 1 | H | Me | CF₃ | F |
| C-230 | 1 | H | Me | CF₃ | Cl |
| C-231 | 1 | H | Me | CF₃ | Me |
| C-232 | 1 | H | Me | CN | F |
| C-233 | 1 | H | Me | CN | Cl |
| C-234 | 1 | H | Me | ethynyl | F |
| C-235 | 1 | H | Me | ethynyl | Cl |
| C-236 | 1 | H | Me | ethynyl | Me |
| C-237 | 1 | H | Me | ethynyl | CF₃ |
| C-238 | 1 | H | Me | OCF₃ | F |
| C-239 | 1 | H | Me | OCF₃ | Cl |
| C-240 | 1 | H | Me | OCF₃ | Me |
| C-241 | 1 | H | Me | OCF₃ | ethynyl |
| C-242 | 1 | H | Et | F | Cl |
| C-243 | 1 | H | Et | F | Me |
| C-244 | 1 | H | Et | Cl | Me |
| C-245 | 1 | H | Et | CF₃ | F |
| C-246 | 1 | H | Et | CF₃ | Cl |
| C-247 | 1 | H | Et | CF₃ | Me |
| C-248 | 1 | H | Et | CN | F |
| C-249 | 1 | H | Et | CN | Cl |
| C-250 | 1 | H | Et | ethynyl | F |
| C-251 | 1 | H | Et | ethynyl | Cl |
| C-252 | 1 | H | Et | ethynyl | Me |
| C-253 | 1 | H | Et | ethynyl | CF₃ |
| C-254 | 1 | H | Et | OCF₃ | F |
| C-255 | 1 | H | Et | OCF₃ | Cl |
| C-256 | 1 | H | Et | OCF₃ | Me |
| C-257 | 1 | H | Et | OCF₃ | ethynyl |
| C-258 | 1 | H | CN | F | Cl |
| C-259 | 1 | H | CN | F | Me |
| C-260 | 1 | H | CN | Cl | Me |
| C-261 | 1 | H | CN | CF₃ | F |
| C-262 | 1 | H | CN | CF₃ | Cl |
| C-263 | 1 | H | CN | CF₃ | Me |
| C-264 | 1 | H | CN | CN | F |
| C-265 | 1 | H | CN | CN | Cl |
| C-266 | 1 | H | CN | ethynyl | F |
| C-267 | 1 | H | CN | ethynyl | Cl |
| C-268 | 1 | H | CN | ethynyl | Me |
| C-269 | 1 | H | CN | ethynyl | CF₃ |
| C-270 | 1 | H | CN | OCF₃ | F |
| C-271 | 1 | H | CN | OCF₃ | Cl |
| C-272 | 1 | H | CN | OCF₃ | Me |
| C-273 | 1 | H | CN | OCF₃ | ethynyl |
| C-274 | 1 | H | CF₃ | F | Cl |
| C-275 | 1 | H | CF₃ | F | Me |
| C-276 | 1 | H | CF₃ | Cl | Me |
| C-277 | 1 | H | CF₃ | CF₃ | F |
| C-278 | 1 | H | CF₃ | CF₃ | Cl |
| C-279 | 1 | H | CF₃ | CF₃ | Me |
| C-280 | 1 | H | CF₃ | CN | F |
| C-281 | 1 | H | CF₃ | CN | Cl |
| C-282 | 1 | H | CF₃ | ethynyl | F |
| C-283 | 1 | H | CF₃ | ethynyl | Cl |
| C-284 | 1 | H | CF₃ | ethynyl | Me |
| C-285 | 1 | H | CF₃ | ethynyl | CF₃ |
| C-286 | 1 | H | CF₃ | OCF₃ | F |
| C-287 | 1 | H | CF₃ | OCF₃ | Cl |
| C-288 | 1 | H | CF₃ | OCF₃ | Me |
| C-289 | 1 | H | CF₃ | OCF₃ | ethynyl |
| C-290 | 1 | H | CH₂CN | F | Cl |
| C-291 | 1 | H | CH₂CN | F | Me |
| C-292 | 1 | H | CH₂CN | Cl | Me |
| C-293 | 1 | H | CH₂CN | CF₃ | F |
| C-294 | 1 | H | CH₂CN | CF₃ | Cl |
| C-295 | 1 | H | CH₂CN | CF₃ | Me |
| C-296 | 1 | H | CH₂CN | CN | F |
| C-297 | 1 | H | CH₂CN | CN | Cl |
| C-298 | 1 | H | CH₂CN | ethynyl | F |
| C-299 | 1 | H | CH₂CN | ethynyl | Cl |
| C-300 | 1 | H | CH₂CN | ethynyl | Me |
| C-301 | 1 | H | CH₂CN | ethynyl | CF₃ |
| C-302 | 1 | H | CH₂CN | OCF₃ | F |
| C-303 | 1 | H | CH₂CN | OCF₃ | Cl |
| C-304 | 1 | H | CH₂CN | OCF₃ | Me |
| C-305 | 1 | H | CH₂CN | OCF₃ | ethynyl |
| C-306 | 1 | H | CH₂OMe | F | Cl |
| C-307 | 1 | H | CH₂OMe | F | Me |
| C-308 | 1 | H | CH₂OMe | Cl | Me |
| C-309 | 1 | H | CH₂OMe | CF₃ | F |
| C-310 | 1 | H | CH₂OMe | CF₃ | Cl |
| C-311 | 1 | H | CH₂OMe | CF₃ | Me |
| C-312 | 1 | H | CH₂OMe | CN | F |
| C-313 | 1 | H | CH₂OMe | CN | Cl |
| C-314 | 1 | H | CH₂OMe | ethynyl | F |
| C-315 | 1 | H | CH₂OMe | ethynyl | Cl |
| C-316 | 1 | H | CH₂OMe | ethynyl | Me |
| C-317 | 1 | H | CH₂OMe | ethynyl | CF₃ |
| C-318 | 1 | H | CH₂OMe | OCF₃ | F |
| C-319 | 1 | H | CH₂OMe | OCF₃ | Cl |
| C-320 | 1 | H | CH₂OMe | OCF₃ | Me |
| C-321 | 1 | H | CH₂OMe | OCF₃ | ethynyl |

In other embodiments of the invention, the methods and uses comprise compounds of formula (I) wherein the meaning of variable Q is as given in Table D.

TABLE D

| No. | ring | substituents |
|---|---|---|
| D-001 | 3-substituted cyclopentyl | H |
| D-002 | 3-substituted cyclopentyl | F |
| D-003 | 3-substituted cyclopentyl | Cl |
| D-004 | 3-substituted cyclopentyl | Br |
| D-005 | 3-substituted cyclopentyl | Me |
| D-006 | 3-substituted cyclopentyl | Et |
| D-007 | 3-substituted cyclopentyl | iPr |
| D-008 | 3-substituted cyclopentyl | cPr |
| D-009 | 3-substituted cyclopentyl | tBu |
| D-010 | 3-substituted cyclopentyl | OMe |
| D-011 | 3-substituted cyclopentyl | OEt |
| D-012 | 3-substituted cyclopentyl | OiPr |
| D-013 | 3-substituted cyclopentyl | vinyl |
| D-014 | 3-substituted cyclopentyl | ethynyl |
| D-015 | 3-substituted cyclopentyl | CN |
| D-016 | 3-substituted cyclopentyl | CF₃ |
| D-017 | 3-substituted cyclopentyl | OCF₃ |
| D-018 | 3-substituted cyclopentyl | CHF₂ |
| D-019 | 3-substituted cyclopentyl | CH₂F |
| D-020 | 3-substituted cyclopentyl | OCHF₂ |
| D-021 | 3-substituted cyclopentyl | OCH₂F |
| D-022 | 4-substituted cyclohexyl | H |
| D-023 | 4-substituted cyclohexyl | F |
| D-024 | 4-substituted cyclohexyl | Cl |
| D-025 | 4-substituted cyclohexyl | Br |
| D-026 | 4-substituted cyclohexyl | Me |
| D-027 | 4-substituted cyclohexyl | Et |
| D-028 | 4-substituted cyclohexyl | iPr |
| D-029 | 4-substituted cyclohexyl | cPr |
| D-030 | 4-substituted cyclohexyl | tBu |
| D-031 | 4-substituted cyclohexyl | OMe |
| D-032 | 4-substituted cyclohexyl | OEt |
| D-033 | 4-substituted cyclohexyl | OiPr |
| D-034 | 4-substituted cyclohexyl | vinyl |
| D-035 | 4-substituted cyclohexyl | ethynyl |
| D-036 | 4-substituted cyclohexyl | CN |
| D-037 | 4-substituted cyclohexyl | CF₃ |
| D-038 | 4-substituted cyclohexyl | OCF₃ |
| D-039 | 4-substituted cyclohexyl | CHF₂ |
| D-040 | 4-substituted cyclohexyl | CH₂F |
| D-041 | 4-substituted cyclohexyl | OCHF₂ |
| D-042 | 4-substituted cyclohexyl | OCH₂F |
| D-043 | 4-substituted phenyl | H |
| D-044 | 4-substituted phenyl | F |
| D-045 | 4-substituted phenyl | Cl |
| D-046 | 4-substituted phenyl | Br |
| D-047 | 4-substituted phenyl | Me |
| D-048 | 4-substituted phenyl | Et |
| D-049 | 4-substituted phenyl | iPr |
| D-050 | 4-substituted phenyl | cPr |
| D-051 | 4-substituted phenyl | tBu |
| D-052 | 4-substituted phenyl | OMe |

TABLE D-continued

| No. | ring | substituents |
|---|---|---|
| D-053 | 4-substituted phenyl | OEt |
| D-054 | 4-substituted phenyl | OiPr |
| D-055 | 4-substituted phenyl | vinyl |
| D-056 | 4-substituted phenyl | ethynyl |
| D-057 | 4-substituted phenyl | CN |
| D-058 | 4-substituted phenyl | CF$_3$ |
| D-059 | 4-substituted phenyl | OCF$_3$ |
| D-060 | 4-substituted phenyl | CHF$_2$ |
| D-061 | 4-substituted phenyl | CH$_2$F |
| D-062 | 4-substituted phenyl | OCHF$_2$ |
| D-063 | 4-substituted phenyl | OCH$_2$F |
| D-064 | 3-substituted phenyl | H |
| D-065 | 3-substituted phenyl | F |
| D-066 | 3-substituted phenyl | Cl |
| D-067 | 3-substituted phenyl | Br |
| D-068 | 3-substituted phenyl | Me |
| D-069 | 3-substituted phenyl | Et |
| D-070 | 3-substituted phenyl | iPr |
| D-071 | 3-substituted phenyl | cPr |
| D-072 | 3-substituted phenyl | tBu |
| D-073 | 3-substituted phenyl | OMe |
| D-074 | 3-substituted phenyl | OEt |
| D-075 | 3-substituted phenyl | OiPr |
| D-076 | 3-substituted phenyl | vinyl |
| D-077 | 3-substituted phenyl | ethynyl |
| D-078 | 3-substituted phenyl | CN |
| D-079 | 3-substituted phenyl | CF$_3$ |
| D-080 | 3-substituted phenyl | OCF$_3$ |
| D-081 | 3-substituted phenyl | CHF$_2$ |
| D-082 | 3-substituted phenyl | CH$_2$F |
| D-083 | 3-substituted phenyl | OCHF$_2$ |
| D-084 | 3-substituted phenyl | OCH$_2$F |
| D-085 | 2-substituted phenyl | H |
| D-086 | 2-substituted phenyl | F |
| D-087 | 2-substituted phenyl | Cl |
| D-088 | 2-substituted phenyl | Br |
| D-089 | 2-substituted phenyl | Me |
| D-090 | 2-substituted phenyl | Et |
| D-091 | 2-substituted phenyl | iPr |
| D-092 | 2-substituted phenyl | cPr |
| D-093 | 2-substituted phenyl | tBu |
| D-094 | 2-substituted phenyl | OMe |
| D-095 | 2-substituted phenyl | OEt |
| D-096 | 2-substituted phenyl | OiPr |
| D-097 | 2-substituted phenyl | vinyl |
| D-098 | 2-substituted phenyl | ethynyl |
| D-099 | 2-substituted phenyl | CN |
| D-100 | 2-substituted phenyl | CF$_3$ |
| D-101 | 2-substituted phenyl | OCF$_3$ |
| D-102 | 2-substituted phenyl | CHF$_2$ |
| D-103 | 2-substituted phenyl | CH$_2$F |
| D-104 | 2-substituted phenyl | OCHF$_2$ |
| D-105 | 2-substituted phenyl | OCH$_2$F |
| D-106 | 2,4-disubstituted phenyl | F, F |
| D-107 | 2,4-disubstituted phenyl | Cl, Cl |
| D-108 | 2,4-disubstituted phenyl | Br, Br |
| D-109 | 2,4-disubstituted phenyl | Me, Me |
| D-110 | 2,4-disubstituted phenyl | Et, Et |
| D-111 | 2,4-disubstituted phenyl | iPr, iPr |
| D-112 | 2,4-disubstituted phenyl | cPr, cPr |
| D-113 | 2,4-disubstituted phenyl | OMe, OMe |
| D-114 | 2,4-disubstituted phenyl | OEt, OEt |
| D-115 | 2,4-disubstituted phenyl | CF$_3$, CF$_3$ |
| D-116 | 2,4-disubstituted phenyl | OCF$_3$, OCF$_3$ |
| D-117 | 3,5-disubstituted phenyl | F, F |
| D-118 | 3,5-disubstituted phenyl | Cl, Cl |
| D-119 | 3,5-disubstituted phenyl | Br, Br |
| D-120 | 3,5-disubstituted phenyl | Me, Me |
| D-121 | 3,5-disubstituted phenyl | Et, Et |
| D-122 | 3,5-disubstituted phenyl | iPr, iPr |
| D-123 | 3,5-disubstituted phenyl | cPr, cPr |
| D-124 | 3,5-disubstituted phenyl | OMe, OMe |
| D-125 | 3,5-disubstituted phenyl | OEt, OEt |
| D-126 | 3,5-disubstituted phenyl | CF$_3$, CF$_3$ |
| D-127 | 3,5-disubstituted phenyl | OCF$_3$, OCF$_3$ |
| D-128 | 2,6-disubstituted phenyl | F, F |
| D-129 | 2,6-disubstituted phenyl | Cl, Cl |
| D-130 | 2,6-disubstituted phenyl | Br, Br |
| D-131 | 2,6-disubstituted phenyl | Me, Me |
| D-132 | 2,6-disubstituted phenyl | Et, Et |
| D-133 | 2,6-disubstituted phenyl | iPr, iPr |
| D-134 | 2,6-disubstituted phenyl | cPr, cPr |
| D-135 | 2,6-disubstituted phenyl | OMe, OMe |
| D-136 | 2,6-disubstituted phenyl | OEt, OEt |
| D-137 | 2,6-disubstituted phenyl | CF$_3$, CF$_3$ |
| D-138 | 2,6-disubstituted phenyl | OCF$_3$, OCF$_3$ |
| D-139 | 2,3-disubstituted phenyl | F, F |
| D-140 | 2,3-disubstituted phenyl | Cl, Cl |
| D-141 | 2,3-disubstituted phenyl | Br, Br |
| D-142 | 2,3-disubstituted phenyl | Me, Me |
| D-143 | 2,3-disubstituted phenyl | Et, Et |
| D-144 | 2,3-disubstituted phenyl | iPr, iPr |
| D-145 | 2,3-disubstituted phenyl | cPr, cPr |
| D-146 | 2,3-disubstituted phenyl | OMe, OMe |
| D-147 | 2,3-disubstituted phenyl | OEt, OEt |
| D-148 | 2,3-disubstituted phenyl | CF$_3$, CF$_3$ |
| D-149 | 2,3-disubstituted phenyl | OCF$_3$, OCF$_3$ |
| D-150 | 2,5-disubstituted phenyl | F, F |
| D-151 | 2,5-disubstituted phenyl | Cl, Cl |
| D-152 | 2,5-disubstituted phenyl | Br, Br |
| D-153 | 2,5-disubstituted phenyl | Me, Me |
| D-154 | 2,5-disubstituted phenyl | Et, Et |
| D-155 | 2,5-disubstituted phenyl | iPr, iPr |
| D-156 | 2,5-disubstituted phenyl | cPr, cPr |
| D-157 | 2,5-disubstituted phenyl | OMe, OMe |
| D-158 | 2,5-disubstituted phenyl | OEt, OEt |
| D-159 | 2,5-disubstituted phenyl | CF$_3$, CF$_3$ |
| D-160 | 2,5-disubstituted phenyl | OCF$_3$, OCF$_3$ |
| D-161 | 3,4-disubstituted phenyl | F, F |
| D-162 | 3,4-disubstituted phenyl | Cl, Cl |
| D-163 | 3,4-disubstituted phenyl | Br, Br |
| D-164 | 3,4-disubstituted phenyl | Me, Me |
| D-165 | 3,4-disubstituted phenyl | Et, Et |
| D-166 | 3,4-disubstituted phenyl | iPr, iPr |
| D-167 | 3,4-disubstituted phenyl | cPr, cPr |
| D-168 | 3,4-disubstituted phenyl | OMe, OMe |
| D-169 | 3,4-disubstituted phenyl | OEt, OEt |
| D-170 | 3,4-disubstituted phenyl | CF$_3$, CF$_3$ |
| D-171 | 3,4-disubstituted phenyl | OCF$_3$, OCF$_3$ |
| D-172 | 3,5-disubstituted phenyl | F, Cl |
| D-173 | 3,5-disubstituted phenyl | F, Me |
| D-174 | 3,5-disubstituted phenyl | Cl, Me |
| D-175 | 3,5-disubstituted phenyl | CF$_3$, Cl |
| D-176 | 3,5-disubstituted phenyl | CF$_3$, Me |
| D-177 | 3,5-disubstituted phenyl | CF$_3$, CN |
| D-178 | 3,5-disubstituted phenyl | CN, F |
| D-179 | 3,5-disubstituted phenyl | CN, Cl |
| D-180 | 3,5-disubstituted phenyl | CN, Me |
| D-181 | 3,5-disubstituted phenyl | ethynyl, F |
| D-182 | 3,5-disubstituted phenyl | ethynyl, Cl |
| D-183 | 3,5-disubstituted phenyl | ethynyl, Me |
| D-184 | 3,5-disubstituted phenyl | ethynyl, CF$_3$ |
| D-185 | 3,5-disubstituted phenyl | OCF$_3$, F |
| D-186 | 3,5-disubstituted phenyl | OCF$_3$, Cl |
| D-187 | 3,5-disubstituted phenyl | OCF$_3$, Me |
| D-188 | 3,5-disubstituted phenyl | OCF$_3$, ethynyl |
| D-189 | 2,3-disubstituted phenyl | 2-F, 3-Cl |
| D-190 | 2,3-disubstituted phenyl | 2-F, 3-Me |
| D-191 | 2,3-disubstituted phenyl | 2-Cl, 3-Me |
| D-192 | 2,3-disubstituted phenyl | 2-CF$_3$, 3-F |
| D-193 | 2,3-disubstituted phenyl | 2-CF$_3$, 3-Cl |
| D-194 | 2,3-disubstituted phenyl | 2-CF$_3$, 3-Me |
| D-195 | 2,3-disubstituted phenyl | 2-CN, 3-F |
| D-196 | 2,3-disubstituted phenyl | 2-CN, 3-Cl |
| D-197 | 2,3-disubstituted phenyl | 2-ethynyl, 3-F |
| D-198 | 2,3-disubstituted phenyl | 2-ethynyl, 3-Cl |
| D-199 | 2,3-disubstituted phenyl | 2-ethynyl, 3-Me |
| D-200 | 2,3-disubstituted phenyl | 2-ethynyl, 3-CF$_3$ |
| D-201 | 2,3-disubstituted phenyl | 2-OCF$_3$, 3-F |
| D-202 | 2,3-disubstituted phenyl | 2-OCF$_3$, 3-Cl |
| D-203 | 2,3-disubstituted phenyl | 2-OCF$_3$, 3-Me |
| D-204 | 2,3-disubstituted phenyl | 2-OCF$_3$, 3-ethynyl |
| D-205 | 3,2-disubstituted phenyl | 3-F, 2-Cl |
| D-206 | 3,2-disubstituted phenyl | 3-F, 2-Me |
| D-207 | 3,2-disubstituted phenyl | 3-Cl, 2-Me |

TABLE D-continued

| No. | ring | substituents |
|---|---|---|
| D-208 | 3,2-disubstituted phenyl | 3-$CF_3$, 2-F |
| D-209 | 3,2-disubstituted phenyl | 3-$CF_3$, 2-Cl |
| D-210 | 3,2-disubstituted phenyl | 3-$CF_3$, 2-Me |
| D-211 | 3,2-disubstituted phenyl | 3-CN, 2-F |
| D-212 | 3,2-disubstituted phenyl | 3-CN, 2-Cl |
| D-213 | 3,2-disubstituted phenyl | 3-ethynyl, 2-F |
| D-214 | 3,2-disubstituted phenyl | 3-ethynyl, 2-Cl |
| D-215 | 3,2-disubstituted phenyl | 3-ethynyl, 2-Me |
| D-216 | 3,2-disubstituted phenyl | 3-ethynyl, 2-$CF_3$ |
| D-217 | 3,2-disubstituted phenyl | 3-$OCF_3$, 2-F |
| D-218 | 3,2-disubstituted phenyl | 3-$OCF_3$, 2-Cl |
| D-219 | 3,2-disubstituted phenyl | 3-$OCF_3$, 2-Me |
| D-220 | 3,2-disubstituted phenyl | 3-$OCF_3$, 2-ethynyl |
| D-221 | 2,4-disubstituted phenyl | 2-F, 4-Cl |
| D-222 | 2,4-disubstituted phenyl | 2-F, 4-Me |
| D-223 | 2,4-disubstituted phenyl | 2-Cl, 4-Me |
| D-224 | 2,4-disubstituted phenyl | 2-$CF_3$, 4-F |
| D-225 | 2,4-disubstituted phenyl | 2-$CF_3$, 4-Cl |
| D-226 | 2,4-disubstituted phenyl | 2-$CF_3$, 4-Me |
| D-227 | 2,4-disubstituted phenyl | 2-CN, 4-F |
| D-228 | 2,4-disubstituted phenyl | 2-CN, 4-Cl |
| D-229 | 2,4-disubstituted phenyl | 2-ethynyl, 4-F |
| D-230 | 2,4-disubstituted phenyl | 2-ethynyl, 4-Cl |
| D-231 | 2,4-disubstituted phenyl | 2-ethynyl, 4-Me |
| D-232 | 2,4-disubstituted phenyl | 2-ethynyl, 4-$CF_3$ |
| D-233 | 2,4-disubstituted phenyl | 2-$OCF_3$, 4-F |
| D-234 | 2,4-disubstituted phenyl | 2-$OCF_3$, 4-Cl |
| D-235 | 2,4-disubstituted phenyl | 2-$OCF_3$, 4-Me |
| D-236 | 2,4-disubstituted phenyl | 2-$OCF_3$, 4-ethynyl |
| D-237 | 4,2-disubstituted phenyl | 4-F, 2-Cl |
| D-238 | 4,2-disubstituted phenyl | 4-F, 2-Me |
| D-239 | 4,2-disubstituted phenyl | 4-Cl, 2-Me |
| D-240 | 4,2-disubstituted phenyl | 4-$CF_3$, 2-F |
| D-241 | 4,2-disubstituted phenyl | 4-$CF_3$, 2-Cl |
| D-242 | 4,2-disubstituted phenyl | 4-$CF_3$, 2-Me |
| D-243 | 4,2-disubstituted phenyl | 4-CN, 2-F |
| D-244 | 4,2-disubstituted phenyl | 4-CN, 2-Cl |
| D-245 | 4,2-disubstituted phenyl | 4-ethynyl, 2-F |
| D-246 | 4,2-disubstituted phenyl | 4-ethynyl, 2-Cl |
| D-247 | 4,2-disubstituted phenyl | 4-ethynyl, 2-Me |
| D-248 | 4,2-disubstituted phenyl | 4-ethynyl, 2-$CF_3$ |
| D-249 | 4,2-disubstituted phenyl | 4-$OCF_3$, 2-F |
| D-250 | 4,2-disubstituted phenyl | 4-$OCF_3$, 2-Cl |
| D-251 | 4,2-disubstituted phenyl | 4-$OCF_3$, 2-Me |
| D-252 | 4,2-disubstituted phenyl | 4-$OCF_3$, 2-ethynyl |
| D-253 | 2,5-disubstituted phenyl | 2-F, 5-Cl |
| D-254 | 2,5-disubstituted phenyl | 2-F, 5-Me |
| D-255 | 2,5-disubstituted phenyl | 2-Cl, 5-Me |
| D-256 | 2,5-disubstituted phenyl | 2-$CF_3$, 5-F |
| D-257 | 2,5-disubstituted phenyl | 2-$CF_3$, 5-Cl |
| D-258 | 2,5-disubstituted phenyl | 2-$CF_3$, 5-Me |
| D-259 | 2,5-disubstituted phenyl | 2-CN, 5-F |
| D-260 | 2,5-disubstituted phenyl | 2-CN, 5-Cl |
| D-261 | 2,5-disubstituted phenyl | 2-ethynyl, 5-F |
| D-262 | 2,5-disubstituted phenyl | 2-ethynyl, 5-Cl |
| D-263 | 2,5-disubstituted phenyl | 2-ethynyl, 5-Me |
| D-264 | 2,5-disubstituted phenyl | 2-ethynyl, 5-$CF_3$ |
| D-265 | 2,5-disubstituted phenyl | 2-$OCF_3$, 5-F |
| D-266 | 2,5-disubstituted phenyl | 2-$OCF_3$, 5-Cl |
| D-267 | 2,5-disubstituted phenyl | 2-$OCF_3$, 5-Me |
| D-268 | 2,5-disubstituted phenyl | 2-$OCF_3$, 5-ethynyl |
| D-269 | 5,2-disubstituted phenyl | 5-F, 2-Cl |
| D-270 | 5,2-disubstituted phenyl | 5-F, 2-Me |
| D-271 | 5,2-disubstituted phenyl | 5-Cl, 2-Me |
| D-272 | 5,2-disubstituted phenyl | 5-$CF_3$, 2-F |
| D-273 | 5,2-disubstituted phenyl | 5-$CF_3$, 2-Cl |
| D-274 | 5,2-disubstituted phenyl | 5-$CF_3$, 2-Me |
| D-275 | 5,2-disubstituted phenyl | 5-CN, 2-F |
| D-276 | 5,2-disubstituted phenyl | 5-CN, 2-Cl |
| D-277 | 5,2-disubstituted phenyl | 5-ethynyl, 2-F |
| D-278 | 5,2-disubstituted phenyl | 5-ethynyl, 2-Cl |
| D-279 | 5,2-disubstituted phenyl | 5-ethynyl, 2-Me |
| D-280 | 5,2-disubstituted phenyl | 5-ethynyl, 2-$CF_3$ |
| D-281 | 5,2-disubstituted phenyl | 5-$OCF_3$, 2-F |
| D-282 | 5,2-disubstituted phenyl | 5-$OCF_3$, 2-Cl |
| D-283 | 5,2-disubstituted phenyl | 5-$OCF_3$, 2-Me |
| D-284 | 5,2-disubstituted phenyl | 5-$OCF_3$, 2-ethynyl |
| D-285 | 3,4-disubstituted phenyl | 3-F, 4-Cl |
| D-286 | 3,4-disubstituted phenyl | 3-F, 4-Me |
| D-287 | 3,4-disubstituted phenyl | 3-Cl, 4-Me |
| D-288 | 3,4-disubstituted phenyl | 3-$CF_3$, 4-F |
| D-289 | 3,4-disubstituted phenyl | 3-$CF_3$, 4-Cl |
| D-290 | 3,4-disubstituted phenyl | 3-$CF_3$, 4-Me |
| D-291 | 3,4-disubstituted phenyl | 3-CN, 4-F |
| D-292 | 3,4-disubstituted phenyl | 3-CN, 4-Cl |
| D-293 | 3,4-disubstituted phenyl | 3-ethynyl, 4-F |
| D-294 | 3,4-disubstituted phenyl | 3-ethynyl, 4-Cl |
| D-295 | 3,4-disubstituted phenyl | 3-ethynyl, 4-Me |
| D-296 | 3,4-disubstituted phenyl | 3-ethynyl, 4-$CF_3$ |
| D-297 | 3,4-disubstituted phenyl | 3-$OCF_3$, 4-F |
| D-298 | 3,4-disubstituted phenyl | 3-$OCF_3$, 4-Cl |
| D-299 | 3,4-disubstituted phenyl | 3-$OCF_3$, 4-Me |
| D-300 | 3,4-disubstituted phenyl | 3-$OCF_3$, 4-ethynyl |
| D-301 | 4,3-disubstituted phenyl | 4-F, 3-Cl |
| D-302 | 4,3-disubstituted phenyl | 4-F, 3-Me |
| D-303 | 4,3-disubstituted phenyl | 4-Cl, 3-Me |
| D-304 | 4,3-disubstituted phenyl | 4-$CF_3$, 3-F |
| D-305 | 4,3-disubstituted phenyl | 4-$CF_3$, 3-Cl |
| D-306 | 4,3-disubstituted phenyl | 4-$CF_3$, 3-Me |
| D-307 | 4,3-disubstituted phenyl | 4-CN, 3-F |
| D-308 | 4,3-disubstituted phenyl | 4-CN, 3-Cl |
| D-309 | 4,3-disubstituted phenyl | 4-ethynyl, 3-F |
| D-310 | 4,3-disubstituted phenyl | 4-ethynyl, 3-Cl |
| D-311 | 4,3-disubstituted phenyl | 4-ethynyl, 3-Me |
| D-312 | 4,3-disubstituted phenyl | 4-ethynyl, 3-$CF_3$ |
| D-313 | 4,3-disubstituted phenyl | 4-$OCF_3$, 3-F |
| D-314 | 4,3-disubstituted phenyl | 4-$OCF_3$, 3-Cl |
| D-315 | 4,3-disubstituted phenyl | 4-$OCF_3$, 3-Me |
| D-316 | 4,3-disubstituted phenyl | 4-$OCF_3$, 3-ethynyl |

In further other embodiments of the invention, the methods and uses comprise compounds of formula (I) identified below.

Table 1d: Compounds of formulae (Ia-1), (Ia-2) and (Ia-3), wherein Q is as defined in entry D-001 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-001 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-001 of table D and p, $R^1$, $R^3$, $R^{5a}$ and $R^{5b}$ correspond in each case to a row of table C.

Table 2d: Compounds of formulae (Ia-1), (Ia-2) and (Ia-3), wherein Q is as defined in entry D-002 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-002 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-002 of table D and p, $R^1$, $R^3$, $R^{5a}$ and $R^{5b}$ correspond in each case to a row of table C.

Table 3d: Compounds of formulae (Ia-1), (Ia-2) and (Ia-3), wherein Q is as defined in entry D-003 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-003 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-003 of table D and p, $R^1$, $R^3$, $R^{5a}$ and $R^{5b}$ correspond in each case to a row of table C.

Table 4d: Compounds of formulae (Ia-1), (Ia-2) and (Ia-3), wherein Q is as defined in entry D-004 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-004 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-004 of table D and p, $R^1$, $R^3$, $R^{5a}$ and $R^{5b}$ correspond in each case to a row of table C.

Table 5d: Compounds of formulae (Ia-1), (Ia-2) and (Ia-3), wherein Q is as defined in entry D-005 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-005 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-005 of table D and p, $R^3$, $R^{5a}$ and $R^{5b}$ correspond in each case to a row of table C.

Table 6d: Compounds of formulae (Ia-1), (Ia-2) and (Ia-3), wherein Q is as defined in entry D-6 of table D and p, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-6 of table D and p, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-6 of table D and p, $R^3$, $R^{5a}$ and $R^{5b}$ correspond in each case to a row of table C.

Table 7d: Compounds of formulae (Ia-1), (Ia-2) and (Ia-3), wherein Q is as defined in entry D-7 of table D and p, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-7 of table D and p, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-7 of table D and p, $R^3$, $R^{5a}$ and $R^{5b}$ correspond in each case to a row of table C.

Table 8d: Compounds of formulae (Ia-1), (Ia-2) and (Ia-3), wherein Q is as defined in entry D-8 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-8 of table D and p, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-8 of table D and p, $R^3$, $R^{5a}$ and $R^{5b}$ correspond in each case to a row of table C.

Table 9d: Compounds of formulae (Ia-1), (Ia-2) and (Ia-3), wherein Q is as defined in entry D-9 of table D and p, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-9 of table D and p, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-9 of table D and p, $R^3$, $R^{5a}$ and $R^{5b}$ correspond in each case to a row of table C.

Table 10d: Compounds of formulae (Ia-1), (Ia-2) and (Ia-3), wherein Q is as defined in entry D-10 of table D and p, R1, R3 and R5 correspond in each case to a row of table A; compound of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-10 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-10 of table D and p, $R^1$, $R^3$, $R^{5a}$ and $R^{5b}$ correspond in each case to a row of table C.

Table 11d: Compounds of formulae (Ia-1), (Ia-2) and (Ia-3), wherein Q is as defined in entry D-11 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-11 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-11 of table D and p, $R^1$, $R^3$, $R^{5a}$ and $R^{5b}$ correspond in each case to a row of table C.

Table 12d: Compounds of formulae (Ia-1), (Ia-2) and (Ia-3), wherein Q is as defined in entry D-12 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-12 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-12 of table D and p, $R^1$, $R^3$, $R^{5a}$ and $R^{5b}$ correspond in each case to a row of table C.

Table 13d: Compounds of formulae (Ia-1), (Ia-2) and (Ia-3), wherein Q is as defined in entry D-13 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-13 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-13 of table D and p, $R^1$, $R^3$, $R^{5a}$ and $R^{5b}$ correspond in each case to a row of table C.

Table 14d: Compounds of formulae (Ia-1), (Ia-2) and (Ia-3), wherein Q is as defined in entry D-14 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-14 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-14 of table D and p, $R^1$, $R^3$, $R^{5a}$ and $R^{5b}$ correspond in each case to a row of table C.

Table 15d: Compounds of formulae (Ia-1), (Ia-2) and (Ia-3), wherein Q is as defined in entry D-15 of table D and p, $R^1$, $R^3$ and $R^5$ correspond in each case to a row of table A; 10), (Ib-11) and (Ib-12), wherein Q is as defined in entry D-15 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-15 of table D and p, $R^1$, $R^3$, $R^{5a}$ and $R^{5b}$ correspond in each case to a row of table C.

Table 16d: Compounds of formulae (Ia-1), (Ia-2) and (Ia-3), wherein Q is as defined in entry D-16 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-16 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-16 of table D and p, $R^1$, $R^3$, $R^{5a}$ and $R^{5b}$ correspond in each case to a row of table C.

Table 17d: Compounds of formulae (Ia-1), (Ia-2) and (Ia-3), wherein Q is as defined in entry D-17 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-17 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-17 of table D and p, $R^1$, $R^3$, $R^{5a}$ and $R^{5b}$ correspond in each case to a row of table C.

Table 18d: Compounds of formulae (Ia-1), (Ia-2) and (Ia-3), wherein Q is as defined in entry D-18 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-18 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-18 of table D and p, $R^1$, $R^3$, $R^{5a}$ and $R^{5b}$ correspond in each case to a row of table C.

Table 19d: Compounds of formulae (Ia-1), (Ia-2) and (Ia-3), wherein Q is as defined in entry D-19 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-19 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-19 of table D and p, $R^1$, $R^3$, $R^{5a}$ and $R^{5b}$ correspond in each case to a row of table C.

Table 20d: Compounds of formulae (Ia-1), (Ia-2) and (Ia-3), wherein Q is as defined in entry D-20 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-20 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-20 of table D and p, $R^1$, $R^3$, $R^{5a}$ and $R^{5b}$ correspond in each case to a row of table C.

Table 21d: Compounds of formulae (Ia-1), (Ia-2) and (Ia-3), wherein Q is as defined in entry D-21 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-21 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-21 of table D and p, $R^1$, $R^3$, $R^{5a}$ and $R^{5b}$ correspond in each case to a row of table C.

Table 22d: Compounds of formulae (Ia-1), (Ia-2) and (Ia-3), wherein Q is as defined in entry D-22 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-22 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-22 of table D and p, $R^1$, $R^3$, $R^{5a}$ and $R^{5b}$ correspond in each case to a row of table C.

Table 23d: Compounds of formulae (Ia-1), (Ia-2) and (Ia-3), wherein Q is as defined in entry D-23 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-23 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-23 of table D and p, $R^1$, $R^3$, $R^{5a}$ and $R^{5b}$ correspond in each case to a row of table C.

Table 24d: Compounds of formulae (Ia-1), (Ia-2) and (Ia-3), wherein Q is as defined in entry D-24 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-24 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-24 of table D and p, $R^1$, $R^3$, $R^{5a}$ and $R^{5b}$ correspond in each case to a row of table C.

Table 25d: Compounds of formulae (Ia-1), (Ia-2) and (Ia-3), wherein Q is as defined in entry D-25 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-25 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-25 of table D and p, $R^1$, $R^3$, $R^{5a}$ and $R^{5b}$ correspond in each case to a row of table C.

Table 26d: Compounds of formulae (Ia-1), (Ia-2) and (Ia-3), wherein Q is as defined in entry D-26 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-26 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-26 of table D and p, $R^1$, $R^3$, $R^{5a}$ and $R^{5b}$ correspond in each case to a row of table C.

Table 27d: Compounds of formulae (Ia-1), (Ia-2) and (Ia-3), wherein Q is as defined in entry D-27 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-27 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-27 of table D and p, $R^1$, $R^3$, $R^{5a}$ and $R^{5b}$ correspond in each case to a row of table C.

Table 27d: Compounds of formulae (Ia-1), (Ia-2) and (Ia-3), wherein Q is as defined in entry D-27 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-27 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-27 of table D and p, $R^1$, $R^3$, $R^{5a}$ and $R^{5b}$ correspond in each case to a row of table C.

Table 28d: Compounds of formulae (Ia-1), (Ia-2) and (Ia-3), wherein Q is as defined in entry D-28 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-28 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-28 of table D and p, $R^1$, $R^3$, $R^{5a}$ and $R^{5b}$ correspond in each case to a row of table C.

Table 29d: Compounds of formulae (Ia-1), (Ia-2) and (Ia-3), wherein Q is as defined in entry D-29 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-29 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-29 of table D and p, $R^1$, $R^3$, $R^{5a}$ and $R^{5b}$ correspond in each case to a row of table C.

Table 30d: Compounds of formulae (Ia-1), (Ia-2) and (Ia-3), wherein Q is as defined in entry D-30 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-30 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-30 of table D and p, $R^1$, $R^3$, $R^{5a}$ and $R^{5b}$ correspond in each case to a row of table C.

Table 31d: Compounds of formulae (Ia-1), (Ia-2) and (Ia-3), wherein Q is as defined in entry D-31 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-31 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-31 of table D and p, $R^1$, $R^3$, $R^{5a}$ and $R^{5b}$ correspond in each case to a row of table C.

Table 32d: Compounds of formulae (Ia-1), (Ia-2) and (Ia-3), wherein Q is as defined in entry D-32 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-32 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-32 of table D and p, $R^1$, $R^3$, $R^{5a}$ and $R^{5b}$ correspond in each case to a row of table C.

Table 33d: Compounds of formulae (Ia-1), (Ia-2) and (Ia-3), wherein Q is as defined in entry D-33 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-33 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-33 of table D and p, $R^1$, $R^3$, $R^{5a}$ and $R^{5b}$ correspond in each case to a row of table C.

Table 34d: Compounds of formulae (Ia-1), (Ia-2) and (Ia-3), wherein Q is as defined in entry D-34 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-34 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-34 of table D and p, $R^1$, $R^3$, $R^{5a}$ and $R^{5b}$ correspond in each case to a row of table C.

Table 35d: Compounds of formulae (Ia-1), (Ia-2) and (Ia-3), wherein Q is as defined in entry D-35 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-35 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-35 of table D and p, $R^1$, $R^3$, $R^{5a}$ and $R^{5b}$ correspond in each case to a row of table C.

Table 36d: Compounds of formulae (Ia-1), (Ia-2) and (Ia-3), wherein Q is as defined in entry D-36 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-36 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-36 of table D and p, $R^1$, $R^3$, $R^{5a}$ and $R^{5b}$ correspond in each case to a row of table C.

Table 37d: Compounds of formulae (Ia-1), (Ia-2) and (Ia-3), wherein Q is as defined in entry D-37 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-37 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-37 of table D and p, $R^1$, $R^3$, $R^{5a}$ and $R^{5b}$ correspond in each case to a row of table C.

Table 38d: Compounds of formulae (Ia-1), (Ia-2) and (Ia-3), wherein Q is as defined in entry D-38 of table D and p, $R^1$, $R^3$ and $R^5$ correspond in each case to a row of table A; 10), (Ib-11) and (Ib-12), wherein Q is as defined in entry D-38 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-38 of table D and p, $R^1$, $R^3$, $R^{5a}$ and $R^{5b}$ correspond in each case to a row of table C.

Table 39d: Compounds of formulae (Ia-1), (Ia-2) and (Ia-3), wherein Q is as defined in entry D-39 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-39 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-39 of table D and p, $R^1$, $R^3$, $R^{5a}$ and $R^{5b}$ correspond in each case to a row of table C.

Table 40d: Compounds of formulae (Ia-1), (Ia-2) and (Ia-3), wherein Q is as defined in entry D-40 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-40 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-40 of table D and p, $R^1$, $R^3$, $R^{5a}$ and $R^{5b}$ correspond in each case to a row of table C.

Table 41d: Compounds of formulae (Ia-1), (Ia-2) and (Ia-3), wherein Q is as defined in entry D-41 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-41 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-41 of table D and p, $R^1$, $R^3$, $R^{5a}$ and $R^{5b}$ correspond in each case to a row of table C.

Table 42d: Compounds of formulae (Ia-1), (Ia-2) and (Ia-3), wherein Q is as defined in entry D-42 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-42 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-42 of table D and p, $R^1$, $R^3$, $R^{5a}$ and $R^{5b}$ correspond in each case to a row of table C.

Table 43d: Compounds of formulae (Ia-1), (Ia-2) and (Ia-3), wherein Q is as defined in entry D-43 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-43 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-43 of table D and p, $R^1$, $R^3$, $R^{5a}$ and $R^{5b}$ correspond in each case to a row of table C.

Table 44d: Compounds of formulae (Ia-1), (Ia-2) and (Ia-3), wherein Q is as defined in entry D-44 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-44 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-44 of table D and p, $R^1$, $R^3$, $R^{5a}$ and $R^{5b}$ correspond in each case to a row of table C.

Table 45d: Compounds of formulae (Ia-1), (Ia-2) and (Ia-3), wherein Q is as defined in entry D-45 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-45 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-45 of table D and p, $R^1$, $R^3$, $R^{5a}$ and $R^{5b}$ correspond in each case to a row of table C.

Table 46d: Compounds of formulae (Ia-1), (Ia-2) and (Ia-3), wherein Q is as defined in entry D-46 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-46 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-46 of table D and p, $R^1$, $R^3$, $R^{5a}$ and $R^{5b}$ correspond in each case to a row of table C.

Table 47d: Compounds of formulae (Ia-1), (Ia-2) and (Ia-3), wherein Q is as defined in entry D-47 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-47 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-47 of table D and p, $R^1$, $R^3$, $R^{5a}$ and $R^{5b}$ correspond in each case to a row of table C.

Table 48d: Compounds of formulae (Ia-1), (Ia-2) and (Ia-3), wherein Q is as defined in entry D-48 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-48 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-48 of table D and p, $R^1$, $R^3$, $R^{5a}$ and $R^{5b}$ correspond in each case to a row of table C.

Table 49d: Compounds of formulae (Ia-1), (Ia-2) and (Ia-3), wherein Q is as defined in entry D-49 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-49 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-49 of table D and p, $R^1$, $R^3$, $R^{5a}$ and $R^{5b}$ correspond in each case to a row of table C.

Table 50d: Compounds of formulae (Ia-1), (Ia-2) and (Ia-3), wherein Q is as defined in entry D-50 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-50 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-50 of table D and p, $R^1$, $R^3$, $R^{5a}$ and $R^{5b}$ correspond in each case to a row of table C.

Table 51d: Compounds of formulae (Ia-1), (Ia-2) and (Ia-3), wherein Q is as defined in entry D-51 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-51 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-51 of table D and p, $R^1$, $R^3$, $R^{5a}$ and $R^{5b}$ correspond in each case to a row of table C.

Table 52d: Compounds of formulae (Ia-1), (Ia-2) and (Ia-3), wherein Q is as defined in entry D-52 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-52 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-52 of table D and p, $R^1$, $R^3$, $R^{5a}$ and $R^{5b}$ correspond in each case to a row of table C.

Table 53d: Compounds of formulae (Ia-1), (Ia-2) and (Ia-3), wherein Q is as defined in entry D-53 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-53 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-53 of table D and p, $R^1$, $R^3$, $R^{5a}$ and $R^{5b}$ correspond in each case to a row of table C.

Table 54d: Compounds of formulae (Ia-1), (Ia-2) and (Ia-3), wherein Q is as defined in entry D-54 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-54 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-54 of table D and p, $R^1$, $R^3$, $R^{5a}$ and $R^{5b}$ correspond in each case to a row of table C.

Table 55d: Compounds of formulae (Ia-1), (Ia-2) and (Ia-3), wherein Q is as defined in entry D-55 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-55 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-55 of table D and p, $R^1$, $R^3$, $R^{5a}$ and $R^{5b}$ correspond in each case to a row of table C.

Table 56d: Compounds of formulae (Ia-1), (Ia-2) and (Ia-3), wherein Q is as defined in entry D-56 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-56 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-56 of table D and p, $R^1$, $R^3$, $R^{5a}$ and $R^{5b}$ correspond in each case to a row of table C.

Table 57d: Compounds of formulae (Ia-1), (Ia-2) and (Ia-3), wherein Q is as defined in entry D-57 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-57 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-57 of table D and p, $R^1$, $R^3$, $R^{5a}$ and $R^{5b}$ correspond in each case to a row of table C.

Table 58d: Compounds of formulae (Ia-1), (Ia-2) and (Ia-3), wherein Q is as defined in entry D-58 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-58 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-58 of table D and p, $R^1$, $R^3$, $R^{5a}$ and $R^{5b}$ correspond in each case to a row of table C.

Table 59d: Compounds of formulae (Ia-1), (Ia-2) and (Ia-3), wherein Q is as defined in entry D-59 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-59 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-59 of table D and p, $R^1$, $R^3$, $R^{5a}$ and $R^{5b}$ correspond in each case to a row of table C.

Table 60d: Compounds of formulae (Ia-1), (Ia-2) and (Ia-3), wherein Q is as defined in entry D-60 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-60 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-60 of table D and p, $R^1$, $R^3$, $R^{5a}$ and $R^{5b}$ correspond in each case to a row of table C.

Table 61d: Compounds of formulae (Ia-1), (Ia-2) and (Ia-3), wherein Q is as defined in entry D-61 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-61 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-61 of table D and p, $R^1$, $R^3$, $R^{5a}$ and $R^{5b}$ correspond in each case to a row of table C.

Table 62d: Compounds of formulae (Ia-1), (Ia-2) and (Ia-3), wherein Q is as defined in entry D-62 of table D and p, $R^1$, $R^3$ and $R^5$ correspond in each case to a row of table A; 10), (Ib-11) and (Ib-12), wherein Q is as defined in entry D-62 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-62 of table D and p, $R^1$, $R^3$, $R^{5a}$ and $R^{5b}$ correspond in each case to a row of table C.

Table 63d: Compounds of formulae (Ia-1), (Ia-2) and (Ia-3), wherein Q is as defined in entry D-63 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-63 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-63 of table D and p, $R^1$, $R^3$, $R^{5a}$ and $R^{5b}$ correspond in each case to a row of table C.

Table 64d: Compounds of formulae (Ia-1), (Ia-2) and (Ia-3), wherein Q is as defined in entry D-64 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-64 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-64 of table D and p, $R^1$, $R^3$, $R^{5a}$ and $R^{5b}$ correspond in each case to a row of table C.

Table 65d: Compounds of formulae (Ia-1), (Ia-2) and (Ia-3), wherein Q is as defined in entry D-65 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-65 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-65 of table D and p, $R^1$, $R^3$, $R^{5a}$ and $R^{5b}$ correspond in each case to a row of table C.

Table 66d: Compounds of formulae (Ia-1), (Ia-2) and (Ia-3), wherein Q is as defined in entry D-66 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-66 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-66 of table D and p, $R^1$, $R^3$, $R^{5a}$ and $R^{5b}$ correspond in each case to a row of table C.

Table 67d: Compounds of formulae (Ia-1), (Ia-2) and (Ia-3), wherein Q is as defined in entry D-67 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-67 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-67 of table D and p, $R^1$, $R^3$, $R^{5a}$ and $R^{5b}$ correspond in each case to a row of table C.

Table 68d: Compounds of formulae (Ia-1), (Ia-2) and (Ia-3), wherein Q is as defined in entry D-68 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-68 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-68 of table D and p, $R^1$, $R^3$, $R^{5a}$ and $R^{5b}$ correspond in each case to a row of table C.

Table 69d: Compounds of formulae (Ia-1), (Ia-2) and (Ia-3), wherein Q is as defined in entry D-69 of table D and p, $R^1$, $R^3$ and $R^5$ correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-69 of table D and p, $R^1$, $R^3$ and $R^5$ correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-69 of table D and p, R1, R3, R5a and R5b correspond in each case to a row of table C.

Table 70d: Compounds of formulae (Ia-1), (Ia-2) and (Ia-3), wherein Q is as defined in entry D-70 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-70 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-70 of table D and p, R1, R3, R5a and R5b correspond in each case to a row of table C.

Table 71d: Compounds of formulae (Ia-1), (Ia-2) and (Ia-3), wherein Q is as defined in entry D-71 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-71 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-71 of table D and p, R1, R3, R5a and R5b correspond in each case to a row of table C.

Table 72d: Compounds of formulae (Ia-1), (Ia-2) and (Ia-3), wherein Q is as defined in entry D-72 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-72 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-72 of table D and p, R1, R3, R5a and R5b correspond in each case to a row of table C.

Table 73d: Compounds of formulae (Ia-1), (Ia-2) and (Ia-3), wherein Q is as defined in entry D-73 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-73 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-73 of table D and p, R1, R3, R5a and R5b correspond in each case to a row of table C.

Table 74d: Compounds of formulae (Ia-1), (Ia-2) and (Ia-3), wherein Q is as defined in entry D-74 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-74 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-74 of table D and p, R1, R3, R5a and R5b correspond in each case to a row of table C.

Table 75d: Compounds of formulae (Ia-1), (Ia-2) and (Ia-3), wherein Q is as defined in entry D-75 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-75 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-75 of table D and p, R1, R3, R5a and R5b correspond in each case to a row of table C.

Table 76d: Compounds of formulae (Ia-1), (Ia-2) and (Ia-3), wherein Q is as defined in entry D-76 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-76 of table D and p, R1, R3 and (Ic-3), (Ic-4), (Ic-5), (Ic-6), (Ic-7), (Ic-8) and (Ic-9), wherein Q is as defined in entry D-76 of table D and p, R1, R3, R5a and R5b correspond in each case to a row of table C.

Table 77d: Compounds of formulae (Ia-1), (Ia-2) and (Ia-3), wherein Q is as defined in entry D-77 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-77 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-77 of table D and p, R1, R3, R5a and R5b correspond in each case to a row of table C.

Table 78d: Compounds of formulae (Ia-1), (Ia-2) and (Ia-3), wherein Q is as defined in entry D-78 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-78 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-78 of table D and p, R1, R3, R5a and R5b correspond in each case to a row of table C.

Table 79d: Compounds of formulae (Ia-1), (Ia-2) and (Ia-3), wherein Q is as defined in entry D-79 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-79 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-79 of table D and p, R1, R3, R5a and R5b correspond in each case to a row of table C.

Table 80d: Compounds of formulae (Ia-1), (Ia-2) and (Ia-3), wherein Q is as defined in entry D-80 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-80 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-80 of table D and p, R1, R3, R5a and R5b correspond in each case to a row of table C.

Table 81d: Compounds of formulae (Ia-1), (Ia-2) and (Ia-3), wherein Q is as defined in entry D-81 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-81 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-81 of table D and p, R1, R3, R5a and R5b correspond in each case to a row of table C.

Table 82d: Compounds of formulae (Ia-1), (Ia-2) and (Ia-3), wherein Q is as defined in entry D-82 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-82 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-82 of table D and p, R1, R3, R5a and R5b correspond in each case to a row of table C.

Table 83d: Compounds of formulae (Ia-1), (Ia-2) and (Ia-3), wherein Q is as defined in entry D-83 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-83 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-83 of table D and p, R1, R3, R5a and R5b correspond in each case to a row of table C.

Table 84d: Compounds of formulae (Ia-1), (Ia-2) and (Ia-3), wherein Q is as defined in entry D-84 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-84 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-84 of table D and p, R1, R3, R5a and R5b correspond in each case to a row of table C.

Table 85d: Compounds of formulae (Ia-1), (Ia-2) and (Ia-3), wherein Q is as defined in entry D-85 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-85 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-85 of table D and p, R1, R3, R5a and R5b correspond in each case to a row of table C.

Table 86d: Compounds of formulae (Ia-1), (Ia-2) and (Ia-3), wherein Q is as defined in entry D-86 of table D and p, R1, R3 and R5 correspond in each case to a row of table A; 10), (Ib-11) and (Ib-12), wherein Q is as defined in entry D-86 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-86 of table D and p, R1, R3, R5a and R5b correspond in each case to a row of table C.

Table 87d: Compounds of formulae (Ia-1), (Ia-2) and (Ia-3), wherein Q is as defined in entry D-87 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-87 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-87 of table D and p, R1, R3, R5a and R5b correspond in each case to a row of table C.

Table 88d: Compounds of formulae (Ia-1), (Ia-2) and (Ia-3), wherein Q is as defined in entry D-88 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-88 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-88 of table D and p, R1, R3, R5a and R5b correspond in each case to a row of table C.

Table 89d: Compounds of formulae (Ia-1), (Ia-2) and (Ia-3), wherein Q is as defined in entry D-89 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-89 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-89 of table D and p, R1, R3, R5a and R5b correspond in each case to a row of table C.

Table 90d: Compounds of formulae (Ia-1), (Ia-2) and (Ia-3), wherein Q is as defined in entry D-90 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-90 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-90 of table D and p, R1, R3, R5a and R5b correspond in each case to a row of table C.

Table 91d: Compounds of formulae (Ia-1), (Ia-2) and (Ia-3), wherein Q is as defined in entry D-91 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-91 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-91 of table D and p, R1, R3, R5a and R5b correspond in each case to a row of table C.

Table 92d: Compounds of formulae (Ia-1), (Ia-2) and (Ia-3), wherein Q is as defined in entry D-92 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-92 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-92 of table D and p, R1, R3, R5a and R5b correspond in each case to a row of table C.

Table 93: Compounds of formulae (Ia-1), (Ia-2) and (Ia-3), wherein Q is as defined in entry D-93 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-93 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-93 of table D and p, R1, R3, R5a and R5b correspond in each case to a row of table C.

Table 94d: Compounds of formulae (Ia-1), (Ia-2) and (Ia-3), wherein Q is as defined in entry D-94 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-94 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-94 of table D and p, R1, R3, R5a and R5b correspond in each case to a row of table C.

Table 95d: Compounds of formulae (Ia-1), (Ia-2) and (Ia-3), wherein Q is as defined in entry D-95 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-95 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-95 of table D and p, R1, R3, R5a and R5b correspond in each case to a row of table C.

Table 96d: Compounds of formulae (Ia-1), (Ia-2) and (Ia-3), wherein Q is as defined in entry D-96 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-96 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-96 of table D and p, R1, R3, R5a and R5b correspond in each case to a row of table C.

Table 97d: Compounds of formulae (Ia-1), (Ia-2) and (Ia-3), wherein Q is as defined in entry D-97 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-97 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-97 of table D and p, R1, R3, R5a and R5b correspond in each case to a row of table C.

Table 98d: Compounds of formulae (Ia-1), (Ia-2) and (Ia-3), wherein Q is as defined in entry D-98 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-98 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-98 of table D and p, R1, R3, R5a and R5b correspond in each case to a row of table C.

Table 99d: Compounds of formulae (Ia-1), (Ia-2) and (Ia-3), wherein Q is as defined in entry D-99 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-99 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-99 of table D and p, R1, R3, R5a and R5b correspond in each case to a row of table C.

Table 100d: Compounds of formulae (Ia-1), (Ia-2) and (Ia-3), wherein Q is as defined in entry D-100 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-100 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-100 of table D and p, R1, R3, R5a and R5b correspond in each case to a row of table C.

Table 101d: Compounds of formulae (Ia-1), (Ia-2) and (Ia-3), wherein Q is as defined in entry D-101 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-101 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-101 of table D and p, R1, R3, R5a and R5b correspond in each case to a row of table C.

Table 102d: Compounds of formulae (Ia-1), (Ia-2) and (Ia-3), wherein Q is as defined in entry D-102 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-102 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-102 of table D and p, R1, R3, R5a and R5b correspond in each case to a row of table C.

Table 103d: Compounds of formulae (Ia-1), (Ia-2) and (Ia-3), wherein Q is as defined in entry D-103 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-103 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-103 of table D and p, R1, R3, R5a and R5b correspond in each case to a row of table C.

Table 104d: Compounds of formulae (Ia-1), (Ia-2) and (Ia-3), wherein Q is as defined in entry D-104 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-104 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-104 of table D and p, R1, R3, R5a and R5b correspond in each case to a row of table C.

Table 105d: Compounds of formulae (Ia-1), (Ia-2) and (Ia-3), wherein Q is as defined in entry D-105 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-105 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-105 of table D and p, R1, R3, R5a and R5b correspond in each case to a row of table C.

Table 106d: Compounds of formulae (Ia-1), (Ia-2) and (Ia-3), wherein Q is as defined in entry D-106 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-106 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-106 of table D and p, R1, R3, R5a and R5b correspond in each case to a row of table C.

Table 107d: Compounds of formulae (Ia-1), (Ia-2) and (Ia-3), wherein Q is as defined in entry D-107 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-107 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-107 of table D and p, R1, R3, R5a and R5b correspond in each case to a row of table C.

Table 108d: Compounds of formulae (Ia-1), (Ia-2) and (Ia-3), wherein Q is as defined in entry D-108 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-108 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-108 of table D and p, R1, R3, R5a and R5b correspond in each case to a row of table C.

Table 109d: Compounds of formulae (Ia-1), (Ia-2) and (Ia-3), wherein Q is as defined in entry D-109 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-109 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-109 of table D and p, R1, R3, R5a and R5b correspond in each case to a row of table C.

Table 110d: Compounds of formulae (Ia-1), (Ia-2) and (Ia-3), wherein Q is as defined in entry D-110 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-110 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-110 of table D and p, R1, R3, R5a and R5b correspond in each case to a row of table C.

Table 111d: Compounds of formulae (Ia-1), (Ia-2) and (Ia-3), wherein Q is as defined in entry D-111 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-111 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-111 of table D and p, R1, R3, R5a and R5b correspond in each case to a row of table C.

Table 112d: Compounds of formulae (Ia-1), (Ia-2) and (Ia-3), wherein Q is as defined in entry D-112 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-112 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-112 of table D and p, R1, R3, R5a and R5b correspond in each case to a row of table C.

Table 113d: Compounds of formulae (Ia-1), (Ia-2) and (Ia-3), wherein Q is as defined in entry D-113 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-113 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-113 of table D and p, R1, R3, R5a and R5b correspond in each case to a row of table C.

Table 114d: Compounds of formulae (Ia-1), (Ia-2) and (Ia-3), wherein Q is as defined in entry D-114 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-114 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-114 of table D and p, R1, R3, R5a and R5b correspond in each case to a row of table C.

Table 115d: Compounds of formulae (Ia-1), (Ia-2) and (Ia-3), wherein Q is as defined in entry D-115 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-115 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-115 of table D and p, R1, R3, R5a and R5b correspond in each case to a row of table C.

Table 116d: Compounds of formulae (Ia-1), (Ia-2) and (Ia-3), wherein Q is as defined in entry D-116 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-116 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-116 of table D and p, R1, R3, R5a and R5b correspond in each case to a row of table C.

Table 117d: Compounds of formulae (Ia-1), (Ia-2) and (Ia-3), wherein Q is as defined in entry D-117 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-117 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-117 of table D and p, R1, R3, R5a and R5b correspond in each case to a row of table C.

Table 118d: Compounds of formulae (Ia-1), (Ia-2) and (Ia-3), wherein Q is as defined in entry D-118 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-118 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-118 of table D and p, R1, R3, R5a and R5b correspond in each case to a row of table C.

Table 119d: Compounds of formulae (Ia-1), (Ia-2) and (Ia-3), wherein Q is as defined in entry D-119 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-119 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-119 of table D and p, R1, R3, R5a and R5b correspond in each case to a row of table C.

Table 120d: Compounds of formulae (Ia-1), (Ia-2) and (Ia-3), wherein Q is as defined in entry D-120 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-120 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-120 of table D and p, R1, R3, R5a and R5b correspond in each case to a row of table C.

Table 121d: Compounds of formulae (Ia-1), (Ia-2) and (Ia-3), wherein Q is as defined in entry D-121 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-121 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-121 of table D and p, R1, R3, R5a and R5b correspond in each case to a row of table C.

Table 122d: Compounds of formulae (Ia-1), (Ia-2) and (Ia-3), wherein Q is as defined in entry D-122 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-122 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-122 of table D and p, R1, R3, R5a and R5b correspond in each case to a row of table C.

Table 123d: Compounds of formulae (Ia-1), (Ia-2) and (Ia-3), wherein Q is as defined in entry D-123 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-123 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-123 of table D and p, R1, R3, R5a and R5b correspond in each case to a row of table C.

Table 124d: Compounds of formulae (Ia-1), (Ia-2) and (Ia-3), wherein Q is as defined in entry D-124 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-124 of table D and p, R1, R3 and R5 correspond in each case to row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-124 of table D and p, R1, R3, R5a and R5b correspond in each case to a row of table C.

Table 125d: Compounds of formulae (Ia-1), (Ia-2) and (Ia-3), wherein Q is as defined in entry D-125 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-125 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-125 of table D and p, R1, R3, R5a and R5b correspond in each case to a row of table C.

Table 126d: Compounds of formulae (Ia-1), (Ia-2) and (Ia-3), wherein Q is as defined in entry D-126 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-126 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-126 of table D and p, R1, R3, R5a and R5b correspond in each case to a row of table C.

Table 127d: Compounds of formulae (Ia-1), (Ia-2) and (Ia-3), wherein Q is as defined in entry D-127 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-127 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-127 of table D and p, R1, R3, R5a and R5b correspond in each case to a row of table C.

Table 128d: Compounds of formulae (Ia-1), (Ia-2) and (Ia-3), wherein Q is as defined in entry D-128 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-128 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-128 of table D and p, R1, R3, R5a and R5b correspond in each case to a row of table C.

Table 129d: Compounds of formulae (Ia-1), (Ia-2) and (Ia-3), wherein Q is as defined in entry D-129 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-129 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-129 of table D and p, R1, R3, R5a and R5b correspond in each case to a row of table C.

Table 130d: Compounds of formulae (Ia-1), (Ia-2) and (Ia-3), wherein Q is as defined in entry D-130 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-130 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-130 of table D and p, R1, R3, R5a and R5b correspond in each case to a row of table C.

Table 131d: Compounds of formulae (Ia-1), (Ia-2) and (Ia-3), wherein Q is as defined in entry D-131 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-131 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-131 of table D and p, R1, R3, R5a and R5b correspond in each case to a row of table C.

Table 132d: Compounds of formulae (Ia-1), (Ia-2) and (Ia-3), wherein Q is as defined in entry D-132 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-132 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-132 of table D and p, R1, R3, R5a and R5b correspond in each case to a row of table C.

Table 133d: Compounds of formulae (Ia-1), (Ia-2) and (Ia-3), wherein Q is as defined in entry D-133 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-133 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-133 of table D and p, R1, R3, R5a and R5b correspond in each case to a row of table C.

Table 134d: Compounds of formulae (Ia-1), (Ia-2) and (Ia-3), wherein Q is as defined in entry D-134 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-134 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-134 of table D and p, R1, R3, R5a and R5b correspond in each case to a row of table C.

Table 135d: Compounds of formulae (Ia-1), (Ia-2) and (Ia-3), wherein Q is as defined in entry D-135 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-135 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-135 of table D and p, R1, R3, R5a and R5b correspond in each case to a row of table C.

Table 136d: Compounds of formulae (Ia-1), (Ia-2) and (Ia-3), wherein Q is as defined in entry D-136 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-136 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as Table 137d: Compounds of formulae (Ia-1), (Ia-2) and (Ia-3), wherein Q is as defined in entry D-137 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-137 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-137 of table D and p, R1, R3, R5a and R5b correspond in each case to a row of table C.

Table 138d: Compounds of formulae (Ia-1), (Ia-2) and (Ia-3), wherein Q is as defined in entry D-138 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-138 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-138 of table D and p, R1, R3, R5a and R5b correspond in each case to a row of table C.

Table 139d: Compounds of formulae (Ia-1), (Ia-2) and (Ia-3), wherein Q is as defined in entry D-139 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-139 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-139 of table D and p, R1, R3, R5a and R5b correspond in each case to a row of table C.

Table 140d: Compounds of formulae (Ia-1), (Ia-2) and (Ia-3), wherein Q is as defined in entry D-140 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-140 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-140 of table D and p, R1, R3, R5a and R5b correspond in each case to a row of table C.

Table 141d: Compounds of formulae (Ia-1), (Ia-2) and (Ia-3), wherein Q is as defined in entry D-141 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-141 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-141 of table D and p, R1, R3, R5a and R5b correspond in each case to a row of table C.

Table 142d: Compounds of formulae (Ia-1), (Ia-2) and (Ia-3), wherein Q is as defined in entry D-142 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-142 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-142 of table D and p, R1, R3, R5a and R5b correspond in each case to a row of table C.

Table 143d: Compounds of formulae (Ia-1), (Ia-2) and (Ia-3), wherein Q is as defined in entry D-143 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-143 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-143 of table D and p, R1, R3, R5a and R5b correspond in each case to a row of table C.

Table 144d: Compounds of formulae (Ia-1), (Ia-2) and (Ia-3), wherein Q is as defined in entry D-144 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-144 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-144 of table D and p, R1, R3, R5a and R5b correspond in each case to a row of table C.

Table 145d: Compounds of formulae (Ia-1), (Ia-2) and (Ia-3), wherein Q is as defined in entry D-145 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-145 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-145 of table D and p, R1, R3, R5a and R5b correspond in each case to a row of table C.

Table 146d: Compounds of formulae (Ia-1), (Ia-2) and (Ia-3), wherein Q is as defined in entry D-146 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-146 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-146 of table D and p, R1, R3, R5a and R5b correspond in each case to a row of table C.

Table 147d: Compounds of formulae (Ia-1), (Ia-2) and (Ia-3), wherein Q is as defined in entry D-147 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-147 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-147 of table D and p, R1, R3, R5a and R5b correspond in each case to a row of table C.

Table 148d: Compounds of formulae (Ia-1), (Ia-2) and (Ia-3), wherein Q is as defined in entry D-148 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-148 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-148 of table D and p, R1, R3, R5a and R5b correspond in each case to a row of table C.

Table 149d: Compounds of formulae (Ia-1), (Ia-2) and (Ia-3), wherein Q is as defined in entry D-149 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-149 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-149 of table D and p, R1, R3, R5a and R5b correspond in each case to a row of table C.

Table 150d: Compounds of formulae (Ia-1), (Ia-2) and (Ia-3), wherein Q is as defined in entry D-150 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-150 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-150 of table D and p, R1, R3, R5a and R5b correspond in each case to a row of table C.

Table 151d: Compounds of formulae (Ia-1), (Ia-2) and (Ia-3), wherein Q is as defined in entry D-151 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-151 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-151 of table D and p, R1, R3, R5a and R5b correspond in each case to a row of table C.

Table 152d: Compounds of formulae (Ia-1), (Ia-2) and (Ia-3), wherein Q is as defined in entry D-152 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-152 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-152 of table D and p, R1, R3, R5a and R5b correspond in each case to a row of table C.

Table 153d: Compounds of formulae (Ia-1), (Ia-2) and (Ia-3), wherein Q is as defined in entry D-153 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-153 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-153 of table D and p, R1, R3, R5a and R5b correspond in each case to a row of table C.

Table 154d: Compounds of formulae (Ia-1), (Ia-2) and (Ia-3), wherein Q is as defined in entry D-154 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-154 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-154 of table D and p, R1, R3, R5a and R5b correspond in each case to a row of table C.

Table 155d: Compounds of formulae (Ia-1), (Ia-2) and (Ia-3), wherein Q is as defined in entry D-155 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-155 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-155 of table D and p, R1, R3, R5a and R5b correspond in each case to a row of table C.

Table 156d: Compounds of formulae (Ia-1), (Ia-2) and (Ia-3), wherein Q is as defined in entry D-156 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-156 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-156 of table D and p, R1, R3, R5a and R5b correspond in each case to a row of table C.

Table 157d: Compounds of formulae (Ia-1), (Ia-2) and (Ia-3), wherein Q is as defined in entry D-157 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-157 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-157 of table D and p, R1, R3, R5a and R5b correspond in each case to a row of table C.

Table 158d: Compounds of formulae (Ia-1), (Ia-2) and (Ia-3), wherein Q is as defined in entry D-158 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-158 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-158 of table D and p, R1, R3, R5a and R5b correspond in each case to a row of table C.

Table 159d: Compounds of formulae (Ia-1), (Ia-2) and (Ia-3), wherein Q is as defined in entry D-159 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-159 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-159 of table D and p, R1, R3, R5a and R5b correspond in each case to a row of table C.

Table 160d: Compounds of formulae (Ia-1), (Ia-2) and (Ia-3), wherein Q is as defined in entry D-160 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-160 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-160 of table D and p, R1, R3, R5a and R5b correspond in each case to a row of table C.

Table 161d: Compounds of formulae (Ia-1), (Ia-2) and (Ia-3), wherein Q is as defined in entry D-161 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-161 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-161 of table D and p, R1, R3, R5a and R5b correspond in each case to a row of table C.

Table 162d: Compounds of formulae (Ia-1), (Ia-2) and (Ia-3), wherein Q is as defined in entry D-162 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-162 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-162 of table D and p, R1, R3, R5a and R5b correspond in each case to a row of table C.

Table 163d: Compounds of formulae (Ia-1), (Ia-2) and (Ia-3), wherein Q is as defined in entry D-163 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-163 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-163 of table D and p, R1, R3, R5a and R5b correspond in each case to a row of table C.

Table 164d: Compounds of formulae (Ia-1), (Ia-2) and (Ia-3), wherein Q is as defined in entry D-164 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-164 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-164 of table D and p, R1, R3, R5a and R5b correspond in each case to a row of table C.

Table 165d: Compounds of formulae (Ia-1), (Ia-2) and (Ia-3), wherein Q is as defined in entry D-165 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-165 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-165 of table D and p, R1, R3, R5a and R5b correspond in each case to a row of table C.

Table 166d: Compounds of formulae (Ia-1), (Ia-2) and (Ia-3), wherein Q is as defined in entry D-166 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-166 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-166 of table D and p, R1, R3, R5a and R5b correspond in each case to a row of table C.

Table 167d: Compounds of formulae (Ia-1), (Ia-2) and (Ia-3), wherein Q is as defined in entry D-167 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-167 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-167 of table D and p, R1, R3, R5a and R5b correspond in each case to a row of table C.

Table 168d: Compounds of formulae (Ia-1), (Ia-2) and (Ia-3), wherein Q is as defined in entry D-168 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-168 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-168 of table D and p, R1, R3, R5a and R5b correspond in each case to a row of table C.

Table 169d: Compounds of formulae (Ia-1), (Ia-2) and (Ia-3), wherein Q is as defined in entry D-169 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-169 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-169 of table D and p, R1, R3, R5a and R5b correspond in each case to a row of table C.

Table 170d: Compounds of formulae (Ia-1), (Ia-2) and (Ia-3), wherein Q is as defined in entry D-170 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-170 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-170 of table D and p, R1, R3, R5a and R5b correspond in each case to a row of table C.

Table 171d: Compounds of formulae (Ia-1), (Ia-2) and (Ia-3), wherein Q is as defined in entry D-171 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-171 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-171 of table D and p, R1, R3, R5a and R5b correspond in each case to a row of table C.

Table 172d: Compounds of formulae (Ia-1), (Ia-2) and (Ia-3), wherein Q is as defined in entry D-172 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-172 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-172 of table D and p, R1, R3, R5a and R5b correspond in each case to a row of table C.

Table 173d: Compounds of formulae (Ia-1), (Ia-2) and (Ia-3), wherein Q is as defined in entry D-173 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-173 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-173 of table D and p, R1, R3, R5a and R5b correspond in each case to a row of table C.

Table 174d: Compounds of formulae (Ia-1), (Ia-2) and (Ia-3), wherein Q is as defined in entry D-174 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-174 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-174 of table D and p, R1, R3, R5a and R5b correspond in each case to a row of table C.

Table 175d: Compounds of formulae (Ia-1), (Ia-2) and (Ia-3), wherein Q is as defined in entry D-175 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-175 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-175 of table D and p, R1, R3, R5a and R5b correspond in each case to a row of table C.

Table 176d: Compounds of formulae (Ia-1), (Ia-2) and (Ia-3), wherein Q is as defined in entry D-176 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-176 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-176 of table D and p, R1, R3, R5a and R5b correspond in each case to a row of table C.

Table 177d: Compounds of formulae (Ia-1), (Ia-2) and (Ia-3), wherein Q is as defined in entry D-177 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-177 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-177 of table D and p, R1, R3, R5a and R5b correspond in each case to a row of table C.

Table 178d: Compounds of formulae (Ia-1), (Ia-2) and (Ia-3), wherein Q is as defined in entry D-178 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-178 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-178 of table D and p, R1, R3, R5a and R5b correspond in each case to a row of table C.

Table 179d: Compounds of formulae (Ia-1), (Ia-2) and (Ia-3), wherein Q is as defined in entry D-179 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-179 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-179 of table D and p, R1, R3, R5a and R5b correspond in each case to a row of table C.

Table 180d: Compounds of formulae (Ia-1), (Ia-2) and (Ia-3), wherein Q is as defined in entry D-180 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-180 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-180 of table D and p, R1, R3, R5a and R5b correspond in each case to a row of table C.

Table 181d: Compounds of formulae (Ia-1), (Ia-2) and (Ia-3), wherein Q is as defined in entry D-181 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-181 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-181 of table D and p, R1, R3, R5a and R5b correspond in each case to a row of table C.

Table 182d: Compounds of formulae (Ia-1), (Ia-2) and (Ia-3), wherein Q is as defined in entry D-182 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-182 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-182 of table D and p, R1, R3, R5a and R5b correspond in each case to a row of table C.

Table 183d: Compounds of formulae (Ia-1), (Ia-2) and (Ia-3), wherein Q is as defined in entry D-183 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-183 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-183 of table D and p, R1, R3, R5a and R5b correspond in each case to a row of table C.

Table 184d: Compounds of formulae (Ia-1), (Ia-2) and (Ia-3), wherein Q is as defined in entry D-184 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-184 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-184 of table D and p, R1, R3, R5a and R5b correspond in each case to a row of table C.

Table 185d: Compounds of formulae (Ia-1), (Ia-2) and (Ia-3), wherein Q is as defined in entry D-185 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-185 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-185 of table D and p, R1, R3, R5a and R5b correspond in each case to a row of table C.

Table 186d: Compounds of formulae (Ia-1), (Ia-2) and (Ia-3), wherein Q is as defined in entry D-186 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-186 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-186 of table D and p, R1, R3, R5a and R5b correspond in each case to a row of table C.

Table 187d: Compounds of formulae (Ia-1), (Ia-2) and (Ia-3), wherein Q is as defined in entry D-187 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-187 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-187 of table D and p, R1, R3, R5a and R5b correspond in each case to a row of table C.

Table 188d: Compounds of formulae (Ia-1), (Ia-2) and (Ia-3), wherein Q is as defined in entry D-188 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-188 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-188 of table D and p, R1, R3, R5a and R5b correspond in each case to a row of table C.

Table 189d: Compounds of formulae (Ia-1), (Ia-2) and (Ia-3), wherein Q is as defined in entry D-189 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-189 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-189 of table D and p, R1, R3, R5a and R5b correspond in each case to a row of table C.

Table 190d: Compounds of formulae (Ia-1), (Ia-2) and (Ia-3), wherein Q is as defined in entry D-190 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-190 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-190 of table D and p, R1, R3, R5a and R5b correspond in each case to a row of table C.

Table 191d: Compounds of formulae (Ia-1), (Ia-2) and (Ia-3), wherein Q is as defined in entry D-191 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-191 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-191 of table D and p, R1, R3, R5a and R5b correspond in each case to a row of table C.

Table 192d: Compounds of formulae (Ia-1), (Ia-2) and (Ia-3), wherein Q is as defined in entry D-192 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-192 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-192 of table D and p, R1, R3, R5a and R5b correspond in each case to a row of table C.

Table 193d: Compounds of formulae (Ia-1), (Ia-2) and (Ia-3), wherein Q is as defined in entry D-193 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-193 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-193 of table D and p, R1, R3, R5a and R5b correspond in each case to a row of table C.

Table 194d: Compounds of formulae (Ia-1), (Ia-2) and (Ia-3), wherein Q is as defined in entry D-194 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-194 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-194 of table D and p, R1, R3, R5a and R5b correspond in each case to a row of table C.

Table 195d: Compounds of formulae (Ia-1), (Ia-2) and (Ia-3), wherein Q is as defined in entry D-195 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-195 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-195 of table D and p, R1, R3, R5a and R5b correspond in each case to a row of table C.

Table 196d: Compounds of formulae (Ia-1), (Ia-2) and (Ia-3), wherein Q is as defined in entry D-196 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-196 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-196 of table D and p, R1, R3, R5a and R5b correspond in each case to a row of table C.

Table 197d: Compounds of formulae (Ia-1), (Ia-2) and (Ia-3), wherein Q is as defined in entry D-197 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-197 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-197 of table D and p, R1, R3, R5a and R5b correspond in each case to a row of table C.

Table 198d: Compounds of formulae (Ia-1), (Ia-2) and (Ia-3), wherein Q is as defined in entry D-198 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-198 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-198 of table D and p, R1, R3, R5a and R5b correspond in each case to a row of table C.

Table 199d: Compounds of formulae (Ia-1), (Ia-2) and (Ia-3), wherein Q is as defined in entry D-199 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-199 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-199 of table D and p, R1, R3, R5a and R5b correspond in each case to a row of table C.

Table 200d: Compounds of formulae (Ia-1), (Ia-2) and (Ia-3), wherein Q is as defined in entry D-200 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-200 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-200 of table D and p, R1, R3, R5a and R5b correspond in each case to a row of table C.

Table 201d: Compounds of formulae (Ia-1), (Ia-2) and (Ia-3), wherein Q is as defined in entry D-201 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-201 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-201 of table D and p, R1, R3, R5a and R5b correspond in each case to a row of table C.

Table 202d: Compounds of formulae (Ia-1), (Ia-2) and (Ia-3), wherein Q is as defined in entry D-202 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-202 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-202 of table D and p, R1, R3, R5a and R5b correspond in each case to a row of table C.

Table 203d: Compounds of formulae (Ia-1), (Ia-2) and (Ia-3), wherein Q is as defined in entry D-203 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-203 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-203 of table D and p, R1, R3, R5a and R5b correspond in each case to a row of table C.

Table 204d: Compounds of formulae (Ia-1), (Ia-2) and (Ia-3), wherein Q is as defined in entry D-204 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-204 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-204 of table D and p, R1, R3, R5a and R5b correspond in each case to a row of table C.

Table 205d: Compounds of formulae (Ia-1), (Ia-2) and (Ia-3), wherein Q is as defined in entry D-205 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-205 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-205 of table D and p, R1, R3, R5a and R5b correspond in each case to a row of table C.

Table 206d: Compounds of formulae (Ia-1), (Ia-2) and (Ia-3), wherein Q is as defined in entry D-206 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-206 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-206 of table D and p, R1, R3, R5a and R5b correspond in each case to a row of table C.

Table 207d: Compounds of formulae (Ia-1), (Ia-2) and (Ia-3), wherein Q is as defined in entry D-207 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-207 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-207 of table D and p, R1, R3, R5a and R5b correspond in each case to a row of table C.

Table 208d: Compounds of formulae (Ia-1), (Ia-2) and (Ia-3), wherein Q is as defined in entry D-208 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-208 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-208 of table D and p, R1, R3, R5a and R5b correspond in each case to a row of table C.

Table 209d: Compounds of formulae (Ia-1), (Ia-2) and (Ia-3), wherein Q is as defined in entry D-209 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-209 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-209 of table D and p, R1, R3, R5a and R5b correspond in each case to a row of table C.

Table 210d: Compounds of formulae (Ia-1), (Ia-2) and (Ia-3), wherein Q is as defined in entry D-210 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-210 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-210 of table D and p, R1, R3, R5a and R5b correspond in each case to a row of table C.

Table 211d: Compounds of formulae (Ia-1), (Ia-2) and (Ia-3), wherein Q is as defined in entry D-211 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-211 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-211 of table D and p, R1, R3, R5a and R5b correspond in each case to a row of table C.

Table 212d: Compounds of formulae (Ia-1), (Ia-2) and (Ia-3), wherein Q is as defined in entry D-212 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-212 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-212 of table D and p, R1, R3, R5a and R5b correspond in each case to a row of table C.

Table 213d: Compounds of formulae (Ia-1), (Ia-2) and (Ia-3), wherein Q is as defined in entry D-213 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-213 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-213 of table D and p, R1, R3, R5a and R5b correspond in each case to a row of table C.

Table 214d: Compounds of formulae (Ia-1), (Ia-2) and (Ia-3), wherein Q is as defined in entry D-214 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-214 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-214 of table D and p, R1, R3, R5a and R5b correspond in each case to a row of table C.

Table 215d: Compounds of formulae (Ia-1), (Ia-2) and (Ia-3), wherein Q is as defined in entry D-215 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-215 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-215 of table D and p, R1, R3, R5a and R5b correspond in each case to a row of table C.

Table 216d: Compounds of formulae (Ia-1), (Ia-2) and (Ia-3), wherein Q is as defined in entry D-216 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-216 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-216 of table D and p, R1, R3, R5a and R5b correspond in each case to a row of table C.

Table 217d: Compounds of formulae (Ia-1), (Ia-2) and (Ia-3), wherein Q is as defined in entry D-217 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-217 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-217 of table D and p, R1, R3, R5a and R5b correspond in each case to a row of table C.

Table 218d: Compounds of formulae (Ia-1), (Ia-2) and (Ia-3), wherein Q is as defined in entry D-218 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-218 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-218 of table D and p, R1, R3, R5a and R5b correspond in each case to a row of table C.

Table 219d: Compounds of formulae (Ia-1), (Ia-2) and (Ia-3), wherein Q is as defined in entry D-219 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-219 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-219 of table D and p, R1, R3, R5a and R5b correspond in each case to a row of table C.

Table 220d: Compounds of formulae (Ia-1), (Ia-2) and (Ia-3), wherein Q is as defined in entry D-220 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-220 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-220 of table D and p, R1, R3, R5a and R5b correspond in each case to a row of table C.

Table 221d: Compounds of formulae (Ia-1), (Ia-2) and (Ia-3), wherein Q is as defined in entry D-221 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-221 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-221 of table D and p, R1, R3, R5a and R5b correspond in each case to a row of table C.

Table 222d: Compounds of formulae (Ia-1), (Ia-2) and (Ia-3), wherein Q is as defined in entry D-222 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-222 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-222 of table D and p, R1, R3, R5a and R5b correspond in each case to a row of table C.

Table 223d: Compounds of formulae (Ia-1), (Ia-2) and (Ia-3), wherein Q is as defined in entry D-223 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-223 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-223 of table D and p, R1, R3, R5a and R5b correspond in each case to a row of table C.

Table 224d: Compounds of formulae (Ia-1), (Ia-2) and (Ia-3), wherein Q is as defined in entry D-224 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-224 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-224 of table D and p, R1, R3, R5a and R5b correspond in each case to a row of table C.

Table 225d: Compounds of formulae (Ia-1), (Ia-2) and (Ia-3), wherein Q is as defined in entry D-225 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-225 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-225 of table D and p, R1, R3, R5a and R5b correspond in each case to a row of table C.

Table 226d: Compounds of formulae (Ia-1), (Ia-2) and (Ia-3), wherein Q is as defined in entry D-226 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-226 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-226 of table D and p, R1, R3, R5a and R5b correspond in each case to a row of table C.

Table 227d: Compounds of formulae (Ia-1), (Ia-2) and (Ia-3), wherein Q is as defined in entry D-227 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-227 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-227 of table D and p, R1, R3, R5a and R5b correspond in each case to a row of table C.

Table 228d: Compounds of formulae (Ia-1), (Ia-2) and (Ia-3), wherein Q is as defined in entry D-228 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-228 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-228 of table D and p, R1, R3, R5a and R5b correspond in each case to a row of table C.

Table 229d: Compounds of formulae (Ia-1), (Ia-2) and (Ia-3), wherein Q is as defined in entry D-229 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-229 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-229 of table D and p, R1, R3, R5a and R5b correspond in each case to a row of table C.

Table 230d: Compounds of formulae (Ia-1), (Ia-2) and (Ia-3), wherein Q is as defined in entry D-230 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-230 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-230 of table D and p, R1, R3, R5a and R5b correspond in each case to a row of table C.

Table 231d: Compounds of formulae (Ia-1), (Ia-2) and (Ia-3), wherein Q is as defined in entry D-231 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-231 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-231 of table D and p, R1, R3, R5a and R5b correspond in each case to a row of table C.

Table 232d: Compounds of formulae (Ia-1), (Ia-2) and (Ia-3), wherein Q is as defined in entry D-232 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-232 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-232 of table D and p, R1, R3, R5a and R5b correspond in each case to a row of table C.

Table 233d: Compounds of formulae (Ia-1), (Ia-2) and (Ia-3), wherein Q is as defined in entry D-233 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-233 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-233 of table D and p, R1, R3, R5a and R5b correspond in each case to a row of table C.

Table 234d: Compounds of formulae (Ia-1), (Ia-2) and (Ia-3), wherein Q is as defined in entry D-234 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-234 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-234 of table D and p, R1, R3, R5a and R5b correspond in each case to a row of table C.

Table 235d: Compounds of formulae (Ia-1), (Ia-2) and (Ia-3), wherein Q is as defined in entry D-235 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-235 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-235 of table D and p, R1, R3, R5a and R5b correspond in each case to a row of table C.

Table 236d: Compounds of formulae (Ia-1), (Ia-2) and (Ia-3), wherein Q is as defined in entry D-236 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-236 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-236 of table D and p, R1, R3, R5a and R5b correspond in each case to a row of table C.

Table 237d: Compounds of formulae (Ia-1), (Ia-2) and (Ia-3), wherein Q is as defined in entry D-237 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-237 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-237 of table D and p, R1, R3, R5a and R5b correspond in each case to a row of table C.

Table 238d: Compounds of formulae (Ia-1), (Ia-2) and (Ia-3), wherein Q is as defined in entry D-238 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-238 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-238 of table D and p, R1, R3, R5a and R5b correspond in each case to a row of table C.

Table 239d: Compounds of formulae (Ia-1), (Ia-2) and (Ia-3), wherein Q is as defined in entry D-239 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-239 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-239 of table D and p, R1, R3, R5a and R5b correspond in each case to a row of table C.

Table 240d: Compounds of formulae (Ia-1), (Ia-2) and (Ia-3), wherein Q is as defined in entry D-240 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-240 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-240 of table D and p, R1, R3, R5a and R5b correspond in each case to a row of table C.

Table 241d: Compounds of formulae (Ia-1), (Ia-2) and (Ia-3), wherein Q is as defined in entry D-241 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-241 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-241 of table D and p, R1, R3, R5a and R5b correspond in each case to a row of table C.

Table 242d: Compounds of formulae (Ia-1), (Ia-2) and (Ia-3), wherein Q is as defined in entry D-242 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-242 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-242 of table D and p, R1, R3, R5a and R5b correspond in each case to a row of table C.

Table 243d: Compounds of formulae (Ia-1), (Ia-2) and (Ia-3), wherein Q is as defined in entry D-243 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-243 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-243 of table D and p, R1, R3, R5a and R5b correspond in each case to a row of table C.

Table 244d: Compounds of formulae (Ia-1), (Ia-2) and (Ia-3), wherein Q is as defined in entry D-244 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-244 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-244 of table D and p, R1, R3, R5a and R5b correspond in each case to a row of table C.

Table 245d: Compounds of formulae (Ia-1), (Ia-2) and (Ia-3), wherein Q is as defined in entry D-245 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-245 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-245 of table D and p, R1, R3, R5a and R5b correspond in each case to a row of table C.

Table 246d: Compounds of formulae (Ia-1), (Ia-2) and (Ia-3), wherein Q is as defined in entry D-246 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-246 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-246 of table D and p, R1, R3, R5a and R5b correspond in each case to a row of table C.

Table 247d: Compounds of formulae (Ia-1), (Ia-2) and (Ia-3), wherein Q is as defined in entry D-247 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-247 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-247 of table D and p, R1, R3, R5a and R5b correspond in each case to a row of table C.

Table 248d: Compounds of formulae (Ia-1), (Ia-2) and (Ia-3), wherein Q is as defined in entry D-248 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-248 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-248 of table D and p, R1, R3, R5a and R5b correspond in each case to a row of table C.

Table 249d: Compounds of formulae (Ia-1), (Ia-2) and (Ia-3), wherein Q is as defined in entry D-249 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-249 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-249 of table D and p, R1, R3, R5a and R5b correspond in each case to a row of table C.

Table 250d: Compounds of formulae (Ia-1), (Ia-2) and (Ia-3), wherein Q is as defined in entry D-250 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-250 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-250 of table D and p, R1, R3, R5a and R5b correspond in each case to a row of table C.

Table 251d: Compounds of formulae (Ia-1), (Ia-2) and (Ia-3), wherein Q is as defined in entry D-251 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-251 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-251 of table D and p, R1, R3, R5a and R5b correspond in each case to a row of table C.

Table 252d: Compounds of formulae (Ia-1), (Ia-2) and (Ia-3), wherein Q is as defined in entry D-252 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-252 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-252 of table D and p, R1, R3, R5a and R5b correspond in each case to a row of table C.

Table 253d: Compounds of formulae (Ia-1), (Ia-2) and (Ia-3), wherein Q is as defined in entry D-253 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-253 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-253 of table D and p, R1, R3, R5a and R5b correspond in each case to a row of table C.

Table 254d: Compounds of formulae (Ia-1), (Ia-2) and (Ia-3), wherein Q is as defined in entry D-254 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-254 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-254 of table D and p, R1, R3, R5a and R5b correspond in each case to a row of table C.

Table 255d: Compounds of formulae (Ia-1), (Ia-2) and (Ia-3), wherein Q is as defined in entry D-255 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-255 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-255 of table D and p, R1, R3, R5a and R5b correspond in each case to a row of table C.

Table 256d: Compounds of formulae (Ia-1), (Ia-2) and (Ia-3), wherein Q is as defined in entry D-256 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-256 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-256 of table D and p, R1, R3, R5a and R5b correspond in each case to a row of table C.

Table 257d: Compounds of formulae (Ia-1), (Ia-2) and (Ia-3), wherein Q is as defined in entry D-257 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-257 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-257 of table D and p, R1, R3, R5a and R5b correspond in each case to a row of table C.

Table 258d: Compounds of formulae (Ia-1), (Ia-2) and (Ia-3), wherein Q is as defined in entry D-258 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-258 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-258 of table D and p, R1, R3, R5a and R5b correspond in each case to a row of table C.

Table 259d: Compounds of formulae (Ia-1), (Ia-2) and (Ia-3), wherein Q is as defined in entry D-259 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-259 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-259 of table D and p, R1, R3, R5a and R5b correspond in each case to a row of table C.

Table 260d: Compounds of formulae (Ia-1), (Ia-2) and (Ia-3), wherein Q is as defined in entry D-260 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-260 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-260 of table D and p, R1, R3, R5a and R5b correspond in each case to a row of table C.

Table 261d: Compounds of formulae (Ia-1), (Ia-2) and (Ia-3), wherein Q is as defined in entry D-261 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-261 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-261 of table D and p, R1, R3, R5a and R5b correspond in each case to a row of table C.

Table 262d: Compounds of formulae (Ia-1), (Ia-2) and (Ia-3), wherein Q is as defined in entry D-262 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-262 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-262 of table D and p, R1, R3, R5a and R5b correspond in each case to a row of table C.

Table 263d: Compounds of formulae (Ia-1), (Ia-2) and (Ia-3), wherein Q is as defined in entry D-263 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-263 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-263 of table D and p, R1, R3, R5a and R5b correspond in each case to a row of table C.

Table 264d: Compounds of formulae (Ia-1), (Ia-2) and (Ia-3), wherein Q is as defined in entry D-264 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-264 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-264 of table D and p, R1, R3, R5a and R5b correspond in each case to a row of table C.

Table 265d: Compounds of formulae (Ia-1), (Ia-2) and (Ia-3), wherein Q is as defined in entry D-265 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-265 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-265 of table D and p, R1, R3, R5a and R5b correspond in each case to a row of table C.

Table 266d: Compounds of formulae (Ia-1), (Ia-2) and (Ia-3), wherein Q is as defined in entry D-266 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-266 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-266 of table D and p, R1, R3, R5a and R5b correspond in each case to a row of table C.

Table 267d: Compounds of formulae (Ia-1), (Ia-2) and (Ia-3), wherein Q is as defined in entry D-267 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-267 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-267 of table D and p, R1, R3, R5a and R5b correspond in each case to a row of table C.

Table 268d: Compounds of formulae (Ia-1), (Ia-2) and (Ia-3), wherein Q is as defined in entry D-268 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-268 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-268 of table D and p, R1, R3, R5a and R5b correspond in each case to a row of table C.

Table 269d: Compounds of formulae (Ia-1), (Ia-2) and (Ia-3), wherein Q is as defined in entry D-269 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-269 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-269 of table D and p, R1, R3, R5a and R5b correspond in each case to a row of table C.

Table 270d: Compounds of formulae (Ia-1), (Ia-2) and (Ia-3), wherein Q is as defined in entry D-270 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-270 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-270 of table D and p, R1, R3, R5a and R5b correspond in each case to a row of table C.

Table 271d: Compounds of formulae (Ia-1), (Ia-2) and (Ia-3), wherein Q is as defined in entry D-271 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-271 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-271 of table D and p, R1, R3, R5a and R5b correspond in each case to a row of table C.

Table 272d: Compounds of formulae (Ia-1), (Ia-2) and (Ia-3), wherein Q is as defined in entry D-272 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-272 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-272 of table D and p, R1, R3, R5a and R5b correspond in each case to a row of table C.

Table 273d: Compounds of formulae (Ia-1), (Ia-2) and (Ia-3), wherein Q is as defined in entry D-273 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-273 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-273 of table D and p, R1, R3, R5a and R5b correspond in each case to a row of table C.

Table 274d: Compounds of formulae (Ia-1), (Ia-2) and (Ia-3), wherein Q is as defined in entry D-274 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-274 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-274 of table D and p, R1, R3, R5a and R5b correspond in each case to a row of table C.

Table 275d: Compounds of formulae (Ia-1), (Ia-2) and (Ia-3), wherein Q is as defined in entry D-275 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-275 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-275 of table D and p, R1, R3, R5a and R5b correspond in each case to a row of table C.

Table 276d: Compounds of formulae (Ia-1), (Ia-2) and (Ia-3), wherein Q is as defined in entry D-276 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-276 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-276 of table D and p, R1, R3, R5a and R5b correspond in each case to a row of table C.

Table 277d: Compounds of formulae (Ia-1), (Ia-2) and (Ia-3), wherein Q is as defined in entry D-277 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-277 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-277 of table D and p, R1, R3, R5a and R5b correspond in each case to a row of table C.

Table 278d: Compounds of formulae (Ia-1), (Ia-2) and (Ia-3), wherein Q is as defined in entry D-278 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-278 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-278 of table D and p, R1, R3, R5a and R5b correspond in each case to a row of table C.

Table 279d: Compounds of formulae (Ia-1), (Ia-2) and (Ia-3), wherein Q is as defined in entry D-279 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-279 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-279 of table D and p, R1, R3, R5a and R5b correspond in each case to a row of table C.

Table 280d: Compounds of formulae (Ia-1), (Ia-2) and (Ia-3), wherein Q is as defined in entry D-280 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-280 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-280 of table D and p, R1, R3, R5a and R5b correspond in each case to a row of table C.

Table 281d: Compounds of formulae (Ia-1), (Ia-2) and (Ia-3), wherein Q is as defined in entry D-281 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-281 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-281 of table D and p, R1, R3, R5a and R5b correspond in each case to a row of table C.

Table 282d: Compounds of formulae (Ia-1), (Ia-2) and (Ia-3), wherein Q is as defined in entry D-282 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-282 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-282 of table D and p, R1, R3, R5a and R5b correspond in each case to a row of table C.

Table 283d: Compounds of formulae (Ia-1), (Ia-2) and (Ia-3), wherein Q is as defined in entry D-283 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-283 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-283 of table D and p, R1, R3, R5a and R5b correspond in each case to a row of table C.

Table 284d: Compounds of formulae (Ia-1), (Ia-2) and (Ia-3), wherein Q is as defined in entry D-284 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-284 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-284 of table D and p, R1, R3, R5a and R5b correspond in each case to a row of table C.

Table 285d: Compounds of formulae (Ia-1), (Ia-2) and (Ia-3), wherein Q is as defined in entry D-285 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-285 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-285 of table D and p, R1, R3, R5a and R5b correspond in each case to a row of table C.

Table 286d: Compounds of formulae (Ia-1), (Ia-2) and (Ia-3), wherein Q is as defined in entry D-286 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-286 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-286 of table D and p, R1, R3, R5a and R5b correspond in each case to a row of table C.

Table 287d: Compounds of formulae (Ia-1), (Ia-2) and (Ia-3), wherein Q is as defined in entry D-287 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-287 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-287 of table D and p, R1, R3, R5a and R5b correspond in each case to a row of table C.

Table 288d: Compounds of formulae (Ia-1), (Ia-2) and (Ia-3), wherein Q is as defined in entry D-288 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-288 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-288 of table D and p, R1, R3, R5a and R5b correspond in each case to a row of table C.

Table 289d: Compounds of formulae (Ia-1), (Ia-2) and (Ia-3), wherein Q is as defined in entry D-289 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-289 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-289 of table D and p, R1, R3, R5a and R5b correspond in each case to a row of table C.

Table 290d: Compounds of formulae (Ia-1), (Ia-2) and (Ia-3), wherein Q is as defined in entry D-290 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-290 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-290 of table D and p, R1, R3, R5a and R5b correspond in each case to a row of table C.

Table 291d: Compounds of formulae (Ia-1), (Ia-2) and (Ia-3), wherein Q is as defined in entry D-291 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-291 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-291 of table D and p, R1, R3, R5a and R5b correspond in each case to a row of table C.

Table 292d: Compounds of formulae (Ia-1), (Ia-2) and (Ia-3), wherein Q is as defined in entry D-292 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-292 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-292 of table D and p, R1, R3, R5a and R5b correspond in each case to a row of table C.

Table 293d: Compounds of formulae (Ia-1), (Ia-2) and (Ia-3), wherein Q is as defined in entry D-293 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-293 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-293 of table D and p, R1, R3, R5a and R5b correspond in each case to a row of table C.

Table 294d: Compounds of formulae (Ia-1), (Ia-2) and (Ia-3), wherein Q is as defined in entry D-294 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-294 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-294 of table D and p, R1, R3, R5a and R5b correspond in each case to a row of table C.

Table 295d: Compounds of formulae (Ia-1), (Ia-2) and (Ia-3), wherein Q is as defined in entry D-295 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-295 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-295 of table D and p, R1, R3, R5a and R5b correspond in each case to a row of table C.

Table 296d: Compounds of formulae (Ia-1), (Ia-2) and (Ia-3), wherein Q is as defined in entry D-296 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-296 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-296 of table D and p, R1, R3, R5a and R5b correspond in each case to a row of table C.

Table 297d: Compounds of formulae (Ia-1), (Ia-2) and (Ia-3), wherein Q is as defined in entry D-297 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-297 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-297 of table D and p, R1, R3, R5a and R5b correspond in each case to a row of table C.

Table 298d: Compounds of formulae (Ia-1), (Ia-2) and (Ia-3), wherein Q is as defined in entry D-298 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-298 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-298 of table D and p, R1, R3, R5a and R5b correspond in each case to a row of table C.

Table 299d: Compounds of formulae (Ia-1), (Ia-2) and (Ia-3), wherein Q is as defined in entry D-299 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-299 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-299 of table D and p, R1, R3, R5a and R5b correspond in each case to a row of table C.

Table 300d: Compounds of formulae (Ia-1), (Ia-2) and (Ia-3), wherein Q is as defined in entry D-300 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-300 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-300 of table D and p, R1, R3, R5a and R5b correspond in each case to a row of table C.

Table 301d: Compounds of formulae (Ia-1), (Ia-2) and (Ia-3), wherein Q is as defined in entry D-301 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-301 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-301 of table D and p, R1, R3, R5a and R5b correspond in each case to a row of table C.

Table 302d: Compounds of formulae (Ia-1), (Ia-2) and (Ia-3), wherein Q is as defined in entry D-302 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-302 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-302 of table D and p, R1, R3, R5a and R5b correspond in each case to a row of table C.

Table 303d: Compounds of formulae (Ia-1), (Ia-2) and (Ia-3), wherein Q is as defined in entry D-303 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-303 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-303 of table D and p, R1, R3, R5a and R5b correspond in each case to a row of table C.

Table 304d: Compounds of formulae (Ia-1), (Ia-2) and (Ia-3), wherein Q is as defined in entry D-304 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-304 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-304 of table D and p, R1, R3, R5a and R5b correspond in each case to a row of table C.

Table 305d: Compounds of formulae (Ia-1), (Ia-2) and (Ia-3), wherein Q is as defined in entry D-305 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-305 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-305 of table D and p, R1, R3, R5a and R5b correspond in each case to a row of table C.

Table 306d: Compounds of formulae (Ia-1), (Ia-2) and (Ia-3), wherein Q is as defined in entry D-306 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-306 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-306 of table D and p, R1, R3, R5a and R5b correspond in each case to a row of table C.

Table 307d: Compounds of formulae (Ia-1), (Ia-2) and (Ia-3), wherein Q is as defined in entry D-307 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-307 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-307 of table D and p, R1, R3, R5a and R5b correspond in each case to a row of table C.

Table 308d: Compounds of formulae (Ia-1), (Ia-2) and (Ia-3), wherein Q is as defined in entry D-308 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-308 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-308 of table D and p, R1, R3, R5a and R5b correspond in each case to a row of table C.

Table 309d: Compounds of formulae (Ia-1), (Ia-2) and (Ia-3), wherein Q is as defined in entry D-309 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-309 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-309 of table D and p, R1, R3, R5a and R5b correspond in each case to a row of table C.

Table 310d: Compounds of formulae (Ia-1), (Ia-2) and (Ia-3), wherein Q is as defined in entry D-310 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-310 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-310 of table D and p, R1, R3, R5a and R5b correspond in each case to a row of table C.

Table 311d: Compounds of formulae (Ia-1), (Ia-2) and (Ia-3), wherein Q is as defined in entry D-311 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-311 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-311 of table D and p, R1, R3, R5a and R5b correspond in each case to a row of table C.

Table 312d: Compounds of formulae (Ia-1), (Ia-2) and (Ia-3), wherein Q is as defined in entry D-312 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-312 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-312 of table D and p, R1, R3, R5a and R5b correspond in each case to a row of table C.

Table 313d: Compounds of formulae (Ia-1), (Ia-2) and (Ia-3), wherein Q is as defined in entry D-313 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-313 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-313 of table D and p, R1, R3, R5a and R5b correspond in each case to a row of table C.

Table 314d: Compounds of formulae (Ia-1), (Ia-2) and (Ia-3), wherein Q is as defined in entry D-314 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-314 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-314 of table D and p, R1, R3, R5a and R5b correspond in each case to a row of table C.

Table 315d: Compounds of formulae (Ia-1), (Ia-2) and (Ia-3), wherein Q is as defined in entry D-315 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-315 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-315 of table D and p, R1, R3, R5a and R5b correspond in each case to a row of table C.

Table 316d: Compounds of formulae (Ia-1), (Ia-2) and (Ia-3), wherein Q is as defined in entry D-316 of table D and p, R1, R3 and R5 correspond in each case to a row of table A; compounds of formulae (Ib-1), (Ib-2), (Ib-3), (Ib-4), (Ib-5), (Ib-6), (Ib-7), (Ib-8), (Ib-9), (Ib-10), (Ib-11) and (Ib-12), wherein Q is as defined in entry D-316 of table D and p, R1, R3 and R5 correspond in each case to a row of table B; and compounds of formulae (Ic-1), (Ic-2), (Ic-3), (Ic-4), (Ic-5), (Ic-6), (Ic-7), (Ic-8) and (Ic-9), wherein Q is as defined in entry D-316 of table D and p, R1, R3, R5a and R5b correspond in each case to a row of table C.

Stereoisomers and Polymorphic Forms

It will be appreciated by those of skill in the art that certain compounds of formula (I) used in the methods and uses of the invention may exist and be isolated as optically active and racemic forms. Compounds having one or more chiral centers, including that at a sulfur atom, may be present as single enantiomers or diastereomers or as mixtures of enantiomers and/or diastereomers. For example, it is well known in the art that sulfoxide compounds may be optically active and may exist as single enantiomers or racemic mixtures. In addition, compounds of the invention may include one or more chiral centers, which results in a theoretical number of optically active isomers. Where compounds of the invention include n chiral centers, the compounds may comprise up to $2^n$ optical isomers. The present invention encompasses the specific enantiomers or diastereomers of each compound as well as mixtures of different enantiomers and/or diastereomers of the compounds of the invention that possess the useful properties described herein. The optically active forms can be prepared by, for example, resolution of the racemic forms by selective crystallization techniques, by synthesis from optically active precursors, by chiral synthesis, by chromatographic separation using a chiral stationary phase or by enzymatic resolution.

The compounds used in the present invention may be amorphous or may exist in one or more different crystalline states (polymorphs) or modifications which may have different macroscopic properties such as stability or show different biological properties such as activities. The present invention includes both amorphous and crystalline compounds of formula (I), mixtures of different crystalline states or modifications of the respective compound (I), as well as amorphous or crystalline salts thereof.

In addition, the compounds used the invention may exist as hydrates or solvates, in which a certain stoichiometric amount of water or a solvent is associated with the molecule in the crystalline form. The hydrates and solvates of the compounds of formula (I) are also the subject of the invention.

Salts

In addition to the neutral compounds of formula (I), salt forms of the compounds are also active against animal parasites. Thus, veterinarily acceptable salts of the compounds of formula (I) and may be utilized in the methods and uses of the invention. The terms "veterinarily acceptable salt" is used throughout the specification to describe any salts of the compounds that are acceptable for administration for veterinary applications, and which provides the active compound upon administration.

In cases where compounds are sufficiently basic or acidic to form stable non-toxic acid or base salts, the compounds may be in the form of a veterinarily acceptable salt. Veterinarily acceptable salts include those derived from veterinarily acceptable inorganic or organic bases and acids. Suitable salts include those comprising alkali metals such as lithium, sodium or potassium, alkaline earth metals such as calcium, magnesium and barium. Salts comprising transition metals including, but not limited to, manganese, copper, zinc and iron are also suitable. In addition, salts comprising ammonium cations ($NH_4^+$) as well as substituted ammonium cations, in which one or more of the hydrogen atoms are replaced by alkyl or aryl groups are encompassed by the invention.

Salts derived from inorganic acids including, but not limited to, hydrohalide acids (HCl, HBr, HF, HI), sulfuric acid, nitric acid, phosphoric acid, and the like are suitable. Suitable inorganic salts also include, but not limited to, bicarbonate, and carbonate salts. In some embodiments, examples of veterinarily acceptable salts are organic acid addition salts formed with organic acids including, but not limited to, maleate, dimaleate, fumarate, tosylate, methanesulfonate, acetate, citrate, malonate, tartrate, succinate, benzoate, ascorbate, α-ketoglutarate, and α-glycerophosphate. Of course, other acceptable organic acids may be used.

Alkali metal (for example, sodium, potassium or lithium) or alkaline earth metal (for example calcium) salts of the compounds can also be made by reacting a sufficiently acidic residue on the compounds with a hydroxide of the alkali metal or alkaline earth metal.

Veterinarily acceptable salts may be obtained using standard procedures well known in the art, for example by reacting a sufficiently basic compound such as an amine with a suitably acid functional group present in the compound, or by reacting a suitable acid with a suitably basic functional group on the compound of the invention.

Methods of Preparation:

The parasiticidal compounds of formula (I) according to the invention may be prepared by a process comprising the step of reacting a compound of formula (XI),

wherein Y is defined as in formula (I);
with a compound of formula (XII),

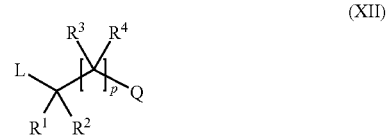

wherein $R^2$, $R^3$, $R^4$, Q and p are defined as in formula (I); and

L is a leaving group, optionally in the presence of a base. Further examples of the preparation of compounds of formula (I) are found in the non-limiting examples.

In some embodiments, the compounds of formula (I) according to the present invention can be prepared according to processes and preparation schemes described below.

In the following schemes and processes, if not otherwise specified, the definition of the substituents, variables and indices in the formulae used correspond to the definitions given for formula (I) above.

In one embodiment, compounds of formula (I) can be prepared as shown in Scheme A below.

Scheme A.

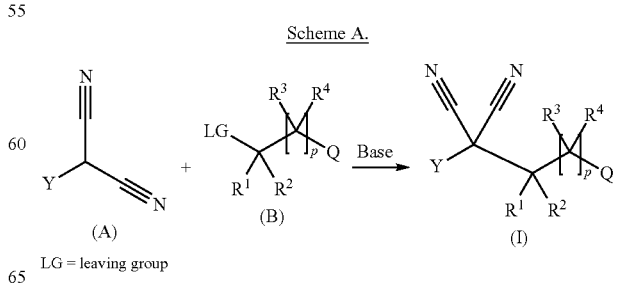

LG = leaving group

In this embodiment, compounds of formula (A) are reacted with compounds of formula (B) in the presence of a suitable base to give compounds of formula (I). A representative procedure has been described in e.g. M. M. Meyers, J. Sun, K. E. Carlson, G. A. Marriner, B. S. Katzenellenbogen, J. A. Katzenellenbogen, J. Med. Chem. 2001, 44, 4230-4251.

In another embodiment, compounds of formula (A) can be prepared by treatment of the corresponding iodine compound (A-1) with malonodinitrile (Scheme B) as described in various publications. For example, this can be achieved in the presence of a base and a suitable catalyst system as described in e.g. J. M. Atkins, S. A. Moteki, S. G. DiMagno, J. M. Takacs, Org. Lett. 2006, 13, 2759-2762. Alternatively, the reaction can also be carried out via copper catalysis in the presence of a base as described e.g. in M. Makosza, A. Chesnokov, Tetrahedron 2008, 64, 5925-5932.

Scheme B.

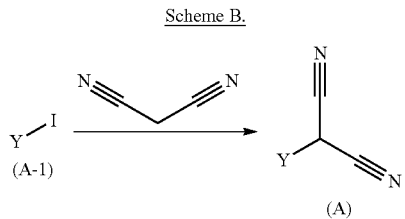

In still another embodiment, compounds of formula (B) with p=0 like e.g. (B-5) in Scheme C that require a leaving group "LG" e.g. halogens or mesylates can be obtained starting from the respective halogenated benzene derivative (B-1) as depicted below.

Reacting compounds of formula (B-1) with a lithium base followed by subsequent addition of dimethylformamide (DMF) as described in e.g. WO 2012/058116 thus yields compounds of formula (B-2) which after reduction with e.g. a hydride reagent such as sodium borohydride yield (B-3) as described e.g. in WO 2012/022681.

Alternatively, compounds of formula (B-1) can also be treated with aldehydes e.g. acetaldehyde after reaction with a lithium base to directly yield compounds of formula (B-4) as described in e.g. Y. Zhang, J. P. Burgess, M. Brackeen, A. Gilliam, S. W. Mascarella, K. Page, H. H. Seltzman, B. F. Thomas, J. Med. Chem. 2008, Si, 3526-3539. Furthermore, various nucleophiles can be reacted with intermediates of formula (B-2) to yield mono- or disubstituted alcohols of formula (B-4) as described in e.g. J. A. Malona, K. Cariou, W. T. Spencer III, A. J. Frontier, J. Org. Chem. 2012, 77, 1891-1908.

In another embodiment, compounds of formula (B-3) or (B-4) can be converted into compounds of formula (B-5) by means of activating the hydroxyl group e.g. via mesylation or tosylation as described in WO 2012/085645. Alternatively, they can be treated with phosphortribromide to convert the hydroxyl group into the respective bromide as described in WO 2012/022487.

In yet other embodiments, compounds of formula (B) with p=1 like e.g. (B-6), (B-11), (B-12) or (B15) can be obtained starting from the respective phenyl acetic acid derivatives of formula (B-7), (B-9) or (B-13) as depicted in Schemes D to F.

α-Alkylation can be employed to introduce $R^3$ and $R^4$ substituents as described in e.g. WO 2012/058134. Substituents and $R^2$ can be introduced, for example, by treatment of compounds of formula (B-8), (B-9), (B-10) or (B-14) with e.g. hydride reagents or Grignard reagents as described in e.g. A. K. Ghosh, C. D. Martyr, C.-X. Xu, Org. Lett. 2012, 14, 2002-2005.

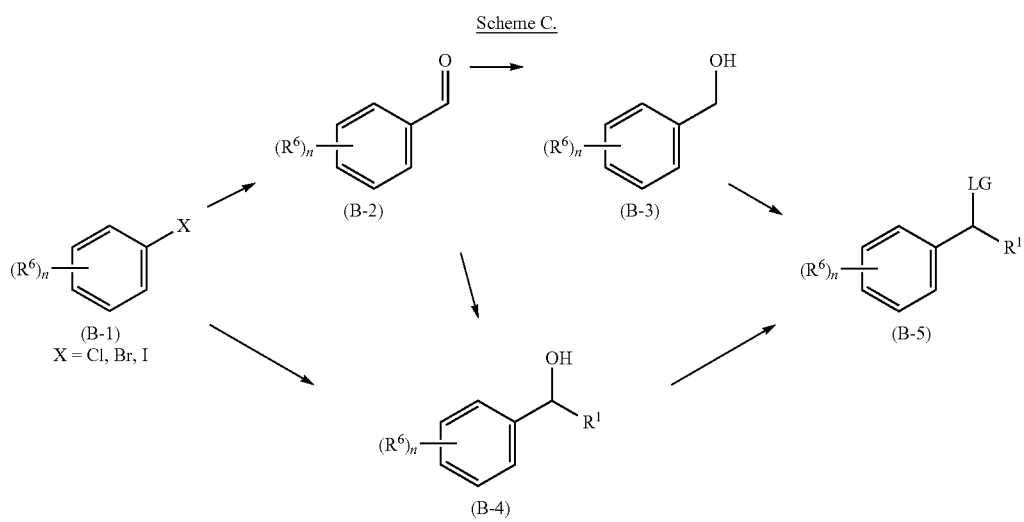

n = 1, 2, 3, 4 or 5

Scheme D.

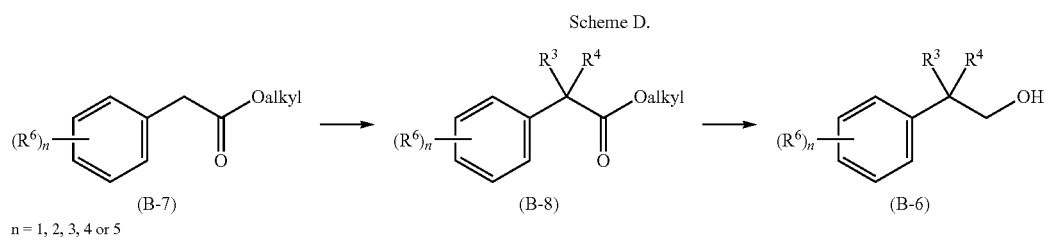

(B-7)    (B-8)    (B-6)

n = 1, 2, 3, 4 or 5

Scheme E.

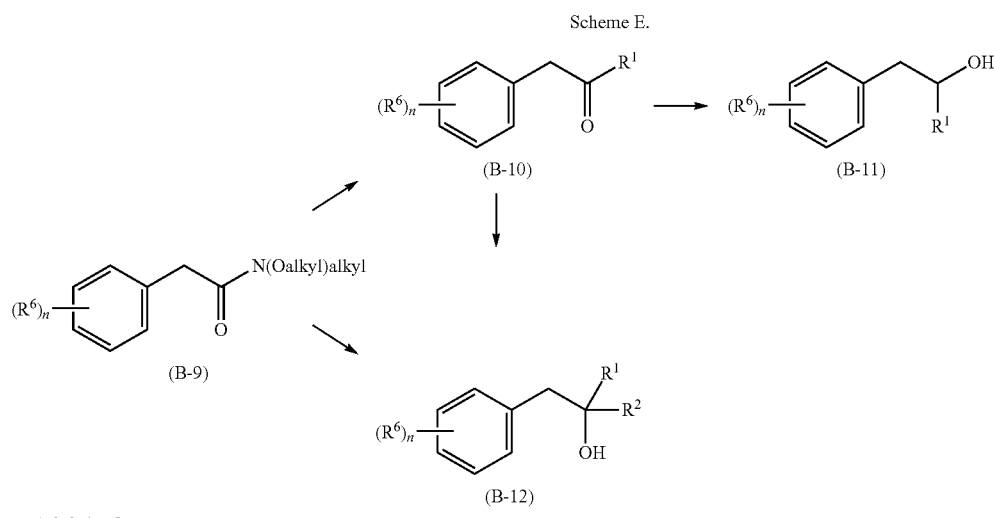

(B-9)    (B-10)    (B-11)

(B-12)

n = 1, 2, 3, 4 or 5

Scheme F.

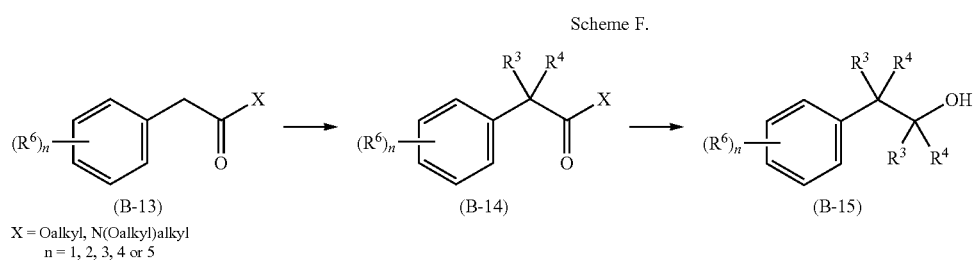

(B-13)    (B-14)    (B-15)

X = Oalkyl, N(Oalkyl)alkyl
n = 1, 2, 3, 4 or 5

The alcohols of formula (B-6), (B-11), (B-12) or (B15) can be further activated by similar methods as described above.

Iodo compounds of formula (A-1), chloro, bromo or iodo compounds of formula (B-1) as well as phenyl acetic acid derivatives needed for compounds of formula (B-7), (B-9) or (B-13) can be purchased or synthesized according to known literature methods.

As a rule, the compounds of formula (I) can be prepared by the methods described above. If individual compounds cannot be prepared via the above-described routes, they can be prepared by derivatization of other compounds (I) or by customary modifications of the synthesis routes described. This applies also to compounds of formula (I) wherein Q is unsubstituted or substituted cycloalkyl or cycloalkenyl. For example, in individual cases, certain compounds (I) can advantageously be prepared from other compounds (I) by ester hydrolysis, amidation, esterification, ether cleavage, olefination, reduction, oxidation and the like.

The reaction mixtures are worked up in the customary manner, for example by mixing with water, separating the phases, and, if appropriate, purifying the crude products by chromatography, for example on alumina or silica gel. Some of the intermediates and end products may be obtained in the form of colorless or pale brown viscous oils, which are freed or purified from volatile components under reduced pressure and at moderately elevated temperature. If the intermediates and end products are obtained as solids, they may be purified by recrystallization or trituration with an appropriate solvent.

In one embodiment, the method for preparing a compound of formula (I) according to the invention or a salt thereof, comprises the step of reacting a compound of formula (XI) with a compound of formula (XII) optionally in the presence of a base.

In another embodiment the reaction of the compound of formula (XI) with the compound of formula (XII) is carried out in the absence of a base.

In another embodiment the reaction of the compound of formula (XI) with the compound of formula (XII) is carried out in the presence of a base.

Preferred, more preferred, even more preferred and particularly preferred compounds of formula (XI) are the ones leading to the respective preferred, more preferred, even more preferred and particularly preferred compounds of formula (I).

Preferred, more preferred, even more preferred and particularly preferred compounds of formula (XII) are the ones leading to the respective preferred, more preferred, even more preferred and particularly preferred compounds of formula (I).

Preference is given to compounds of formula (XII) wherein is halogen or $OS(O)_2R^*$; and $R^*$ is $C_1$-$C_6$-alkyl, $C_1$-$C_6$-haloalkyl, $C_1$-$C_6$-nitroalkyl, $C_1$-$C_6$-alkoxy-$C_1$-$C_6$-alkyl, $C_3$-$C_6$-cycloalkyl, phenyl or phenyl-$C_1$-$C_6$-alkyl, wherein each phenyl is independently unsubstituted or substituted with up to 5 substituents selected from halogen, CN, $NO_2$, $C_1$-$C_6$-alkyl, $C_1$-$C_6$-haloalkyl or $C_1$-$C_6$-alkoxy.

Particular preference is given to compounds of formula (XII) wherein

L is Cl, Br, I or $OS(O)_2R^*$; and $R^*$ is $C_1$-$C_6$-alkyl, $C_1$-$C_6$-haloalkyl or phenyl, wherein phenyl is unsubstituted or 5 substituted with up to 5 substituents selected from halogen, $NO_2$, $C_1$-$C_6$-alkyl or $C_1$-$C_6$-alkoxy.

Very particular preference is given to compounds of formula (XII) wherein

L is Cl, Br or $OS(O)_2R^*$; and $R^*$ is Me, $CF_3$, $C_4F_9$, phenyl or toluyl.

The molar ratio of the compound of formula (XI) to the compound of formula (XII) is generally in the range of 1:0.5-2, preferably in the range of 1:0.5-1.5, more preferably in the range of 1:0.8-1.2.

Examples of suitable bases are carbonates such as lithium carbonate, sodium carbonate, potassium carbonate, cesium carbonate, magnesium carbonate, calcium carbonate, barium carbonate; hydrogen carbonates such as lithium hydrogen carbonate, sodium hydrogen carbonate, potassium hydrogen carbonate; hydroxides such as lithium hydroxide, sodium hydroxide, potassium hydroxide, magnesium hydroxide, calcium hydroxide, barium hydroxide, aluminum hydroxide; oxides such as lithium oxide, sodium oxide, potassium oxide, magnesium oxide, calcium oxide, barium oxide, iron oxide, silver oxide; hydrides such as lithium hydride, sodium hydride, potassium hydride, calcium hydride; phosphates such as potassium phosphate, calcium phosphate; alkoxides such sodium, potassium or magnesium alkoxides; nitrogen-containing bases such as triethylamine, trimethylamine, N-ethyl-diisopropylamine, triisopropylamine, ammonia, pyridine, lutidine, collidine, 4-(dimethylamino)pyridine (DMAP), imidazole, 1,8-diazabicyclo[5.4.0]undec-7-ene (DBU) or 1,5-diazabicyclo[4.3.0]-5-ene (DBN).

Preferred bases include carbonates and hydrides.

Particularly preferred bases include potassium carbonate, cesium carbonate and sodium hydride.

The term base as used herein also includes mixtures of two or more, preferably two of the above compounds. Particular preference is given to the use of one base.

The molar ratio of the compound of formula (XI) to the base is generally in the range of 1:0.8-3, preferably in the range of 1:1-2, more preferably in the range of 1:1-1.5.

Preferably, the reaction of the compound of formula (XI) with the compound of formula (XII) in the presence of a base is carried out in a solvent.

Examples of suitable solvents are dipolar aprotic solvents such as N,N-dimethylformamide (DMF), N,N-dimethylacetamide (DMAc), 1-methyl-2-pyrrolidinone (NMP), 1,3-dimethyl-2-imidazolidinone (DMI), N,N'-dimethylpropylene urea (DMPU), dimethyl sulfoxide (DMSO), sulfolane, acetonitrile, benzonitrile, acetone, methyl ethyl ketone, methyl butyl ketone, methyl isobutyl ketone, cyclohexanone, nitromethane, nitroethane, nitrobenzene; esters such as ethyl acetate, butyl acetate, isobutyl acetate; ethers such as diethylether, dibutylether, tert-butyl methyl ether (TBME), 1,2-dimethoxyethane, tetrahydrofuran (THF), cyclopentyl methyl ether, 1,4-dioxane; alcohols such as methanol, ethanol, isopropanol, 1-butanol, 2-butanol, isobutanol, tert-butanol, hexafluoro isopropanol; halogenated hydrocarbons such as dichloromethane, dichloroethane, carbon tetrachloride; aliphatic hydrocarbons such as hexane, cyclohexane; aromatic hydrocarbons such as benzene, toluene, xylenes, mesitylene, chlorobenzene.

Preferred solvents include acetone, DMF, DMAc, 1,2-dimethoxyethane, DMI, dichloromethane, di ethyl ether and THF.

Particularly preferred solvents include acetone, diethylether and THF.

The term solvent as used herein also includes mixtures of two or more of the above compounds.

The reaction of the compound of formula (XI) with the compound of formula (XII) in the presence of a base is generally carried out at a temperature in the range of from −40 to 80° C., preferably in the range of from −20 to 40° C., more preferably in the range of from 0 to 30° C.

Veterinary Compositions:

In one embodiment of the invention, the compounds of formula (I) may be administered to an animal in the form of a topical, dermal or subdermal formulation. In another embodiment, the compounds of formula (I) may be administered by the application of an external device to the animal including, but not limited to, an animal ear tag, neck collar or pendant.

Insecticidal or parasiticidal devices, e.g., animal ear tags, neck-worn collars and pendants are a means of controlled application of an a parasiticide. The use of pest strips, collars, bands, and tags which have an insecticide contained throughout the substrate of the final device are described in U.S. Pat. Nos. 3,318,679; 3,944,662; 3,756,200; 3,942,480 and 4,195,075; 4,674,445; 4,767,812; 4,967,698; 5,620,696; 5,342,619; 5,104,569; 6,956,099; and U. S. Patent Publication No. 2006/0288955. Each of the aforementioned patents and patent publication is hereby incorporated herein by reference in its entirety.

The matrix of the external devices according to the invention may be based on polyvinyl chloride (PVC) (see U.S. Pat. Nos. 3,318,769, 3,852,416, 4,150,109, 5,437,869) and other vinyl polymers, to which additives such as plasticizers, pigments, etc. are optionally added. In general, the matrices usually used in the common external devices of ear tags and pesticidal collar type can be used. The external device may include one or more plasticizers including, but not limited to, adipates, phthalates, phosphates and citrates. One or more plasticizers may be added to the polymeric matrix such as PVC. Suitable plasticizers include diethyl phthalate, dioctyl sebacate, dioctyl adipate, diisodecyl phthalate, acetyl tributyl citrate, diethyl phthalate, di-n-butyl phthalate, benzyl butyl phthalate, acetyl tributyl citrate, tricresyl phosphate and 2-ethylhexyl diphenyl phosphate.

In another embodiment, the external device may comprise a polymeric base such as PVC in combination with a first remanent plasticizer as described above and a second plasticizer, in particular according to EP-A-0,539,295 and EP-A-0,537,998. Secondary plasticizers include, but are not limited to, acetyl triethyl citrate, triethyl citrate, triacetin, diethylene glycol monoethyl ether and triphenyl phosphate. In addition, common stabilizers used with polymeric devices may be included in the compositions.

Topical, dermal and subdermal formulations may include, by way of non-limiting example, emulsions, creams, ointments, gels, pastes, powders, shampoos, pour-on formulations, ready-to-use formulations, spot-on solutions and suspensions, dips and sprays. Topical application of an inventive compound of formula (I) or of a composition including at least one inventive compound among active agent(s) therein, in the form of a spot-on, spray-on or pour-on composition, may allow for the inventive compound to be absorbed through the skin to achieve systemic levels. In other embodiments, topical application of the compound of formula (I) or a composition comprising the compound may allow the compound to be distributed through the sebaceous glands or on the surface of the skin achieving levels throughout the coat of the animal. When the compound is distributed through the sebaceous glands, they may act as a reservoir, whereby there may be a long-lasting effect (up to several months) effect.

Spot-on formulations are typically applied in a localized region which refers to an area other than the entire animal. In one embodiment, the location may be between the shoulders. Spot-on formulations are described in, for example, U.S. Pat. Nos. 6,426,333 and 6,395,765, both incorporated herein by reference.

Pour-on formulations of the invention may be applied as a stripe on the back of the animal, e.g. a stripe from head to tail of the animal. Pour-on formulations are described in, for example, U.S. Pat. No. 6,010,710, which is incorporated herein by reference. The topical compositions provide for topical administration of a concentrated solution, suspension, microemulsion or emulsion of the active compounds for intermittent application to the animal.

In some embodiments, pour-on formulations may be advantageously oily, and may comprise a diluent or vehicle and optionally also a solvent (e.g. an organic solvent) for the active ingredient if the latter is not soluble in the diluent. In other embodiments, pour-on formulations may be based on a non-oily vehicle or solvent. For example, some pour-on formulations may be based on an alcoholic solvent (e.g. isopropanol, ethanol, etc.).

Organic solvents that can be used in the topical compositions of the invention include, but are not limited to, acetyltributyl citrate, limonene, glycerol formal, fatty acid esters, acetone, acetonitrile, benzyl alcohol, dimethylacetamide, dimethylformamide, monomethylacetamide, dimethyl sulfoxide, dimethyl isosorbide, dipropylene glycol n-butyl ether, aliphatic alcohols including ethanol, isopropanol, butanol and the like; ethylene glycol monoethyl ether, ethylene glycol monomethyl ether, butyl diglycol, dipropylene glycol monomethyl ether, diethylene glycol monoethyl ether, ethylene glycol, liquid polyoxyethylene glycols (PEGs) of various grades, propylene glycol, propylene carbonate, ethylene carbonate, 2-pyrrolidone, N-methylpyrrolidone, triacetin, $C_1$-$C_{10}$ esters of carboxylic acids and dicarboxylic acids such as butyl or octyl acetate and diisobutyl adipate, and diethyl phthalate, or a mixture of at least two of these solvents.

The solvent will be used in proportion with the concentration of the active agent compound and its solubility in this solvent. It will be sought to have the lowest possible volume. The vehicle makes up the difference of the composition to 100%.

In some embodiments, the vehicle or diluent for the formulations may include dimethyl sulfoxide (DMSO), dimethyl isosorbide, N-methylpyrrolidone, glycol derivatives such as, for example, propylene glycol, glycol ethers, polyethylene glycols or glycerol, or mixtures thereof.

In other embodiments, the vehicle or may include plant oils such as, but not limited to soybean oil, groundnut oil, castor oil, corn oil, cotton oil, olive oil, grape seed oil, sunflower oil, etc.; mineral oils such as, but not limited to, petrolatum, paraffin, silicone, etc.; aliphatic or cyclic hydrocarbons or alternatively, for example, medium-chain (such as $C_8$ to $C_{12}$) triglycerides and medium chain esters of propylene glycol such as those neutral oils sold by the trademark Miglyol®, including Miglyol® 810, Miglyol® 812, Miglyol® 818, Miglyol® 829 and Miglyol® 840.

In another embodiment, the compositions include a mixture of one or more organic solvents together with an oil. In a particular embodiment, the compositions may comprise a combination of N-methylpyrrolidone, dimethyl isosorbide and Miglyol® 840.

In another embodiment of the invention, an emollient and/or spreading and/or film-forming agent may be added. In one embodiment, the emollient and/or spreading and/or film-forming agent may be:

(a) polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, silicone oils, polydiorganosiloxane oils (such as polydimethylsiloxane (PDMS) oils), for example those containing silanol functionalities, or a 45V2 oil, (b) anionic surfactants such as alkaline stearates, sodium, potassium or ammonium stearates; calcium stearate, triethanolamine stearate; sodium abietate; alkyl sulfates (e.g. sodium lauryl sulfate and sodium cetyl sulfate); sodium dodecylbenzenesulfonate, sodium dioctylsulphosuccinate; fatty acids (e.g. those derived from coconut oil), (c) cationic surfactants include water-soluble quaternary ammonium salts of formula $N^+R'R''R'''R''''$, $Y^-$ in which the radicals Rare optionally hydroxylated hydrocarbon radicals and $Y^-$ is an anion of a strong acid such as the halide, sulfate and sulfonate anions; cetyltrimethylammonium bromide is among the cationic surfactants which can be used, (d) amine salts of formula $N^+R'R''R'''$ in which the radicals R are optionally hydroxylated hydrocarbon radicals; octadecylamine hydrochloride is among the amine salt surfactants which can be used, (e) nonionic surfactants such as sorbitan esters, which are optionally polyoxyethylenated (e.g. polysorbate 80), polyoxyethylenated alkyl ethers; polyoxypropylated fatty alcohols such as polyoxypropylene-styrol ether; polyethylene glycol stearate, polyoxyethylenated derivatives of castor oil (including hydrogenated castor oil), polyglycerol esters, polyoxyethylenated fatty alcohols, polyoxyethylenated fatty acids, copolymers of ethylene oxide and propylene oxide, (f) amphoteric surfactants such as the substituted lauryl compounds of betaine; or (g) a mixture of at least two of these agents.

In one embodiment, the emollient used may be in a proportion of from about 0.1 to 50% or 0.25 to 5%, by weight by volume (w/v). In another embodiment, the emollient used may be in a proportion of from about 0.1% to about 30%, about 1% to about 30%, about 1% to about 20%, or about 5% to about 20% (w/v).

In another embodiment of the invention, the composition may be in ready-to-use solution form as is described in U.S. Pat. No. 6,395,765. In addition to the compounds of the invention, the ready-to-use solution may contain a crystallization inhibitor and an organic solvent or a mixture of organic solvents. In some embodiments, water may be included with the organic solvent.

In some embodiments of the invention, the compositions may include a crystallization inhibitor in an amount of about 1 to about 50% (w/v) or about 5 to about 40% (w/v) based on the total weight of the formulation. In other embodiments, the amount of crystallization inhibitor in the inventive formulations may be about 1% to about 30%, about 5% to about 20%, about 1% to about 15%, or about 1% to about 10% (w/v). The type of crystallization inhibitor used in the inventive formulations is not limited as long as it functions to inhibit crystallization of the active agents from the formulation. For example, in certain embodiments of the invention, a solvent or co-solvent of the formulation may also function as a crystallization inhibitor if it sufficiently inhibits the formation of crystals from forming over time when the formulation is administered and absorbed on the animal. Particular mention may be made of benzyl alcohol, N-methylpyrrolidone or propylene carbonate.

Crystallization inhibitors which are useful for the compositions of the invention include, but are not limited to:
(a) polyvinylpyrrolidone, polyvinyl alcohols, copolymers of vinyl acetate and vinylpyrrolidone, polyethylene glycols, benzyl alcohol, dimethylformamide, dimethylacetamide, dimethylsulfoxide, 2-pyrrolidone, N-methylpyrrolidone, mannitol, glycerol, sorbitol or polyoxyethylenated esters of sorbitan; lecithin or sodium carboxymethylcellulose; or acrylic derivatives, such as acrylates or methacrylates or polymers or copolymers thereof, polyethyleneglycols (PEG) or polymers containing polyethyleneglycols, such as glycofurol and the like, and others;
(b) anionic surfactants, such as alkaline stearates (e.g. sodium, potassium or ammonium stearate); calcium stearate or triethanolamine stearate; sodium abietate; alkyl sulfates, which include but are not limited to sodium lauryl sulfate and sodium cetyl sulfate; sodium dodecylbenzenesulfonate or sodium dioctyl sulphosuccinate; or fatty acids (e.g. coconut oil);
(c) cationic surfactants, such as water-soluble quaternary ammonium salts of formula $N^+R'R''R'''R''''Y^-$, in which the R radicals are identical or different optionally hydroxylated hydrocarbon radicals and Y is an anion of a strong acid, such as halide, sulfate and sulfonate anions; cetyltrimethylammonium bromide is one of the cationic surfactants which can be used;
(d) amine salts of formula $N^+R'R''R'''$, in which the R radicals are identical or different optionally hydroxylated hydrocarbon radicals; octadecylamine hydrochloride is one of the cationic surfactants which can be used;
(e) non-ionic surfactants, such as optionally polyoxyethylenated esters of sorbitan, e.g. Polysorbate 80, or polyoxyethylenated alkyl ethers; polyethylene glycol stearate, polyoxyethylenated derivatives of castor oil including polyoxyl hydrogenated castor oil, polyglycerol esters, polyoxyethylenated fatty alcohols, polyoxyethylenated fatty acids or copolymers of ethylene oxide and of propylene oxide;
(f) amphoteric surfactants, such as substituted lauryl compounds of betaine;
(g) a mixture of at least two of the compounds listed in (a)-(f) above; or
(h) an organic solvent or mixture of solvents which inhibit the formation of crystals or amorphous solid after the formulation is administered.

In one embodiment, the crystallization inhibitor will be one of the various grades of polyvinylpyrrolidone (PVP). In another embodiment, the crystallization inhibitor will be a copolymer of vinyl acetate and vinyl pyrrolidone (Copovidone). In another embodiment, the crystallization inhibitor will be a polyoxyethylenated derivative of castor oil including poly oxyl hydrogenated castor oil.

In one embodiment of the invention, a crystallization inhibitor system will be used. Crystallization inhibitor systems may include a mixture of two or more of the crystallization inhibitors described above. In one embodiment, a crystallization inhibitor mixture may include, for example, the combination of a film-forming agent of polymeric type and of a surface-active agent. These agents will be selected from the compounds mentioned above as crystallization inhibitor.

In some embodiments, the organic solvent(s) in the compositions may have a dielectric constant of between about 10 and about 35 or between about 20 and about 30. In other embodiments, the organic solvent may have a dielectric constant of between about 10 and about 40 or between about 20 and about 30. The content of this organic solvent or mixture of solvents in the overall composition is not limited and will be present in an amount sufficient to dissolve the desired components to a desired concentration. As discussed above, in some embodiments the organic solvent may also function as a crystallization inhibitor in the formulation so that a separate component to inhibit crystallization of the active is not required.

In some embodiments, one or more of the organic solvent(s) may have a boiling point of below about 100° C., or below about 80° C. In other embodiments, the organic solvent(s) may have a boiling point of below about 300° C., below about 250° C., below about 230° C., below about 210° C. or below about 200° C.

In some embodiments where there is a mixture of solvents, i.e. a solvent and one or more co-solvent(s), the solvents may be present in the composition in a weight/weight (W/W) ratio of about 1/50 to about 1/1. Typically the solvents will be in a ratio of about 1/30 to about 1/1, about 1/20 to about 1/1, or about 1/15 to about 1/1 by weight. Preferably, the two solvents will be present in a weight/weight ratio of about 1/15 to about 1/2. In some embodiments, at least one of the solvents present may act as to improve solubility of the active agent or as a drying promoter. In particular embodiments, at least one of the solvents will be miscible with water.

In one embodiment of the film-forming agent, the agents are of the polymeric type which include but are not limited to the various grades of polyvinylpyrrolidone, polyvinyl alcohols, and copolymers of vinyl acetate and of vinylpyrrolidone.

In one embodiment of the surface-active agents, the agents include but are not limited to, those made of non-ionic surfactants; in another embodiment of the surface active agents, the agent is a polyoxyethylenated esters of sorbitan and in yet another embodiment of the surface-active agent, the agents include the various grades of polysorbate, for example Polysorbate 80.

In another embodiment of the invention, the film-forming agent and the surface-active agent may be incorporated in similar or identical amounts within the limit of the total amounts of crystallization inhibitor mentioned elsewhere.

The crystallization inhibitor inhibits the formation of crystals on the coat, and improves the maintenance of the cosmetic appearance of the skin or fur; that is to say without a tendency towards sticking or towards a sticky appearance, despite the relatively high concentration of active material. Substances other than those mentioned herein may be used as crystallization inhibitors in the present invention.

In one embodiment, the effectiveness of the crystallization inhibitor may be determined by a test according to which 0.3 mL of a solution comprising 10% (w/v) of the active agent in an appropriate solvent as defined above, and 10% (w/v) of the compound acting as a crystallization inhibitor are placed on a glass slide at 20° C. for 24 hours, after which fewer than 10 crystals, preferably 0 crystals, are seen with the naked eye on the glass slide.

In some embodiments, the compositions of the invention may also comprise an antioxidant intended to inhibit oxidation in air. In some embodiments, the antioxidant may be present in a proportion of about 0.005 to about 1% (w/v), about 0.01 to about 0.1%, or about 0.01 to about 0.05%. In some embodiments, the antioxidants are those conventional in the art and include, but are not limited to, butylated hydroxyanisole (BHA), butylated hydroxytoluene (BHT), ascorbic acid, sodium metabisulphite, propyl gallate, sodium thiosulfate or a mixture of at least two compounds with antioxidant properties.

The formulation adjuvants discussed above are well known to the practitioner in this art and may be obtained commercially or through known techniques. These compositions are generally prepared by simple mixing of the constituents as defined above; advantageously, the starting point is to mix the active material in the main solvent and then the other ingredients or adjuvants are added.

The volume of the formulation applied will depend on the type of animal and the size of the animal as well as the strength of the formulation and the potency of the active agents. In one embodiment, an amount of about 0.5 to about 500 ml of the topical formulation may be applied to the animal depending on the size and weight of the animal.

In some embodiments intended for use on smaller animals (e.g. treatment with spot-on compositions), the volume of the compositions applied may be about 0.1 to about 10 ml, about 0.1 to about 5 ml, about 0.5 ml to about 10 ml, or about 0.3 to about 3 ml.

In other embodiments intended for use on larger animals such as cattle (e.g. treatment with pour-on compositions), the volume of the composition applied to the animal will be larger. For larger volume applications, the liquid composition is typically applied along the backline from the withers to the tail of the animal. In some embodiments, the volume will be between about 5 ml to about 50 ml. In other embodiments, the volume applied will be about 10 ml to about 200 ml, about 10 ml to about 150 ml or about 10 ml to about 100 ml. In yet other embodiments, the volume applied will be about 10 ml to about 80 ml, about 10 ml to about 70 ml, about 10 ml to about 60 ml or about 10 ml to about 50 ml.

Dosage forms may typically contain from about 0.1 mg to about 10 g of the active ingredient, depending on the product and the animal to which the composition is to be administered. In some embodiments, the dosage forms may contain from about 1 g to about 10 g, about 1 g to about 8 g, about 1 g to about 5 g, or about 1 g to about 3 g.

In other embodiments, the dosage form may contain about 0.5 mg to about 5 g of an active agent. In one embodiment of the dosage form, the dosage may contain from about 1 mg to about 500 mg of an active agent, about 1 mg to about 25 mg, about 1 mg to about 50 mg, about 10 mg to about 100 mg, about 20 mg to about 200 mg, about 50 mg to about 300 mg, about 50 mg to about 400 mg, about 100 mg to about 500 mg, about 100 mg to about 600 mg, about 100 mg to about 800 mg, or about 100 mg to about 1 gram.

In one embodiment of the invention, the active agent may be present in the formulation at a concentration of about 0.1 to about 50% weight/volume. In other embodiments, the concentration of the compound of formula (I) in the composition will be about 1% (w/v) to about 20% (w/v), about 5% (w/v) to about 20% (w/v), about 1% (w/v) to about 10% (w/v) or about 5% (w/v) to about 15% (w/v). In another embodiment of the invention, the active agent may be present in the formulation as a concentration from about 0.1 to about 2% (w/v). In yet another embodiment of the invention, the active agent may be present in the formulation as a concentration from about 0.25 to about 1.5% (w/v). In still another embodiment of the invention, the active agent may be present in the formulation as a concentration about 1% (w/v), about 5% (w/v), about 10% (w/v), about 15% (w/v) or about 20% (w/v).

Additional pharmaceutical, pesticidal or veterinarily active ingredients, which include, but are not limited to, parasiticidals including acaricides, anthelmintics, endectocides and insecticides, may also be added to the compositions of the invention. Anti-parasitic agents may include both ectoparasiticidal and endoparasiticidal agents. Veterinary pharmaceutical agents are well-known in the art (see e.g. *Plumb' Veterinary Drug Handbook*, 5$^{th}$ Edition, ed. Donald C. Plumb, Blackwell Publishing, (2005) or *The Merck Veterinary Manual*, 9$^{th}$ Edition, (January 2005)) and include but are not limited to acarbose, acepromazine maleate, acetaminophen, acetazolamide, acetazolamide sodium, acetic acid, acetohydroxamic acid, acetylcysteine, acitretin, acyclovir, albendazole, albuterol sulfate, alfentanil, allopurinol, alprazolam, altrenogest, amantadine, amikacin sulfate, aminocaproic acid, aminopentamide hydrogen sulfate, aminophylline/theophylline, amiodarone, amitraz, amitriptyline, amlodipine besylate, ammonium chloride, ammonium molybdenate, amoxicillin, amoxicillin, clavulanate potassium, amphotericin B desoxycholate, amphotericin B lipid-based, ampicillin, amprolium, antacids (oral), antivenin, apomorphione, apramycin sulfate, ascorbic acid, asparaginase, aspiring, atenolol, atipamezole, atracurium besylate, atropine sulfate, aurnofin, aurothioglucose, azaperone, azathioprine, azithromycin, baclofen, barbituates, benazepril, betamethasone, bethanechol chloride, bisacodyl, bismuth subsalicylate, bleomycin sulfate, boldenone undecylenate, bromides, bromocriptine mesylate, budenoside, buprenorphine, buspirone, busulfan, butorphanol tartrate, cabergoline, calcitonin salmon, calcitrol, calcium salts, captopril, carbenicillin indanyl sodium, carbimazole, carboplatin, carnitine, carprofen, carvedilol, cefadroxil, cefazolin sodium, cefixime, cefoperazone sodium, cefotaxime sodium, cefotetan disodium, cefoxitin sodium, cefpodoxime proxetil, ceftazidime, ceftiofur sodium, ceftiofur, ceftiaxone sodium, cephalexin, cephalosporins, cephapirin, charcoal (activated), chlorambucil, chloramphenicol, chlordiazepoxide, chlordiazepoxide+/−clidinium bromide, chlorothiazide, chlorpheniramine maleate, chlorpromazine, chlorpropamide, chlortetracycline, chorionic gonadotropin (HCG), chromium, cimetidine, ciprofloxacin, cisapride, cisplatin, citrate salts, clarithromycin, clemastine fumarate, clenbuterol, clindamycin, clofazimine, clomipramine, claonazepam, clonidine, cloprostenol sodium, clorazepate dipotassium, clorsulon, cloxacillin, codeine phosphate, colchicine, corticotropin (ACTH), cosyntropin, cyclophosphamide, cyclosporine, cyproheptadine, cytarabine, dacarbazine, dactinomycin/actinomycin D, dalteparin sodium, danazol, dantrolene sodium, dapsone, decoquinate, deferoxamine mesylate, deracoxib, deslorelin acetate, desmopressin acetate, desoxycorticosterone pivalate, detomidine, dexamethasone, dexpanthenol, dexraazoxane, dextran, diazepam, diazoxide (oral), dichlorphenamide, dichlorvos, diclofenac sodium, dicloxacillin, diethylcarbamazine citrate, diethylstilbestrol (DES), difloxacin, digoxin, dihydrotachysterol (DHT), diltiazem, dimenhydrinate, dimercaprol/BAL, dimethyl sulfoxide, dinoprost tromethamine, diphenylhydramine, disopyramide phosphate, dobutamine, docusate/DSS, dolasetron mesylate, domperidone, dopamine, doramectin, doxapram, doxepin, doxorubicin, doxycycline, edetate calcium disodium. calcium EDTA, edrophonium chloride, enalapril/enalaprilat, enoxaparin sodium, enrofloxacin, ephedrine sulfate, epinephrine, epoetin/erythropoietin, eprinomectin, epsiprantel, erythromycin, esmolol, estradiol cypionate, ethacrynic acid/ethacrynate sodium, ethanol (alcohol), etidronate sodium, etodolac, etomidate, euthanasia agents w/pentobarbital, famotidine, fatty acids (essential/omega), felbamate, fenbendazole, fentanyl, ferrous sulfate, filgrastim, finasteride, fipronil, florfenicol, fluconazole, flucytosine, fludrocortisone acetate, flumazenil, flumethasone, flunixin meglumine, fluorouracil (5-FU), fluoxetine, fluticasone propionate, fluvoxamine maleate, fomepizole (4-MP), furazolidone, furosemide, gabapentin, gemcitabine, gentamicin sulfate, glimepiride, glipizide, glucagon, glucocorticoid agents, glucosamine/chondroitin sulfate, glutamine, glyburide, glycerine (oral), glycopyrrolate, gonadorelin, grisseofulvin, guaifenesin, halothane, hemoglobin glutamer-200 (Oxyglobin®), heparin, hetastarch, hyaluronate sodium, hydrazaline, hydrochlorothiazide, hydrocodone bitartrate, hydrocortisone, hydromorphone, hydroxyurea, hydroxyzine, ifosfamide, imidacloprid, imidocarb dipropinate, imipenem-cilastatin sodium, imipramine, inamrinone lactate, insulin, interferon alfa-2a (human recombinant), iodide (sodium/potassium), ipecac (syrup), ipodate sodium, iron dextran, isoflurane, isoproterenol, isotretinoin, isoxsuprine, itraconazole, ivermectin, kaolin/pectin, ketamine, ketoconazole, ketoprofen, ketorolac tromethamine, lactulose, leuprolide, levamisole, levetiracetam, levothyroxine sodium, lidocaine, lincomycin, liothyronine sodium, lisinopril, lomustine (CCNU), lufenuron, lysine, magnesium, mannitol, marbofloxacin, mechlorethamine, meclizine, meclofenamic acid, medetomidine, medium chain triglycerides, medroxyprogesterone acetate, megestrol acetate, melarsomine, melatonin, meloxican, melphalan, meperidine, mercaptopurine, meropenem, metformin, methadone, methazolamide, methenamine mandelate/hippurate, methimazole, methionine, methocarbamol, methohexital sodium, methotrexate, methoxyflurane, methylene blue, methylphenidate, methylprednisolone, metoclopramide, metoprolol, metronidaxole, mexiletine, mibolerlone, midazolam milbemycin oxime, mineral oil, minocycline, misoprostol, mitotane, mitoxantrone, morantel tartrate, morphine sulfate, moxidectin, naloxone, mandrolone decanoate, naproxen, narcotic (opiate) agonist analgesics, neomycin sulfate, neostigmine, niacinamide, nitazoxanide, nitenpyram, nitrofurantoin, nitroglycerin, nitroprusside sodium, nizatidine, novobiocin sodium, nystatin, octreotide acetate, olsalazine sodium, omeprozole, ondansetron, opiate antidiarrheals, orbifloxacin, oxacillin sodium, oxazepam, oxfendazole, oxibutynin chloride, oxymorphone, oxytretracycline, oxytocin, pamidronate disodium, pancreplipase, pancuronium bromide, paromomycin sulfate, parozetine, pencillamine, penicillins including penicillin G and penicillin V potassium, pentazocine, pentobarbital sodium, pentosan polysulfate sodium, pentoxifylline, pergolide mesylate, phenobarbital, phenoxybenzamine, pheylbutazone, phenylephrine, phenypropanolamine, phenytoin sodium, pheromones, parenteral phosphate, phytonadione/vitamin K-1, pimobendan, piperazine, pirlimycin, piroxicam, polysulfated glycosaminoglycan, ponazuril, potassium chloride, pralidoxime chloride, praziquantel, prazosin, prednisolone/prednisone, primidone, procainamide, procarbazine, prochlorperazine, propantheline bromide, Propionibacterium acnes injection, propofol, propranolol, protamine sulfate, pseudoephedrine, psyllium hydrophilic mucilloid, pyrantel pamoate, pyridostigmine bromide, pyrilamine maleate, pyrimethamine, quinacrine, quinidine, ranitidine, rifampin, s-adenosyl-methionine (SAMe), saline/hyperosmotic laxative, selamectin, selegiline/1-deprenyl, sertraline, sevelamer, sevoflurane, silymarin/milk thistle, sodium bicarbonate, sodium polystyrene sulfonate, sodium stibogluconate, sodium sulfate, sodum thiosulfate, somatotropin, sotalol, spectinomycin, spironolactone, stanozolol, streptokinase, streptozocin, succimer, succinylcholine chloride, sucralfate, sufentanil citrate, sulfachlorpyridazine sodium, sulfadiazine/trimethroprim, sulfamethoxazole/trimethoprim, sulfadimentoxine, sulfadimethoxine/ormetoprim, sulfasalazine, taurine, tepoxaline, terbinafline, terbutaline sulfate, testosterone, tetracycline, thiabendazole, thiacetarsamide sodium, thiamine, thioguanine, thiopental sodium, thiotepa, thyrotropin, tiamulin, ticarcilin dis odium, tiletamine/zolazepam, tilmocsin, tiopronin, tobramycin sulfate, tocainide, tolazoline, telfenamic acid, topiramate, tramadol, trimcinolone acetonide, trientine, trilostane, trimepraxine tartrate w/prednisolone, tripelennamine, tylosin, urdosiol, valproic acid, vanadium, vancomycin, vasopressin, vecuronium bromide, verapamil, vinblastine sulfate, vincristine sulfate, vitamin E/selenium, warfarin sodium, xylazine, yohimbine, zafirlukast, zidovudine (AZT), zinc acetate/zinc sulfate, zonisamide and mixtures thereof.

In one embodiment of the invention, arylpyrazole compounds such as phenylpyrazoles, known in the art may be combined with the compounds of formula (I) in the compositions of the invention. Examples of such arylpyrazole compounds include but are not limited to those described in U.S. Pat. Nos. 5,232,940; 6,001,384; 6,010,710; 6,083,519; 6,096,329; 6,174,540; 6,685,954 and 6,998,131 (all of which are incorporated herein by reference, each assigned to Merial, Ltd., Duluth, Ga.).

In another embodiment of the invention, one or more macrocyclic lactones, which act as an acaricide, anthelmintic agent and/or insecticide, can be added to the compositions of the invention.

The macrocyclic lactones include, but are not limited to, avermectins such as abamectin, dimadectin, doramectin, emamectin, eprinomectin, ivermectin, latidectin, lepimectin, selamectin and ML-1,694,554, and milbemycins such as milbemectin, milbemycin D, milbemycin oxime, moxidectin and nemadectin. Also included are the 5-oxo and 5-oxime derivatives of said avermectins and milbemycins.

The macrocyclic lactone compounds are known in the art and can easily be obtained commercially or through synthesis techniques known in the art. Reference is made to the widely available technical and commercial literature. For avermectins, ivermectin and abamectin, reference may be made, for example, to the work "Ivermectin and Abamectin", 1989, by M. H. Fischer and H. Mrozik, William C. Campbell, published by Springer Verlag., or Albers-Schönberg et al. (1981), "Avermectins Structure Determination", J. Am. Chem. Soc., 103, 4216-4221. For doramectin, "Veterinary Parasitology", vol. 49, No. 1, July 1993, 5-15 may be consulted. For milbemycins, reference may be made, inter alia, to Davies H. G. et al., 1986, "Avermectins and Milbemycins", Nat. Prod. Rep., 3, 87-121, Mrozik H. et al., 1983, Synthesis of Milbemycins from Avermectins, Tetrahedron Lett., 24, 5333-5336, U.S. Pat. No. 4,134,973 and EP 0 677 054.

Macrocyclic lactones are either natural products or are semi-synthetic derivatives thereof. The structure of the avermectins and milbemycins are closely related, e.g., by sharing a complex 16-membered macrocyclic lactone ring. The natural product avermectins are disclosed in U.S. Pat. No. 4,310,519 and the 22,23-dihydro avermectin compounds are disclosed in U.S. Pat. No. 4,199,569. Mention is also made of U.S. Pat. Nos. 4,468,390, 5,824,653, EP 0 007 812 A1, U.K. Patent Specification 1 390 336, EP 0 002 916, and New Zealand Patent No. 237 086, inter alia. Naturally occurring milbemycins are described in U.S. Pat. No. 3,950,360 as well as in the various references cited in "The Merck Index" 12$^{th}$ ed., S. Budavari, Ed., Merck & Co., Inc. Whitehouse Station, N.J. (1996). Latidectin is described in the "International Nonproprietary Names for Pharmaceutical Substances (INN)", *WHO Drug Information*, vol. 17, no. 4, pp. 263-286, (2003). Semisynthetic derivatives of these classes of compounds are well known in the art and are described, for example, in U.S. Pat. Nos. 5,077,308, 4,859,657, 4,963,582, 4,855,317, 4,871,719, 4,874,749, 4,427,663, 4,310,519, 4,199,569, 5,055,596, 4,973,711, 4,978,677, 4,920,148 and EP 0 667 054 (all patents mentioned above with reference to avermectins and milbemycins are incorporated herein by reference).

In another embodiment of the invention, the invention comprises a topical composition comprising a compound of formula (I) in combination with a class of acaricides or insecticides known as insect growth regulators (IGRs). Compounds belonging to this group are well known to the practitioner and represent a wide range of different chemical classes. These compounds all act by interfering with the development or growth of the insect pests. Insect growth regulators are described, for example, in U.S. Pat. Nos. 3,748,356, 3,818,047, 4,225,598, 4,798,837, 4,751,225, EP 0 179 022 or U.K. 2 140 010 as well as U.S. Pat. Nos. 6,096,329 and 6,685,954 (all incorporated herein by reference).

In one embodiment the IGR is a compound that mimics juvenile hormone. Examples of juvenile hormone mimics include azadirachtin, diofenolan, fenoxycarb, hydroprene, kinoprene, methoprene, pyriproxyfen, tetrahydroazadirachtin and 4-chloro-2(2-chloro-2-methyl-propyl)-5-(6-iodo-3-pyridylmethoxy)pyridazin-3(2H)-one.

In another embodiment, the IGR compound is a chitin synthesis inhibitor. Chitin synthesis inhibitors include chlorofluazuron, cyromazine, diflubenzuron, fluazuron, flucycloxuron, flufenoxuron, hexaflumoron, lufenuron, tebufenozide, teflubenzuron, triflumoron, novaluron, 1-(2,6-difluorobenzoyl)-3-(2-fluoro-4-(trifluoromethyl)phenylurea, 1-(2,6-difluoro-benzoyl)-3-(2-fluoro-4-(1,1,2,2-tetrafluoroethoxy)-phenylurea and 1-(2,6-difluorobenzoyl)-3-(2-fluoro-4-trifluoromethyl)phenylurea.

In yet another embodiment of the invention, adulticide insecticides and acaricides can also be added to the composition of the invention. These include pyrethrins (which include cinerin I, cinerin II, jasmolin I, jasmolin II, pyrethrin I, pyrethrin II and mixtures thereof) and pyrethroids. Pyrethroid active agents include, but are not limited to, permethrin, cypermethrin, alphacypermethrin, deltamethrin, cyfluthrin, cyphenothrin and flumethrin.

Also included are carbamate insecticides including, but are not limited to, benomyl, carbanolate, carbaryl, carbofuran, meththiocarb, metolcarb, promacyl, propoxur, aldicarb, butocarboxim, oxamyl, thiocarboxime and thiofanox.

In some embodiments, the compositions of the invention may include one or more antinematodal agents including, but not limited to, active agents in the benzimidazoles, imidazothiazoles, tetrahydropyrimidines, and organophosphate class of compounds. In some embodiments, benzimidazoles including, but not limited to, thiabendazole, cambendazole, parbendazole, oxibendazole, mebendazole, flubendazole, fenbendazole, oxfendazole, albendazole, cyclobendazole, febantel, thiophanate and its o,o-dimethyl analogue may be included in the compositions.

In other embodiments, the compositions may include an imidazothiazole compounds including, but not limited to, tetramisole, levamisole and butamisole. In still other embodiments, the compositions of the invention may include tetrahydropyrimidine active agents including, but not limited to, pyrantel, oxantel, and morantel. Suitable organophosphate active agents include, but are not limited to, fenthion, coumaphos, trichlorfon, haloxon, naftalofos and dichlorvos, heptenophos, mevinphos, monocrotophos, TEPP, and tetrachlorvinphos.

In other embodiments, the compositions may include the antinematodal compounds phenothiazine and piperazine as the neutral compound or in various salt forms, diethylcarbamazine, phenols such as disophenol, arsenicals such as arsenamide, ethanolamines such as bephenium, thenium closylate, and methyridine; cyanine dyes including pyrvinium chloride, pyrvinium pamoate and dithiazanine iodide; isothiocyanates including bitoscanate, suramin sodium, phthalofyne, and various natural products including, but not limited to, hygromycin B, α-santonin and kainic acid.

In other embodiments, the compositions of the invention may include antitrematodal agents. Suitable antitrematodal agents include, but are not limited to, the miracils such as miracil D and mirasan; praziquantel, clonazepam and its 3-methyl derivative, oltipraz, lucanthone, hycanthone, oxamniquine, amoscanate, niridazole, nitroxynil, various bisphenol compounds known in the art including hexachlorophene, bithionol, bithionol sulfoxide and menichlopholan; various salicylanilide compounds including tribromsalan, oxyclozanide, clioxanide, rafoxanide, brotianide, bromoxanide and closantel; triclabendazole, diamfenetide, clorsulon, hetolin and emetine.

Anticestodal compounds may also be advantageously used in the compositions of the invention including, but not limited to, arecoline in various salt forms, bunamidine, niclosamide, nitroscanate, paromomycin and paromomycin II.

In yet other embodiments, the compositions of the invention may include other active agents that are effective against arthropod parasites. Suitable active agents include, but are not limited to, bromocyclen, chlordane, DDT, endosulfan, lindane, methoxychlor, toxaphene, bromophos, bromophosethyl, carbophenothion, chlorfenvinphos, chlorpyrifos, crotoxyphos, cythioate, diazinon, dichlorenthion diemthoate, dioxathion, ethion, famphur, fenitrothion, fenthion, fospirate, iodofenphos, malathion, naled, phosalone, phosmet, phoxim, propetamphos, ronnel, stirofos, allethrin, cyhalothrin, cypermethrin, deltamethrin, fenvalerate, flucythrinate, permethrin, phenothrin, pyrethrins, resmethrin, benzyl benzoate, carbon disulfide, crotamiton, diflubenzuron, diphenylamine, disulfiram, isobornyl thiocyanato acetate, methoprene, monosulfiram, pirenonylbutoxide, rotenone, triphenyltin acetate, triphenyltin hydroxide, deet, dimethyl phthalate, and the compounds 1,5a,6,9,9a,9b-hexahydro-4a (4H)-dibenzofurancarboxaldehyde (MGK-11), 2-(2-ethylhexyl)-3a,4,7,7a-tetrahydro-4,7-methano-1H-isoindole-1,3 (2H)dione (MGK-264), dipropyl-2,5-pyridinedicarboxylate (MGK-326) and 2-(octylthio)ethanol (MGK-874).

An antiparasitic agent that can be combined with the compound of the invention to form a composition can be a biologically active peptide or protein including, but not limited to, depsipeptides, which act at the neuromuscular junction by stimulating presynaptic receptors belonging to the secretin receptor family resulting in the paralysis and death of parasites. In one embodiment of the depsipeptide, the depsipeptide is emodepside (see Willson et al., *Parasitology*, January 2003, 126(Pt 1):79-86). In another embodiment, the depsipeptide is PF1022A or an analog of this compound.

In another embodiment, the compositions of the invention may comprise an active agent from the neonicotinoid class of pesticides. The neonicotinoids bind and inhibit insect specific nicotinic acetylcholine receptors. In one embodiment, the neonicotinoid insecticidal agent that can be combined with an isoxazoline compound to form a topical composition of the invention is imidacloprid. Imidacloprid is a well-known neonicotinoid active agent and is the key active ingredient in the topical parasiticide products Advantage®, Advantage® II, K9 Advantix®, and K9 Advantix® II sold by Bayer Animal Health. Agents of this class are described, for example, in U.S. Pat. No. 4,742,060 or in EP 0 892 060.

In another embodiment, the topical compositions of the invention may comprise nitenpyram, another active agent of the neonicotinoid class of pesticides. Nitenpyram is the active ingredient in the oral product CAPSTAR™ Tablets sold by Novartis Animal Health.

Nitenpyram is active against adult fleas when given daily as an oral tablet. Nitenpyram works by interfering with normal nerve transmission and leads to the death of the insect. Nitenpyram has a very fast onset of action against fleas. For example, CAPSTAR™ Tablets begin to act against fleas in as early as 30 minutes after administration and is indicated for use as often as once a day.

In certain embodiments, an insecticidal agent that can be combined with the compositions of the invention is a semicarbazone, such as metaflumizone.

In another embodiment, the compositions of the invention may advantageously include one or more isoxazoline active agents known in the art. These active agents are described in, for example, U.S. Pat. Nos. 7,964,204; 8,410,153; 8,318,757; 8,193,221; 8,653,116; 8,633,134; US 2012/030841; U.S. Pat. Nos. 8,372,867; 8,618,126; US 2008/0262057; US 2010/173948, US 2010/0254960 A1, US2011/0159107, US2012/0309620, US2012/0030841, US2010/0069247, WO 2007/125984, WO 2012/086462, U.S. Pat. No. 8,318,757, US 2011/0144349, U.S. Pat. No. 8,053,452; US 2010/0137612, US 2011/152081, WO 2012/089623, WO 2012/089622, U.S. Pat. Nos. 8,119,671; 7,947,715; WO 2102/120135, WO 2012/107533, WO 2011/157748, US 2011/0245274, US 2011/0245239, US 2012/0232026, US 2012/0077765, US 2012/0035122, US 2011/0251247, WO 2011/154433, WO 2011/154434, US 2012/0238517, US 2011/0166193, WO 2011/104088, WO 2011/104087, WO 2011/104089, US 2012/015946, US 2009/0143410, WO 2007/123855, US 2011/0118212, US 2010/0137372 A1, US 2011/0086886, US 2011/0059988 A1, US 2010/0179195 A1, U.S. Pat. Nos. 7,897,630, 7,951,828, 8,383,659, 8,466,115 and 7,662,972, all of which are incorporated herein by reference in their entirety.

In another embodiment of the invention, nodulisporic acid and its derivatives (a class of known acaricidal, anthelmintic, anti-parasitic and insecticidal agents) may be added to the compositions of the invention. These compounds are used to treat or prevent infections in humans and animals and are described, for example, in U.S. Pat. Nos. 5,399,582, 5,962,499, 6,221,894 and 6,399,786, all of which are hereby incorporated by reference in their entirety. The compositions may include one or more of the known nodulisporic acid derivatives in the art, including all stereoisomers, such as those described in the patents cited above.

In another embodiment, anthelmintic compounds of the amino acetonitrile class (AAD) of compounds such as monepantel (ZOLVIX), and the like, may be added to the compositions of the invention. These compounds are described, for example, in WO 2004/024704 and U.S. Pat. No. 7,084,280 (incorporated by reference); Sager et al., Veterinary Parasitology, 2009, 159, 49-54; Kaminsky et al., Nature vol. 452, 13 Mar. 2008, 176-181.

The compositions of the invention may also include aryloazol-2-ylcyanoethylamino compounds such as those described in U.S. Pat. No. 8,088,801 to Soil et al., which is incorporated herein in its entirety, and thioamide derivatives of these compounds, as described in U.S. Pat. No. 7,964,621, which is incorporated herein by reference.

The compositions of the invention may also be combined with paraherquamide compounds and derivatives of these compounds, including derquantel (see Ostlind et al., *Research in Veterinary Science*, 1990, 48, 260-61; and Ostlind et al., *Medical and Veterinary Entomology*, 1997, 11, 407-408). The paraherquamide family of compounds is a known class of compounds that include a spirodioxepino indole core with activity against certain parasites (see *Tet. Lett.* 1981, 22, 135; *J. Antibiotics* 1990, 43, 1380, and *J. Antibiotics* 1991, 44, 492). In addition, the structurally related marcfortine family of compounds, such as marcfortines A-C, are also known and may be combined with the formulations of the invention (see *J. Chem. Soc.—Chem. Comm.* 1980, 601 and *Tet. Lett.* 1981, 22, 1977). Further references to the paraherquamide derivatives can be found, for example, in WO 91/09961, WO 92/22555, WO 97/03988, WO 01/076370, WO 09/004432, U.S. Pat. Nos. 5,703,078 and 5,750,695, all of which are hereby incorporated by reference in their entirety.

In another embodiment of the invention, the compositions may include a spinosyn active agent produced by the soil actinomycete *Saccharopolyspora spinosa* (see, for example Salgado V. L. and Sparks T. C., "*The Spinosyns: Chemistry, Biochemistry, Mode of Action, and Resistance*," in Comprehensive Molecular Insect Science, vol. 6, pp. 137-173, 2005) or a semi-synthetic spinosoid active agent. The spinosyns are typically referred to as factors or components A, B, C, D, E, F, G, H, J, K, L, M, N, O, P, Q, R, S, T, U, V, W, or Y, and any of these components, or a combination thereof, may be used in the compositions of the invention. The spinosyn compound may be a 5,6,5-tricylic ring system, fused to a 12-membered macro cyclic lactone, a neutral sugar (rhamnose), and an amino sugar (forosamine). These and other natural spinosyn compounds, including 21-butenyl spinosyn produced by *Saccharopolyspora pagona*, which may be used in the compositions of the invention, may be produced via fermentation by conventional techniques known in the art. Other spinosyn compounds that may be used in the compositions of the invention are disclosed in U.S. Pat. Nos. 5,496,931; 5,670,364; 5,591,606; 5,571,901; 5,202,242; 5,767,253; 5,840,861; 5,670,486; 5,631,155 and 6,001,981, all incorporated by reference herein in their entirety. The spinosyn compounds may include, but are not limited to, spinosyn A, spinosyn D, spinosad, spinetoram, or combinations thereof. Spinosad is a combination of spinosyn A and spinosyn D, and spinetoram is a combination of 3'-ethoxy-5,6-dihydro spinosyn J and 3'-ethoxy spinosyn L.

In addition to the other active agents mentioned above, combinations of two or more active agents may be used with the compounds of the invention in a composition to treat a desired spectrum of pests and parasites. It would be well within the skill level of the practitioner to decide which individual compound can be used in the inventive formulation to treat a particular infestation or infection of a parasite.

Methods of Treatment:

As discussed above, the compounds of formula (I) are particularly effective against parasites that harm animals and may be used to control and prevent parasitic infestations in or on animals. In one embodiment, the present invention provides a method of treating or preventing an ectoparasitic infection in or on an animal (e.g. a mammal or bird) comprising administering an effective amount of a compound of formula (I), or veterinarily acceptable salts thereof, or a composition comprising the compounds or salts, to the animal.

As described above, the compositions in which the compounds of formula (I) may be incorporated include, but are not limited to, topical compositions such as pour-on or spot-on compositions and an external device composition such as an animal ear tag or collar.

In still another embodiment of the invention, a method is provided for the control or prevention of a parasitic infestation at a locus, which comprises administering or applying an effective amount of a compound of formula (I), or veterinarily acceptable salts thereof, to the locus. With respect to animal health applications, "locus" is intended to mean a habitat, breeding ground, area, material or environment in which a parasite is developing or may develop, including in or on an animal.

Mammals which can be treated include, but are not limited to, humans, ruminant animals, cats, dogs, cattle, chickens, goats, horses, llamas, pigs, sheep and yaks. In another embodiment, the invention provides a method and use for controlling or preventing a parasitic infestation or infection in a ruminant animal. Ruminant animals include cattle, sheep, goats, deer, bison, camels and llamas. In one embodiment of the invention, the mammals treated are cattle (both beef and dairy), horses or sheep.

In one embodiment, the methods and uses of the invention are effective to control one or more insect or arachnid including those of the genera *Ctenocephalides, Rhipicephalus, Dermacentor, Ixodes, Boophilus, Amblyomma, Haemaphysalis, Hyalomma, Sarcoptes, Psoroptes, Otodectes, Chorioptes, Hypoderma, Damalinia, Linognathus, Haematopinus, Solenopotes, Trichodectes*, and *Felicola*.

In another embodiment the methods and uses of the invention are effective to control ectoparasites from the genera *Ctenocephalides, Rhipicephalus, Dermacentor, Ixodes* and/or *Boophilus*. The ectoparasites controlled include but are not limited to fleas, ticks, mites, mosquitoes, flies, lice, blowfly and combinations thereof. Specific examples include but are not limited to cat and dog fleas (*Ctenocephalides fells, Ctenocephalides* sp. and the like), ticks (*Rhipicephalus* sp., *Ixodes* sp., *Dermacentor* sp., *Amblyomma* sp. and the like), and mites (*Demodex* sp., *Sarcoptes* sp., *Otodectes* sp. and the like), lice (*Trichodectes* sp., *Cheyletiella* sp., *Linognathus* sp., and the like), mosquitoes (*Aedes* sp., *Culex* sp., *Anopheles* sp., and the like) and flies (*Haematobia* sp., *Musca* sp., *Stomoxys* sp., *Dermatobia* sp., *Cochliomyia* sp., and the like). In yet another embodiment of the invention, the ectoparasite is a flea and/or tick.

Additional examples of ectoparasites include but are not limited to the tick genus *Boophilus*, especially those of the species *microplus* (cattle tick), *decoloratus* and *annulatus*; myiases such as *Dermatobia hominis* (known as Berne in Brazil) and *Cochliomyia hominivorax* (green bottle); sheep myiases such as *Lucilia sericata, Lucilia cuprina* (known as blowfly strike in Australia, New Zealand and South Africa). Flies proper, namely those whose adult constitutes the parasite, such as *Haematobia irritans* (horn fly) and *Stomoxys calcitrans* (stable fly); lice such as *Linognathus vitulorum*, etc.; and mites such as *Sarcoptes scabiei* and *Psoroptes ovis*. The above list is not exhaustive and other ectoparasites are well known in the art to be harmful to animals and humans. These include, for example migrating dipterous larvae.

When an anthelmintic agent is added to the composition of the invention, the composition can also be used to treat against endoparasites such as those helminths selected from the group consisting of *Anoplocephala, Ancylostoma, Anecator, Ascaris, Capillaria, Cooperia, Dipylidium, Dirofilaria, Echinococcus, Enterobius, Fasciola, Haemonchus, Oesophagostumum, Ostertagia, Toxocara, Strongyloides, Toxascaris, Trichinella, Trichuris*, and *Trichostrongylus*.

In another embodiment of the invention, the compounds and compositions of the invention are suitable for controlling pests such as insects selected from the group consisting of *Blattella germanica, Heliothis virescens, Leptinotarsa decemlineata, Tetramorium caespitum* and combinations thereof.

The phytoparasitic nematodes include, for example, *Anguina* spp., *Aphelenchoides* spp., *Belonolaimus* spp., *Bursaphelenchus* spp., *Ditylenchus dipsaci, Globodera* spp., *Helicotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans* and *Xiphinema* spp.

In addition, with or without the other pesticidal agents added to the composition, the invention can also be used treat or protect animals from other pests which include but are not limited to the following pests:

(1) from the order of Isopoda, for example *Oniscus asellus, Armadillidium vulgare* and *Porcellio scaber;*

(2) from the order of Diplopoda, for example *Blaniulus guttulatus;*

(3) from the order of Chilopoda, for example *Geophilus carpophagus* and *Scutigera* spp.;

(4) from the order of Symphyla, for example *Scutigerella immaculata;*

(5) from the order of Thysanura, for example *Lepisma saccharina;*

(6) from the order of Collembola, for example *Onychiurus armatus;*

(7) from the order of Blattaria, for example *Blatta oriental's, Periplaneta americana, Leucophaea maderae* and *Blattella germanica;*

(8) from the order of Hymenoptera, for example *Diprion* spp., *Hoplocampa* spp., *Lasius* spp., *Monomorium pharaonis* and *Vespa* spp.;

(9) from the order of Siphonaptera, for example *Xenopsylla cheopis* and *Ceratophyllus* spp.;

(10) from the order of Anoplura (Phthiraptera), for example, *Damalinia* spp., *Haematopinus* spp., *Linognathus* spp., *Pediculus* spp., *Trichodectes* spp.;

(11) from the class of Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp.,

*Scorpio maurus, Steneotarsonemus* spp., *Tarsonemus* spp., *Tetranychus* spp., *Vasates lycopersici*;

(12) from the class of Bivalvia, for example, *Dreissena* spp.;

(13) from the order of Coleoptera, for example, *Acanthoscelides obtectus, Adoretus* spp., *Agelastica alni, Agriotes* spp., *Amphimallon solstitial's, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceutorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Olyctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.;

(14) from the order of Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.;

(15) from the class of Gastropoda, for example, *Arion* spp., *Biomphalaria* spp., *Bulinus* spp., *Deroceras* spp., *Galba* spp., *Lymnaea* spp., *Oncomelania* spp., *Succinea* spp.;

(16) from the class of helminths, for example, *Ancylostoma duodenale, Ancylostoma ceylanicum, Ancylostoma braziliense, Ancylostoma* spp., *Ascaris lumbricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichiura, Wuchereriabancrofti*;

(17) from the order of Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, P seudacysta persea, Rhodnius* spp., *Sahibergella singularis, Scotinophora* spp., *Stephanitis nashi, Tibraca* spp., *Triatoma* spp.;

(18) from the order of Homoptera, for example, *Acyrthosiphon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Dorsalis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis elysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifoliae*;

(19) from the order of Isoptera, for example, *Reticulitermes* spp., *Odontotermes* spp.;

(20) from the order of Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Cheimatobia brumata, Chilo* spp., *Choristoneura fumiferana, Clysia ambiguella, Cnaphalocrocis* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrixviridana, Trichoplusia* spp.;

(21) from the order of Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria*;

(22) from the order of Thysanoptera, for example, *Baliothrips biformis, Enneothrips flavens, Frankliniella* spp., *Heliothnps* spp., *Hercinothrips femoralis, Kakothrips* spp., *Rhipiphorothrips cruentatus, Scirtothrips* spp., *Taeniothrips cardamoni, Thrips* spp.;

(23) from the class of Protozoa, for example, *Eimeria* spp.

In each aspect of the invention, the compounds and compositions of the invention can be applied against a single parasite or combinations of parasites. In particular, when the compounds of formula (I) are combined with other active agents that are active against internal parasites (endoparasites), the methods and uses of the invention will be effective at controlling or preventing both ectoparasitic infestations and endoparasitic infestations.

In one embodiment, the invention provides a use or method for controlling or preventing an ectoparasitic infestation in an animal comprising administering to the animal in need an effective amount of the aryl alkyl malononitrile compound of formula (I) described above, or a salt thereof, or a composition comprising an effective amount of the compound. In another embodiment, the invention provides a use or method for controlling or preventing a parasitic infestation in an animal by parasitic flies, lice, mites or ticks. It has been found that the compounds of formula (I), or a salt thereof, and compositions comprising the compounds are particularly effective against parasitic flies including *Haematobia irritans* (horn fly) and *Stomoxys calcitrans* (stable fly). In some embodiments, the compounds and compositions of the invention have been found to be very effective against parasitic flies, including resistant strains of the flies.

In another embodiment of the invention, a use or a method for controlling or preventing a parasitic infestation of *Haematobia irritans* (horn fly), lice, mites or ticks in ruminant animals is provided, which method comprises administering an effective amount of a compound of formula (I), or a veterinarily-acceptable salt thereof, or a composition comprising the compound of formula (I) or salt, to the animal.

In another embodiment of the invention, a use or a method for controlling or preventing a parasitic infestation of *Haematobia irritans* (horn fly), lice, mites or ticks in cattle is provided, which method comprises administering an effective amount of a compound of formula (I), or a veterinarily-acceptable salt thereof, or a composition comprising the compound of formula (I) or salt, to the cattle.

In another embodiment, the invention provides a use or a method for controlling or preventing a parasitic infestation of *Haematobia irritans* (horn fly), lice, mites or ticks in horses or ponies comprising administering an effective amount of a compound of formula (I), or a veterinarily-acceptable salt thereof, or a composition comprising the compound of formula (I) or salt, to the horses or ponies.

In another embodiment, the invention provides a use or a method for controlling or preventing a parasitic infestation of *Haematobia irritans* (horn fly), lice, mites or ticks in sheep comprising administering an effective amount of a compound of formula (I), or a veterinarily-acceptable salt thereof, or a composition comprising the compound of formula (I) or salt, to the sheep.

In another embodiment of the invention, a use or a method for controlling or preventing a parasitic infestation of *Stomoxys calcitrans* (stable fly), lice, mites or ticks in a ruminant animal is provided, which method comprises administering an effective amount of a compound of formula (I), or a veterinarily-acceptable salt thereof, or a composition comprising the compound of formula (I) or salt, to the animal.

In another embodiment of the invention, a use or a method for controlling or preventing a parasitic infestation of *Stomoxys calcitrans* (stable fly), lice, mites or ticks in cattle is provided, which method comprises administering an effective amount of a compound of formula (I), or a veterinarily-acceptable salt thereof, or a composition comprising the compound of formula (I) or salt, to the cattle.

In another embodiment, the invention provides a use or a method for controlling or preventing a parasitic infestation of *Stomoxys calcitrans* (stable fly), lice, mites or ticks in horses or ponies comprising administering an effective amount of a compound of formula (I), or a veterinarily-acceptable salt thereof, or a composition comprising the compound of formula (I) or salt, to the horses or ponies.

In another embodiment, the invention provides a use or a method for controlling or preventing a parasitic infestation of *Stomoxys calcitrans* (stable fly), lice, mites or ticks in sheep comprising administering to the sheep an effective amount of a compound of formula (I), or a veterinarily-acceptable salt thereof, or a composition comprising the compound of formula (I) or salt.

In another embodiment, the invention provides a use or a method for controlling or preventing a parasitic infestation of *Stomoxys calcitrans* (stable fly), lice, mites or ticks in a ruminant animal comprising administering to the animal an effective amount of at least one compound of formulae (Ia-1), (Ia-2) or (Ia-3) wherein $R^2$ and $R^4$ are H, Q as defined for formula (I) and variables p, $R^1$, $R^3$ and $R^5$ as described in Table A.

In another embodiment, the invention provides a use or a method for controlling or preventing a parasitic infestation of *Stomoxys calcitrans* (stable fly), lice, mites or ticks in cattle, sheep or horses comprising administering to the cattle, sheep or horses an effective amount of at least one compound of formulae (Ia-1), (Ia-2) or (Ia-3) wherein $R^2$ and $R^4$ are H, Q as defined for formula (I) and variables p, $R^1$, $R^3$ and $R^5$ as described in Table A.

In another embodiment, the invention provides a use or a method for controlling or preventing a parasitic infestation of *Stomoxys calcitrans* (stable fly), lice, mites or ticks in a ruminant animal comprising administering to the animal an effective amount of at least one compound of formulae (Ib-1), (Ib-2) or (Ib-3), (Ib-4), (Ib-5), (Ib-6), (Ib-7), (Ib-8), (Ib-9), (Ib-10), (Ib-11) or (Ib-12) wherein Q as defined for formula (I), $R^2$ and $R^4$ are H, and variables p, $R^1$, $R^3$ and $R^5$ as described in Table B.

In another embodiment, the invention provides a use or a method for controlling or preventing a parasitic infestation of *Stomoxys calcitrans* (stable fly), lice, mites or ticks in cattle, sheep or horses comprising administering to the cattle, sheep or horses an effective amount of at least one compound of formulae (Ib-1), (Ib-2) or (Ib-3), (Ib-4), (Ib-5), (Ib-6), (Ib-7), (Ib-8), (Ib-9), (Ib-10), (Ib-11) or (Ib-12) wherein Q as defined for formula (I), $R^2$ and $R^4$ are H, and variables p, $R^1$, $R^3$ and $R^5$ as described in Table B.

In yet another embodiment, the invention provides a use or a method for controlling or preventing a parasitic infestation of *Stomoxys calcitrans* (stable fly), lice, mites or ticks in a ruminant animal comprising administering to the animal an effective amount of at least one compound of formulae (Ic-1), (Ic-2) or (Ic-3), (Ic-4), (Ic-5), (Ic-6), (Ic-7), (Ic-8) or (Ic-9) wherein Q as defined for formula (I), $R^2$ and $R^4$ are H, and variables p, $R^1$, $R^3$ and $R^{5a}$ and $R^{5b}$ as described in Table C.

In yet another embodiment, the invention provides a use or a method for controlling or preventing a parasitic infestation of *Stomoxys calcitrans* (stable fly), lice, mites or ticks in cattle, sheep or horses comprising administering to the cattle, sheep or horses an effective amount of at least one compound of formulae (Ic-1), (Ic-2) or (Ic-3), (Ic-4), (Ic-5), (Ic-6), (Ic-7), (Ic-8) or (Ic-9) wherein Q as defined for formula (I), $R^2$ and $R^4$ are H, and variables p, $R^1$, $R^3$ and $R^{5a}$ and $R^{5b}$ as described in Table C.

In another embodiment, the invention provides a use or a method for controlling or preventing a parasitic infestation of *Haematobia irritans* (horn fly), lice, mites or ticks in a ruminant animal comprising administering to the animal an effective amount of at least one compound of formulae (Ia-1), (Ia-2) or (Ia-3) wherein $R^2$ and $R^4$ are H, Q as defined for formula (I) and variables p, $R^1$, $R^3$ and $R^5$ as described in Table A.

In another embodiment, the invention provides a use or a method for controlling or preventing a parasitic infestation of *Haematobia irritans* (horn fly), lice, mites or ticks in cattle, sheep or horses comprising administering to the cattle, sheep or horses an effective amount of at least one compound of formulae (Ia-1), (Ia-2) or (Ia-3) wherein $R^2$ and $R^4$ are H, Q as defined for formula (I) and variables p, $R^1$, $R^3$ and $R^5$ as described in Table A.

In another embodiment, the invention provides a use or a method for controlling or preventing a parasitic infestation of *Haematobia irritans* (horn fly), lice, mites or ticks in a ruminant animal comprising administering to the animal an effective amount of at least one compound of formulae (Ib-1), (Ib-2) or (Ib-3), (Ib-4), (Ib-5), (Ib-6), (Ib-7), (Ib-8), (Ib-9), (Ib-10), (Ib-11) or (Ib-12) wherein Q as defined for formula (I), $R^2$ and $R^4$ are H, and variables p, $R^1$, $R^3$ and $R^5$ as described in Table B.

In another embodiment, the invention provides a use or a method for controlling or preventing a parasitic infestation of *Haematobia irritans* (horn fly), lice, mites or ticks in cattle, sheep or horses comprising administering to the cattle, sheep or horses an effective amount of at least one compound of formulae (Ib-1), (Ib-2) or (Ib-3), (Ib-4), (Ib-5), (Ib-6), (Ib-7), (Ib-8), (Ib-9), (Ib-10), (Ib-11) or (Ib-12) wherein Q as defined for formula (I), $R^2$ and $R^4$ are H, and variables p, $R^1$, $R^3$ and $R^5$ as described in Table B.

In yet another embodiment, the invention provides a use or a method for controlling or preventing a parasitic infestation of *Haematobia irritans* (horn fly), lice, mites or ticks in a ruminant animal comprising administering to the animal an effective amount of at least one compound of formulae (Ic-1), (Ic-2) or (Ic-3), (Ic-4), (Ic-5), (Ic-6), (Ic-7), (Ic-8) or (Ic-9) wherein Q as defined for formula (I), $R^2$ and $R^4$ are H, and variables p, $R^1$, $R^3$ and $R^{5a}$ and $R^{5b}$ as described in Table C.

In yet another embodiment, the invention provides a use or a method for controlling or preventing a parasitic infestation of *Haematobia irritans* (horn fly), lice, mites or ticks in cattle, sheep or horses comprising administering to the cattle, sheep or horses an effective amount of at least one compound of formulae (Ic-1), (Ic-2) or (Ic-3), (Ic-4), (Ic-5), (Ic-6), (Ic-7), (Ic-8) or (Ic-9) wherein Q as defined for formula (I), $R^2$ and $R^4$ are H, and variables p, $R^3$ and $R^{5a}$ and $R^{5b}$ as described in Table C.

In still another embodiment, the invention provides a use or a method for controlling or preventing a parasitic infestation of *Stomoxys calcitrans* (stable fly), lice, mites or ticks in a ruminant animal comprising administering to the animal an effective amount of at least one compound of formulae (II-1) to (II-219) as described in Table II.

In still another embodiment, the invention provides a use or a method for controlling or preventing a parasitic infestation of *Stomoxys calcitrans* (stable fly), lice, mites or ticks in cattle, sheep or horses comprising administering to the cattle, sheep or horses an effective amount of at least one compound of formulae (II-1) to (II-219) as described in Table II.

In still another embodiment, the invention provides a use or a method for controlling or preventing a parasitic infestation of *Haematobia irritans* (horn fly), lice, mites or ticks in a ruminant animal comprising administering to the animal an effective amount of at least one compound of formulae II-1 to 11-219 as described in Table II.

In still another embodiment, the invention provides a use or a method for controlling or preventing a parasitic infestation of *Haematobia irritans* (horn fly), lice, mites or ticks in cattle, sheep or horses comprising administering to the cattle, sheep or horses an effective amount of at least one compound of formulae II-1 to 11-219 as described in Table II.

In still another embodiment, the invention provides a use or a method for controlling or preventing a parasitic infestation of *Stomoxys calcitrans* (stable fly), lice, mites or ticks in a ruminant animal comprising administering to the animal an effective amount of at least one compound of formulae III-1 to III-7 as described in Table III, or of formulae IV-1 or IV-2 as described in Table IV.

In still another embodiment, the invention provides a use or a method for controlling or preventing a parasitic infestation of *Stomoxys calcitrans* (stable fly), lice, mites or ticks in cattle, sheep or horses comprising administering to the cattle, sheep or horses an effective amount of at least one compound of formulae III-1 to III-7 as described in Table III, or of formulae IV-1 or IV-2 as described in Table IV.

In still another embodiment, the invention provides a use or a method for controlling or preventing a parasitic infestation of *Haematobia irritans* (horn fly), lice, mites or ticks in a ruminant animal comprising administering to the animal an effective amount of at least one compound of formulae III-1 to III-7 as described in Table III, or of formulae IV-1 or IV-2 as described in Table IV.

In still another embodiment, the invention provides a use or a method for controlling or preventing a parasitic infestation of *Haematobia irritans* (horn fly), lice, mites or ticks in cattle, sheep or horses comprising administering to the cattle, sheep or horses an effective amount of at least one compound of formulae III-1 to III-7 as described in Table III, or of formulae IV-1 or IV-2 as described in Table IV.

In still another embodiment, the invention provides a use or a method for controlling or preventing a parasitic infestation of *Stomoxys calcitrans* (stable fly), lice, mites or ticks in a ruminant animal comprising administering to the animal an effective amount of at least one compound of formulae II-32, II-35, II-50, II-60, II-60, II-66, II-67, II-73, II-86, II-87, II-96, II-108, II-109, II-110 or II-191.

In still another embodiment, the invention provides a use or a method for controlling or preventing a parasitic infestation of *Stomoxys calcitrans* (stable fly), lice, mites or ticks in cattle, sheep or horses comprising administering to the cattle, sheep or horses an effective amount of at least one compound of formulae II-32, II-35, II-50, II-60, II-60, II-66, II-67, II-73, II-86, II-87, II-96, II-108, II-109, II-110 or II-191.

In still another embodiment, the invention provides a use or a method for controlling or preventing a parasitic infestation of *Haematobia irritans* (horn fly), lice, mites or ticks in a ruminant animal comprising administering to the animal an effective amount of at least one compound of formulae II-32, II-35, II-50, II-60, II-60, II-66, II-67, II-73, II-86, II-87, II-96, II-108, II-109, II-110 or II-191.

In still another embodiment, the invention provides a use or a method for controlling or preventing a parasitic infestation of *Haematobia irritans* (horn fly), lice, mites or ticks in cattle, sheep or horses comprising administering to the cattle, sheep or horses an effective amount of at least one compound of formulae II-32, II-35, II-50, II-60, II-60, II-66, II-67, II-73, II-86, II-87, II-96, II-108, II-109, II-110 or II-191.

In still another embodiment, the invention provides a use or a method for controlling or preventing a parasitic infestation of *Stomoxys calcitrans* (stable fly), lice, mites or ticks in cattle comprising administering to the cattle topically an effective amount of at least one compound of formulae II-32, II-35, II-50, II-60, II-60, II-66, II-67, II-73, II-86, II-87, II-96, II-108, II-109, II-110 or II-191.

In still another embodiment, the invention provides a use or a method for controlling or preventing a parasitic infestation of *Haematobia irritans* (horn fly), lice, mites or ticks in cattle comprising administering to the cattle topically an effective amount of at least one compound of formulae II-32, II-35, II-50, II-60, II-60, II-66, II-67, II-73, II-86, II-87, II-96, II-108, II-109, II-110 or II-191.

In still another embodiment, the invention provides a use or a method for controlling or preventing a parasitic infestation of *Stomoxys calcitrans* (stable fly), lice, mites or ticks in cattle comprising administering to the cattle topically in the form of a pour-on composition an effective amount of at least one compound of formulae II-32, II-35, II-50, II-60, II-60, II-66, 11-67, II-73, II-86, II-87, II-96, II-108, II-109, II-110 or II-191.

In still another embodiment, the invention provides a use or a method for controlling or preventing a parasitic infestation of *Haematobia irritans* (horn fly), lice, mites or ticks in cattle comprising administering to the cattle topically in the form of a pour-on composition an effective amount of at least one compound of formulae II-32, II-35, II-50, II-60, II-60, II-66, II-67, II-73, II-86, II-87, II-96, II-108, II-109, II-110 or II-191.

EXAMPLES

The following examples are provided to illustrate certain embodiments of the invention and are not to be construed in any way as limiting the scope of the invention.

A. Preparation Examples

With appropriate modification of the starting materials, the procedure given in the synthesis example below was used to obtain further compounds II, III and IV. The compounds obtained in this manner are listed in the table that follows, together with physical data.

The products shown below were characterized by melting point determination, by NMR spectroscopy or by the masses ([m/z]) or retention time (RT; [min.]) determined by GC MS spectrometry. [GC MS=gas chromatography-coupled mass spectrometry]

Instrument settings and chromatographic conditions:
Machine: Agilent 6890N/5975 B/MSD
Carrier gas: Helium
Column: Varian/50 m VF-1/ID=0.25 mm, FD=0.25 μm
Injection system: Agilent-Split/Splitless Injector/Modus Split 1:50
Injection: Agilent-Injector 7683 B Series/amount=1 μl
Detection: Agilent-MSD
Temperature/pressure:
Injector: 270° C.
MSD Interface: 280° C.
Source: 230° C.
MS Quad: 150° C.
Start temp.: 50° C.
Ret. Time 1: 2 min
Rate 1: 10° C./min
End temp.: 280° C.
Ret. Time 2: 45 min
Overall operating time: 70 min
Pressure (prgm): const. flow, AV: 31 cm/sec
Septum purge: 2 ml/min
Sample Preparation:
Compounds were measured as 10% dilution.

Procedure for the Preparation of 2-(4-cyanophenyl)-2-[(4-ethynylphenyl)methyl]-propanedinitrile (II-77)

2-(4-cyanophenyl)propanedinitrile (100 mg, 0.60 mmol, 1.0 equiv.) was dissolved in acetone (5 mL). $K_2CO_3$ (120 mg, 0.90 mmol, 1.5 equiv.) was added and the reaction mixture was stirred at room temperature for 20 min. A solution of (4-ethynylphenyl)-methyl methanesulfonate (130 mg, 0.60 mmol, 1.0 equiv.) in acetone (5 mL) was added dropwise and the resulting mixture was stirred at room temperature overnight. The reaction was then quenched by addition of water and extracted with ethyl acetate (3×). The combined organic layers were washed with $H_2O$ (2×) and with brine (1×), dried over $Na_2SO_4$, filtered and the solvent was removed under reduced pressure to yield the crude product. Subsequent purification via column chromatography ($SiO_2$, cyclohexane/ethyl acetate gradient 20/1→4/1) then yielded 120 mg (0.43 mmol, 71%) of II-77.

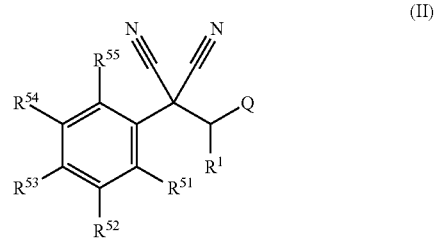

(II)

TABLE II

| Comp. | $R^{51}$ | $R^{52}$ | $R^{53}$ | $R^{54}$ | $R^{55}$ | $R^1$ | Q | physical data (GC-MS) | |
|---|---|---|---|---|---|---|---|---|---|
| | | | | | | | | RT [min] | m/z [MH]+ |
| II-1 | H | H | H | H | H | Ethoxy-carbonyl-methyl | phenyl | — | — |
| II-2 | H | H | H | H | H | H | 3,4-dichlorophenyl | 25.317 | 301.0 |
| II-3 | H | H | H | H | H | H | 4-(trifluoromethyl)phenyl | 19.719 | 300.1 |
| II-4 | H | H | H | H | H | H | 4-chlorophenyl | 23.713 | 266.0 |

TABLE II-continued

| Comp. | R$^{51}$ | R$^{52}$ | R$^{53}$ | R$^{54}$ | R$^{55}$ | R$^1$ | Q | RT [min] | m/z [MH]+ |
|---|---|---|---|---|---|---|---|---|---|
| II-5 | H | H | Cl | H | H | H | 4-chlorophenyl | 25.062 | 299.9 |
| II-6 | H | H | Cl | H | H | H | 4-(trifluoromethyl)phenyl | 23.063 | 334.1 |
| II-7 | H | H | Cl | H | H | H | 3,4-dichlorophenyl | 26.942 | 334.0 |
| II-8 | H | H | Cl | H | H | H | 4-iodophenyl | 27.898 | 392.1 |
| II-9 | H | H | H | H | H | H | 4-iodophenyl | — | — |
| II-10 | H | H | H | H | H | H | 4-(2-trimethylsilylethynyl)phenyl | 25.697 | 328.2 |
| II-11 | H | H | Cl | H | H | H | 4-ethynylphenyl | 25.775 | 290.0 |
| II-12 | H | H | H | H | H | H | 4-(trifluoromethoxy)phenyl | 21.730 | 316.0 |
| II-13 | H | Cl | Cl | H | H | H | 3,4-dichlorophenyl | 27.820 | 370.0 |
| II-14 | H | H | CF$_3$ | H | H | H | 3,4-dichlorophenyl | — | — |
| II-15 | H | Cl | Cl | H | H | H | 4-chlorophenyl | 25.944 | 335.9 |
| II-16 | H | Cl | Cl | H | H | H | 4-(trifluoromethoxy)phenyl | — | — |
| II-17 | H | Cl | Cl | H | H | H | 4-chlorophenyl | 28.719 | 425.9 |
| II-18 | H | H | CF$_3$ | H | H | H | 3,4-dichlorophenyl | 24.201 | 369.0 |
| II-19 | H | H | CF$_3$ | H | H | H | 4-(trifluoromethyl)phenyl | 20.575 | 368.2 |
| II-20 | H | H | CF$_3$ | H | H | H | 4-(trifluoromethoxy)phenyl | 20.025 | 384.0 |
| II-21 | H | H | CF$_3$ | H | H | H | 4-chlorophenyl | 22.504 | 334.0 |
| II-22 | H | H | H | H | H | H | 4-(trifluoromethylsulfanyl)phenyl | 23.202 | 331.9 |
| II-23 | H | H | I | H | H | H | 4-(trifluoromethyl)phenyl | 24.736 | 426.0 |
| II-24 | H | H | CF$_3$ | H | H | H | 4-(trifluoromethyl)phenyl | 21.435 | 384.0 |
| II-25 | H | H | CF$_3$ | H | H | H | 4-(trifluoromethylsulfanyl)phenyl | 22.272 | 414.1 |
| II-26 | H | H | CF$_3$ | H | H | H | 4-(trifluoromethoxy)phenyl | 20.187 | 400.0 |
| II-27 | H | H | Cl | H | H | H | 4-phenylphenyl | 31.067 | 342.1 |
| II-28 | H | H | Cl | H | H | H | 4-methylphenyl | 23.349 | 280.0 |
| II-29 | H | H | H | H | H | H | 4-ethynylphenyl | 24.728 | 257.1 |
| II-30 | H | H | H | H | H | H | 4-methylphenyl | 22.156 | 246.1 |
| II-31 | H | H | Me | H | H | H | 4-chlorophenyl | 24.031 | 280.1 |
| II-32 | H | H | H | H | H | H | 4-ethynylphenyl | 23.643 | 256.0 |
| II-33 | H | H | CN | H | H | H | 4-chlorophenyl | 25.984 | 291.0 |
| II-34 | H | H | ethynyl | H | H | H | 4-chlorophenyl | 25.271 | 209.0 |
| II-35 | H | H | F | H | H | H | 4-ethynylphenyl | 23.512 | 274.0 |
| II-36 | H | H | Cl | H | H | H | 4-fluorophenyl | 22.876 | 284.0 |
| II-37 | H | H | Cl | H | H | H | 4-methoxycarbonylphenyl | 26.790 | 324.0 |
| II-38 | H | H | Cl | H | H | H | 2-fluorophenyl | 22.877 | 284.1 |
| II-39 | H | H | Cl | H | H | H | 4-cyanophenyl | 26.557 | 291.1 |
| II-40 | H | H | Cl | H | H | H | 2,4-difluorophenyl | 22.357 | 302.0 |
| II-41 | H | H | Cl | H | H | H | 3-fluorophenyl | 22.845 | 284.0 |
| II-42 | H | H | Cl | H | H | H | cyclohexyl | — | — |
| II-43 | H | H | Cl | H | H | H | phenyl | 23.457 | 266.0 |
| II-44 | H | H | Cl | H | H | H | 4-vinylphenyl | 25.092 | 292.0 |
| II-45 | H | H | H | H | H | H | phenyl | 21.769 | 232.1 |
| II-46 | F | H | H | H | H | H | 4-(trifluoromethyl)phenyl | 21.342 | 318.1 |
| II-47 | H | H | F | H | H | H | 4-(trifluoromethyl)phenyl | 21.078 | 318.1 |
| II-48 | H | H | H | H | H | H | 4-bromophenyl | 24.829 | 310.0 |
| II-49 | H | H | H | H | H | Me | 4-(trifluoromethyl)phenyl | 20.908 | 313.1 |
| II-50 | H | H | F | H | H | Me | 4-(trifluoromethyl)phenyl | 20.838 | 331.0 |
| II-51 | H | H | H | H | H | H | 4-(difluoromethyl)phenyl | 24.689 | 282.1 |
| II-52 | H | H | F | H | H | H | 4-(difluoromethyl)phenyl | 22.473 | 300.1 |
| II-53 | H | H | ethynyl | H | H | H | 4-ethynylphenyl | 19.769 | 292.1 |
| II-54 | H | H | F | H | H | H | 2,4-bis(trifluoromethyl)phenyl | 19.762 | 386.1 |
| II-55 | H | H | H | H | H | H | 2,4-dimethylphenyl | 23.031 | 260.2 |
| II-56 | H | H | F | H | H | H | 2,4-dimethylphenyl | 22.179 | 278.1 |
| II-57 | H | H | F | H | H | H | 2-fluoro-4-(trifluoromethyl)phenyl | 20.671 | 336.1 |
| II-58 | H | H | H | H | H | H | 2-fluoro-4-(trifluoromethyl)phenyl | 20.567 | 318.1 |
| II-59 | H | H | F | H | H | H | 3-fluoro-4-(trifluoromethyl)phenyl | 21.365 | 336.1 |
| II-60 | H | H | H | H | H | H | 3-fluoro-4-(trifluoromethyl)phenyl | 21.420 | 318.1 |
| II-61 | H | H | F | H | H | H | 4-(trifluoromethoxy)phenyl | 20.962 | 334.0 |
| II-62 | H | H | F | H | H | H | 4-(trifluoromethylsulfanyl)phenyl | 23.016 | 350.0 |
| II-63 | H | H | F | H | H | H | 4-iodophenyl | 25.821 | 376.0 |
| II-64 | H | H | F | H | H | H | 4-bromophenyl | 24.356 | 329.0 |
| II-65 | H | H | H | H | H | H | trans-4-ethynylcyclohexyl | 22.892 | 262.1 |
| II-66 | H | F | H | H | H | H | 4-ethynylphenyl | 24.271 | 274.0 |
| II-67 | H | F | H | H | H | H | 4-(trifluoromethyl)phenyl | 20.916 | 318.1 |
| II-68 | H | H | F | H | H | ethyl | 4-(trifluoromethyl)phenyl | 19.938 | 346.1 |
| II-69 | H | H | H | H | H | ethyl | 4-(trifluoromethyl)phenyl | 20.898 | 327.0 |
| II-70 | H | H | F | H | H | methyl | 4-bromophenyl | 22.870 | 341.1 |

TABLE II-continued

| Comp. | R$^{51}$ | R$^{52}$ | R$^{53}$ | R$^{54}$ | R$^{55}$ | R$^1$ | Q | physical data (GC-MS) RT [min] | m/z [MH]+ |
|---|---|---|---|---|---|---|---|---|---|
| II-71 | H | H | H | H | H | methyl | 4-bromophenyl | NMR | |
| II-72 | H | H | F | H | H | triethylsilyl-oxymethyl | phenyl | 25.059 | 394.6 |
| II-73 | H | F | H | H | H | H | 4-(trifluoromethoxy)phenyl | 20.654 | 334.0 |
| II-74 | H | F | H | H | H | methyl | 4-(trifluoromethyl)phenyl | 20.491 | 332.0 |
| II-75 | H | F | H | H | H | methyl | 4-bromophenyl | NMR | |
| II-76 | H | H | CN | H | H | H | 4-(trifluoromethyl)phenyl | 24.176 | 325.0 |
| II-77 | H | H | CN | H | H | H | 4-ethynylphenyl | 24.485 | 281.1 |
| II-78 | F | H | H | H | H | H | 4-ethynylphenyl | 23.536 | 274.1 |
| II-79 | H | Me | H | H | H | H | 4-(trifluoromethyl)phenyl | 21.464 | 314.1 |
| II-80 | H | Me | H | H | H | H | 4-ethynylphenyl | 23.932 | 270.1 |
| II-81 | H | H | H | H | H | H | 3-fluoro-4-bromophenyl | 24.084 | 328.0 |
| II-82 | H | H | F | H | H | H | 3-fluoro-4-bromophenyl | 23.847 | 347.0 |
| II-83 | F | H | H | H | H | Me | 4-(trifluoromethyl)phenyl | 20.779 | 331.1 |
| II-84 | H | Me | H | H | H | Me | 4-(trifluoromethyl)phenyl | 21.293 | 328.1 |
| II-85 | H | F | H | F | H | H | 4-(trifluoromethyl)phenyl | 20.169 | 336.1 |
| II-86 | H | F | H | F | H | H | 4-ethynylphenyl | 22.620 | 292.0 |
| II-87 | H | F | H | F | H | Me | 4-(trifluoromethyl)phenyl | 19.740 | 350.0 |
| II-88 | H | OMe | H | H | H | H | 4-(trifluoromethyl)phenyl | 22.707 | 330.1 |
| II-89 | H | H | CN | H | H | Me | 4-(trifluoromethyl)phenyl | NMR | |
| II-90 | H | H | H | H | H | H | 4-fluorophenyl | 21.473 | 250.1 |
| II-91 | H | H | H | H | H | H | 3-(trifluoromethyl)phenyl | 21.037 | 300.1 |
| II-92 | H | CF$_3$ | H | H | H | H | 4-fluorophenyl | 20.824 | 318.1 |
| II-93 | H | H | H | H | H | H | 2-(trifluoromethyl)phenyl | 21.030 | 300.1 |
| II-94 | H | H | F | H | H | H | 2-(trifluoromethyl)phenyl | 20.720 | 318.1 |
| II-95 | H | H | F | H | H | H | 4-fluorophenyl | 21.186 | 267.0 |
| II-96 | H | H | F | H | H | Me | 4-ethynylphenyl | 23.153 | 288.0 |
| II-97 | H | OMe | H | H | H | H | 4-ethynylphenyl | 25.553 | 286.0 |
| II-98 | H | CN | H | H | H | H | 4-(trifluoromethyl)phenyl | 24.361 | 325.1 |
| II-99 | H | CN | H | H | H | H | 4-ethynylphenyl | NMR | |
| II-100 | H | OMe | H | H | H | Me | 4-(trifluoromethyl)phenyl | 22.556 | 344.1 |
| II-101 | H | CN | H | H | H | Me | 4-(trifluoromethyl)phenyl | 23.920 | 339.1 |
| II-102 | H | H | F | H | H | H | 2,5-dichloro-4-(trifluoromethyl)phenyl | 21.783 | 386.0 |
| II-103 | H | H | H | H | H | H | 2,5-dichloro-4-(trifluoromethyl)phenyl | 22.246 | 368.0 |
| II-104 | Cl | H | CF$_3$ | H | Cl | H | 4-ethynylphenyl | 24.236 | 392.0 |
| II-105 | Cl | H | CF$_3$ | H | Cl | H | 4-(trifluoromethyl)phenyl | 22.054 | 435.9 |
| II-106 | F | F | H | H | H | H | 4-ethynylphenyl | 21.799 | 292.1 |
| II-107 | F | F | H | H | H | H | 4-(trifluoromethyl)phenyl | 19.385 | 336.1 |
| II-108 | H | F | F | F | H | H | 4-(trifluoromethyl)phenyl | 18.340 | 353.1 |
| II-109 | H | F | F | F | H | H | 4-ethynylphenyl | 20.573 | 310.1 |
| II-110 | H | F | F | F | H | Me | 4-(trifluoromethyl)phenyl | 18.579 | 368.3 |
| II-111 | F | F | H | H | H | Me | 4-(trifluoromethyl)phenyl | 19.616 | 349.1 |
| II-112 | H | Me | H | Me | H | H | 4-ethynylphenyl | 23.295 | 284.1 |
| II-113 | H | Me | H | Me | H | H | 4-(trifluoromethyl)phenyl | 20.996 | 328.1 |
| II-114 | H | Me | H | Me | H | Me | 4-(trifluoromethyl)phenyl | 21.131 | 342.1 |
| II-115 | H | H | F | H | H | H | 2-fluorophenyl | 19.604 | 268.1 |
| II-116 | H | H | F | H | H | H | 2-chlorophenyl | 21.421 | 284.0 |
| II-117 | H | F | H | CF$_3$ | H | H | 4-(trifluoromethyl)phenyl | 17.748 | 386.1 |
| II-118 | H | F | H | CF$_3$ | H | H | 4-ethynylphenyl | 19.905 | 342.0 |
| II-119 | H | F | H | CF$_3$ | H | Me | 4-(trifluoromethyl)phenyl | NMR | |
| II-120 | H | H | H | H | H | H | 2-fluorophenyl | 20.124 | 250.1 |
| II-121 | H | H | H | H | H | H | 2-chlorophenyl | 21.902 | 266.1 |
| II-122 | H | F | H | F | H | H | 2-fluorophenyl | 18.695 | 285.1 |
| II-123 | H | F | H | F | H | H | 2-chlorophenyl | 20.510 | 302.1 |
| II-124 | H | F | H | F | H | H | 2-(trifluoromethyl)phenyl | 18.596 | 336.1 |
| II-125 | H | CF$_3$ | H | CF$_3$ | H | H | 4-(trifluoromethyl)phenyl | 16.845 | 436.0 |
| II-126 | H | CF$_3$ | H | CF$_3$ | H | H | 4-ethynylphenyl | 18.889 | 392.0 |
| II-128 | H | Cl | H | Cl | H | H | 4-(trifluoromethyl)phenyl | 22.187 | 366.9 |
| II-129 | H | H | H | H | H | Me | 2,4-difluorophenyl | 20.047 | 282.0 |
| II-130 | H | H | F | H | H | Me | 2,4-difluorophenyl | 19.561 | 299.1 |
| II-131 | H | F | H | F | H | Me | 2,4-difluorophenyl | 18.624 | 317.1 |
| II-134 | H | H | OCH2O | | H | H | 4-ethynylphenyl | 25.231 | 300.1 |
| II-135 | H | H | OCH2O | | H | H | 4-(trifluoromethyl)phenyl | 22.988 | 344.1 |
| II-136 | H | H | OCH2CH2O | | H | H | 4-(trifluoromethyl)phenyl | 24.458 | 358.1 |
| II-137 | H | H | OCH2CH2O | | H | H | 4-ethynylphenyl | 26.944 | 314.1 |
| II-138 | H | H | OCH2CH2O | | H | Me | 4-(trifluoromethyl)phenyl | 24.553 | 372.1 |
| II-139 | H | H | OCH2O | | H | Me | 4-(trifluoromethyl)phenyl | 23.113 | 358.1 |
| II-140 | H | H | C(O)OCH3 | H | H | H | 4-(trifluoromethyl)phenyl | 23.265 | 358.1 |
| II-141 | H | H | C(O)OCH3 | H | H | H | 4-ethynylphenyl | 25.485 | 314.1 |
| II-142 | H | F | F | F | H | H | 4-methoxyphenyl | 20.928 | 316.1 |
| II-143 | H | F | F | F | H | H | 4-fluorophenyl | 18.528 | 303.1 |
| II-144 | H | F | F | F | H | H | 4-chlorophenyl | 20.549 | 319.0 |

TABLE II-continued

| Comp. | R$^{51}$ | R$^{52}$ | R$^{53}$ | R$^{54}$ | R$^{55}$ | R$^1$ | Q | RT [min] | m/z [MH]+ |
|---|---|---|---|---|---|---|---|---|---|
| II-145 | H | F | F | F | H | H | 4-(trifluoromethyl-sulfanyl)phenyl | 20.306 | 385.9 |
| II-146 | H | H | F | H | H | H | 4-vinylphenyl | 21.877 | 276.1 |
| II-147 | H | F | F | F | H | H | 4-methylphenyl | 19.455 | 298.1 |
| II-148 | H | F | F | F | H | H | 4-cyanophenyl | 22.033 | 311.1 |
| II-149 | H | F | F | F | H | H | 4-bromophenyl | NMR | |
| II-150 | H | F | F | F | H | H | 4-methoxyphenyl | 18.403 | 369.1 |
| II-151 | H | F | F | F | H | H | 4-iodophenyl | 22.642 | 411.9 |
| II-152 | H | H | F | H | H | H | 4-chlorophenyl | — | — |
| II-153 | H | H | F | H | H | H | 4-(morpholine-4-carbonyl)phenyl | 30.488 | 363.2 |
| II-154 | H | H | F | H | H | H | 4-(isopropoxycarbonyl)phenyl | 24.474 | 336.1 |
| II-155 | H | H | F | H | H | H | 4-isopropylphenyl | 21.951 | 291.1 |
| II-156 | H | H | F | H | H | H | 4-ethylphenyl | 21.510 | 278.1 |
| II-157 | H | H | F | H | H | H | 4-cyclopropylphenyl | 23.197 | 290.1 |
| II-158 | H | H | F | H | H | H | 4-cyanophenyl | 23.004 | 275.1 |
| II-159 | H | H | F | H | H | H | 4-(2-pyridyl)phenyl | 27.636 | 327.1 |
| II-160 | H | H | F | H | H | H | 4-(difluoromethoxy)phenyl | 20.992 | 315.1 |
| II-161 | H | H | F | H | H | H | 4-(3-pyridyl)phenyl | 0.895* | 328.1* |
| II-162 | H | H | F | H | H | H | 4-(pyrrol-1-yl)phenyl | 27.745 | 315.1 |
| II-163 | H | H | F | H | H | H | 4-(pyrazol-1-yl)phenyl | 26.096 | 316.1 |
| II-164 | H | H | F | H | H | H | 4-(imidazol-1-yl)phenyl | 26.396 | 316.3 |
| II-165 | H | H | F | H | H | H | 4-(1,2,4-triazol-1-yl)phenyl | 1.041* | 318.1* |
| II-166 | H | H | F | H | H | H | 4-(4-pyridyl)phenyl | 0.878* | 328.1* |
| II-167 | H | H | F | H | H | H | 4-methylphenyl | 20.734 | 263.1 |
| II-168 | H | H | F | H | H | H | 4-[chloro(difluoro)-methoxy]phenyl | 21.515 | 349.1 |
| II-169 | H | H | F | H | H | H | 4-(2,2-difluoro-cyclopropoxy)phenyl | 23.144 | 342.3 |
| II-170 | H | H | F | H | H | H | 4-phenylphenyl | 26.805 | 326.1 |
| II-171 | H | H | F | H | H | H | 4-(tert-butyl)phenyl | 22.558 | 306.4 |
| II-172 | H | H | F | H | H | H | 4-(2,2,2-trifluoroethoxy)phenyl | — | — |
| II-173 | H | H | F | H | H | H | 4-phenoxyphenyl | 26.730 | 342.1 |
| II-174 | H | H | F | H | H | H | 4-(tert-butylsulfanyl)phenyl | 24.754 | 338.1 |
| II-175 | H | H | F | H | H | H | 4-(methylsulfonyl)phenyl | — | — |
| II-176 | H | H | F | H | H | H | 4-(methylsulfanyl)phenyl | 23.956 | 296.1 |
| II-177 | F | F | H | F | F | H | 4-(trifluoromethyl)phenyl | 19.007 | 372.1 |
| II-178 | H | F | F | F | H | Me | 4-bromophenyl | NMR | |
| II-179 | H | F | F | F | H | H | 3-cyanophenyl | 21.881 | 311.1 |
| II-180 | H | F | F | F | H | H | 2,4-bis(trifluoromethyl)phenyl | 17.351 | 422.1 |
| II-181 | H | F | F | F | H | H | 3,5-dimethylphenyl | NMR | |
| II-182 | H | F | F | F | H | H | 2-cyanophenyl | 21.057 | 311.1 |
| II-183 | H | F | F | F | H | H | 2-(difluoromethoxy)phenyl | 19.453 | 351.1 |
| II-184 | H | F | F | F | H | H | 3-chlorophenyl | NMR | |
| II-185 | H | F | F | F | H | H | 3-methoxyphenyl | 20.559 | 316.1 |
| II-186 | H | F | F | F | H | H | 3-(trifluoromethoxy)phenyl | 18.306 | 370.1 |
| II-187 | H | F | F | F | H | ethyl | phenyl | 19.417 | 314.3 |
| II-188 | H | F | F | F | H | Me | 3-(trifluoromethyl)phenyl | 18.412 | 368.3 |
| II-189 | H | F | F | F | F | H | 4-(trifluoromethyl)phenyl | NMR | |
| II-190 | H | H | F | F | F | H | 4-(trifluoromethyl)phenyl | 18.895 | 354.1 |
| II-191 | H | H | F | F | F | H | 4-ethynylphenyl | 21.246 | 310.1 |
| II-192 | H | F | F | F | H | Me | 4-chlorophenyl | 20.848 | 334.7 |
| II-193 | H | F | F | F | H | H | 2-chlorophenyl | 20.261 | 319.0 |
| II-194 | H | F | F | F | H | H | 2-fluorophenyl | 18.484 | 303.1 |
| II-195 | H | F | F | F | H | H | 2-methylphenyl | 19.608 | 299.1 |
| II-196 | H | H | F | H | H | H | 4-(dimethylcarbamoyl-sulfanyl)phenyl | 28.308 | 353.1 |
| II-197 | H | F | F | F | H | H | 3-fluorophenyl | 18.503 | 304.1 |
| II-198 | H | H | F | H | H | H | 4-[1,2,2,2-tetrafluoro-1-(trifluoromethyl)ethyl]phenyl | 19.287 | 418.1 |
| II-199 | H | F | F | F | H | H | 3,4-dichlorophenyl | 22.165 | 353.9 |
| II-200 | H | F | F | F | H | H | 2-bromo-5-methoxy-phenyl | 22.778 | 396.0 |
| II-201 | H | F | F | F | H | H | 2,6-dichlorophenyl | 22.139 | 353.9 |
| II-202 | H | F | F | F | H | H | 2,5-difluorophenyl | 18.265 | 322.1 |
| II-203 | H | F | F | F | H | Me | 2-(trifluoromethyl)phenyl | — | — |
| II-204 | F | F | I | F | F | H | 4-ethynylphenyl | 24.882 | 454.0 |
| II-205 | H | H | F | H | H | H | 4-(fluoromethyl)phenyl | 21.468 | 282.1 |
| II-206 | H | H | F | H | H | H | 4-(2,2,2-trifluoroethyl)phenyl | 20.717 | 332.1 |
| II-207 | H | H | F | H | H | H | 4-[2,2,2-trifluoro-1-hydroxy-1-(trifluoromethyl)ethyl]phenyl | 21.222 | 416.1 |
| II-208 | H | H | F | H | H | H | 4-(tert-butoxy)phenyl | 23.293 | 322.1 |
| II-209 | H | H | F | H | H | H | 4-(dimethoxymethyl)phenyl | 22.834 | 324.4 |
| II-210 | H | H | F | H | H | H | 4-methoxyphenyl | 22.171 | 280.1 |
| II-211 | H | H | F | H | H | H | 4-(acetamido)phenyl | 1.025* | 308.1* |

TABLE II-continued

| Comp. | R51 | R52 | R53 | R54 | R55 | R1 | Q | RT [min] | m/z [MH]+ |
|---|---|---|---|---|---|---|---|---|---|
| II-212 | H | H | F | H | H | H | 4-(isopropoxy)phenyl | 22.867 | 307.1 |
| II-213 | H | H | F | H | H | H | 4-propoxyphenyl | 23.538 | 308.1 |
| II-214 | H | H | F | H | H | H | 4-ethoxyphenyl | 22.703 | 294.1 |
| II-215 | H | H | F | H | H | ethyl | phenyl | 20.632 | 278.3 |
| II-216 | CF3 | H | H | H | H | H | 4-(trifluoromethyl)phenyl | 20.179 | 368.1 |
| II-217 | H | CF3 | H | H | H | H | 4-(trifluoromethyl)phenyl | 18.816 | 368.1 |
| II-218 | H | H | H | H | H | H | 4-nitrophenyl | 24.455 | 277.1 |
| II-219 | H | H | Cl | H | H | H | 4-nitrophenyl | 25.429 | 310.9 |

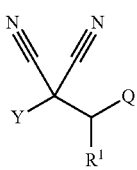

(III)

TABLE III

| Comp. | Y | R1 | Q | RT [min] | m/z [MH]+ |
|---|---|---|---|---|---|
| III-1 | 1-naphthyl | H | 4-ethynylphenyl | 21.706 | 306.1 |
| III-2 | 2-naphthyl | H | 4-ethynylphenyl | 24.077 | 306.0 |
| III-3 | 6-quinolyl | H | 4-(trifluoromethyl)phenyl | 24.691 | 351.1 |
| III-4 | 6-quinolyl | H | 4-ethynylphenyl | 27.159 | 307.1 |
| III-5 | 6-quinolyl | Me | 4-(trifluoromethyl)phenyl | 24.786 | 365.1 |
| III-6 | quinoxalin-6-yl | H | 4-(trifluoromethyl)phenyl | 24.635 | 352.1 |
| III-7 | quinoxalin-6-yl | H | 4-ethynylphenyl | 27.083 | 308.1 |

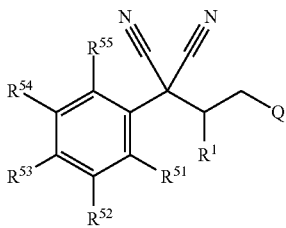

(IV)

TABLE IV

| Comp. | R51 | R52 | R53 | R54 | R55 | R1 | Q | RT [min] | m/z [MH]+ |
|---|---|---|---|---|---|---|---|---|---|
| IV-1 | H | H | H | H | H | H | 4-(trifluoromethyl)phenyl | 23.016 | 314.1 |
| IV-2 | H | H | H | H | H | H | 4-chlorophenyl | 24.705 | 280.1 |

The products II-161, II-165, II-166 and II-211 marked with "*" above were characterized by the masses ([m/z]) and retention time (RT; [min.]) determined by HPLC-MS.

HPLC-MS=high performance liquid chromatography-coupled mass spectrometry; HPLC methods:

Phenomenex Kinetex 1.7 μm XB-C18 100A; 50×2.1 mm; mobile phase: A: water+0.1% trifluoroacetic acid (TFA); B: acetonitrile+0.1% TFA; gradient: 5-100% B in 1.50 minutes; 100% B 0.20 min; flow: 0.8-1.0 ml/min in 1.50 minutes at 60° C.

MS: quadrupole electrospray ionization, 80 V (positive mode).

NMR-data for selected analogs as indicated in the table above:

II-68: $^1$H-NMR (400 MHz, CDCl$_3$): δ=0.80 (t, 3H), 2.10-2.25 (m, 2H), 3.19 (dd, 1H), 7.07 (t, 2H), 7.21 (d, 2H), 7.27-7.32 (m, 2H), 7.55 (d, 2H).

II-70: $^1$H-NMR (500 MHz, CDCl$_3$): δ=1.64 (d, 3H), 3.41 (q, 1H), 6.95 (d, 2H), 7.06-7.11 (m, 2H), 7.28-7.33 (m, 2H), 7.40 (d, 2H).

II-71: $^1$H-NMR (500 MHz, CDCl$_3$): δ=1.63 (d, 3H), 3.44 (q, 1H), 6.96 (d, 2H), 7.30-7.55 (m, 5H), 7.59-7.65 (m, 1H), 7.82 (d, 1H).

II-75: $^1$H-NMR (400 MHz, CDCl$_3$): δ=1.64 (d, 3H), 3.43 (q, 1H), 6.98 (d, 2H), 7.08-7.16 (m, 3H), 7.36-7.42 (3H).

II-89: $^1$H-NMR (500 MHz, CDCl$_3$): δ=1.71 (d, 3H), 3.54 (q, 1H), 7.22 (d, 2H), 7.48 (d, 2H), 7.56 (d, 2H), 7.72 (d, 2H).

II-99: $^1$H-NMR (400 MHz, CDCl$_3$): δ=3.15 (s, 1H), 3.48 (s, 2H), 7.08 (d, 2H), 7.45 (d, 2H), 7.59-7.68 (m, 2H), 7.79 (d, 2H).

II-105: $^1$H-NMR (500 MHz, CDCl$_3$): δ=3.75 (s, 2H), 7.48 (d, 2H), 7.67 (d, 2H), 7.72 (s, 2H).

II-119: $^1$H-NMR (500 MHz, CDCl$_3$): δ=1.74 (d, 3H), 3.52 (q, 1H), 7.22 (d, 2H), 7.31 (d, 1H), 7.42 (d, 1H), 7.57 (d, 2H).

II-149: $^1$H-NMR (400 MHz, CDCl$_3$): δ=3.41 (s, 2H), 7.03-7.06 (m, 2H), 7.14-7.17 (m, 2H), 7.47-7.53 (m, 2H).

II-178: $^1$H-NMR (400 MHz, CDCl$_3$): δ=1.66 (d, 3H), 3.40 (q, 1H), 6.98-7.03 (m, 4H), 7.44-7.48 (m, 2H).

II-181: $^1$H-NMR (400 MHz, CDCl$_3$): δ=2.29 (s, 6H), 3.35 (s, 2H), 6.74 (s, 2H), 7.02 (s, 1H), 7.13 (q, 2H).

II-184: $^1$H-NMR (400 MHz, CDCl$_3$): δ=3.41 (s, 2H), 7.06 (d, 1H), 7.14-7.17 (m, 3H), 7.32 (d, 1H), 7.42 (d, 1H).

II-189: $^1$H-NMR (400 MHz, CDCl$_3$): δ=3.67 (s, 2H), 7.44 (d, 2H), 7.57-7.73 (m, 3H).

B. Biological Examples

1. Contact Activity Against *Stomoxys calcitrans*

Compounds II-32, II-35, II-50, II-60, II-66, II-67, II-73, II-86, II-87, II-96, II-108, II-109, II-110 and II-191 were evaluated for their activity against the ectoparasite *Stomoxys calcitrans* (stable fly). Solutions of the test compound at decreasing concentrations (5 dose range) were used to treat a filter papers contained within Petri dishes and the filter papers were allowed to evaporate to dryness. A small piece of absorbent cotton moistened with 10% sucrose and ten adult stable flies were added to each dish. Dishes were capped and held at room temperature. Assessments were performed at 1 hour, 6 hours and 24 hours after addition of the flies in comparison with untreated controls. The effective concentration (EC$_{50}$) required to kill 50% of the stable flies (nmol/cm$^2$) was calculated for each compound at 1 hour, 6 hours and 24 hours after introduction of the flies. Compounds II-50, II-73, II-87, II-108, II-109 and II-110 were found to have EC$_{50}$ values of less than 10 nmol/cm$^2$ after 1 hour. All of the compounds tested were found to have EC$_{50}$ values of less than 1 nmol/cm$^2$ after 6 hours and 24 hours, and compounds II-32, II-35, II-60, II-66, II-67, II-73, II-86, II-87, II-96, II-108, II-109 and II-110 were found to have EC$_{50}$ values of less than 0.1 nmol/cm$^2$ after 24 hours.

2. Contact Activity Against *Haematobia irritans*

Compounds II-32, II-35, II-50, II-60, II-66, II-67, II-73, II-86, II-87, II-96, II-108, II-109, II-110 and II-191 were evaluated for their activity against the ectoparasite *Haematobia irritans* (horn fly). Solutions of the test compound at decreasing concentrations (5 dose range) were used to treat a filter papers contained within Petri dishes and the filter papers were allowed to evaporate to dryness. A small piece of absorbent cotton moistened with 10% sucrose and ten adult horn flies were added to each dish. Dishes were capped and held at room temperature. Assessments were performed at 1 hour, 6 hours and 24 hours after addition of the flies in comparison with untreated controls. The effective concentration (EC$_{50}$) required to kill 50% of the stable flies (nmol/cm$^2$) was calculated for each compound at 1 hour, 6 hours and 24 hours after introduction of the flies. Compounds II-32, II-50, II-60, II-66, II-67, II-73, II-86, II-87, II-96, II-108, II-109 and II-110 were found to have EC$_{50}$ values of less than 10 nmol/cm$^2$ after 1 hour. All of the compounds tested were found to have EC$_{50}$ values of less than 1 nmol/cm$^2$ after 6 hours and 24 hours; compounds II-32, II-35, II-60, II-66, II-67, II-73, II-86, II-87, II-108, II-109 and II-110 were found to have EC$_{50}$ values of less than 0.1 nmol/cm$^2$ after 6 hours; and all of the compounds tested were found to have EC$_{50}$ values of less than 0.1 at 24 hours.

3. In Vivo Efficacy Against *Haematobia irritans*

A representative compound of the invention (II-35) was evaluated for efficacy against 20 *Haematobia irritans* in cattle when applied topically. Four treatment groups and one untreated control group containing four animals each were formed. Treatment Group 1 was an untreated control and Treatment Group 5 was a positive control group treated with a pour-on product containing 5% (w/v) cypermethrin (Cypermil Pour-on). The animals in Treatment Groups 2, 3 and 4 were treated with a pour-on composition containing compound (II-35) to deliver doses of 20 mg/kg, 10 mg/kg and 5 mg/kg body weight, respectively. The pour-on formulations comprised a mixture of 20% (w/v), 10% (w/v) and 5% (w/v) of the active dissolved in a carrier comprising 50% (v/v)N-methylpyrrolidone, 5% (v/v) dimethyl isosorbide and qs with Miglyol® 840. All animals were infested with approximately 200 *Haematobia irritans* flies on Days 1, 7, 14 and 21. As the source of flies was natural and the amount of flies decreased, the infestations On Days 28 and 35 animals were with approximately 100 horn flies due to a lack of flies. Additionally, Treatment Groups 3 and 5 were not infested on Day 35, due to the lack of flies. The flies were counted and recorded five hours following infestation and on the following day (at 24 h). The counts done on Day 2 were at 48 hours after treatment.

Treatment Groups 2 (20 mg/kg) and 4 (5 mg/kg) showed efficacy above 93% until Day 13, after 5 hours post infestation and until Day 29, after 24 hours post infestation. Treatment Group 3 (10 mg/kg), showed efficacy above 93% until Day 13, after 5 hours post infestation and until Day 22, after 24 hours post infestation. In comparison, the positive control (Treatment Group 5) showed efficacy of 73% on Day 2 and below 67% on the following days. The % efficacy (% reduction) of the each treatment group compared with the untreated control group is shown in Tables 2 and 3 below and in FIG. 1.

TABLE 2

Efficacy vs. *Haematobia irritans* at 5 h

| Treatment Group | % Efficacy | | | | | |
|---|---|---|---|---|---|---|
| | Day 1 | Day 7 | Day 13 | Day 21 | Day 28 | Day 35 |
| Group 2 | 97.8 | 99.2 | 97.7 | 86.6 | 85.0 | 65.8 |
| Group 3 | 98.9 | 98.2 | 93.8 | 68.3 | 65.6 | NA |
| Group 4 | 99.5 | 98.3 | 93.2 | 80.0 | 64.1 | 51.5 |
| Group 5 | 82.0 | 54.5 | 34.8 | 27.2 | 7.7 | NA |

TABLE 3

Efficacy vs. *Haematobia irritans* at 24 h

| Treatment Group | % Efficacy | | | | | |
|---|---|---|---|---|---|---|
| | Day 2 | Day 8 | Day 14 | Day 22 | Day 29 | Day 36 |
| Group 2 | 100.0 | 98.3 | 100.0 | 97.9 | 96.9 | 85.6 |
| Group 3 | 100.0 | 100.0 | 100.0 | 93.1 | 69.2 | NA |
| Group 4 | 100.0 | 99.7 | 100.0 | 93.5 | 95.5 | 88.1 |
| Group 5 | 73.3 | 66.4 | 29.2 | 30.3 | 10.5 | NA |

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for controlling or preventing the parasitic infestation of cattle by *Stomoxvs calcitrans* or *Haematobia irritans* comprising administering a pour-on formulation comprising an effective amount of an aryl alkyl malononitrile compound of formula (I), or a salt thereof, to the animal:

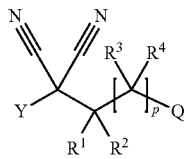

wherein
Y is phenyl unsubstituted or substituted with 1, 2, 3, 4 or 5 substituents $R^5$;
Q is phenyl unsubstituted or substituted with 1, 2, 3, 4 or 5 substituents $R^6$;
$R^1$ is hydrogen or $C_1$-$C_6$ alkyl;
$R^2$ is hydrogen;
each $R^5$ is independently halogen;
each $R^6$ is independently halogen, $C_1$-$C_6$alkyl, wherein the carbon atoms of the aforementioned $C_1$-$C_6$alkyl are unsubstituted or substituted with one or more $R^a$, or —$OCF_3$; or $R^6$ is $C_2$-$C_6$alkynyl;
each $R^a$ is independently halogen;
p is 0; and $R^3$ and $R^4$ are not present.

2. The method of claim 1, wherein:
$R^1$ is H, methyl, ethyl or isopropyl.

3. The method of claim 1, wherein $R^5$ is fluoro.

4. The method of claim 3, wherein $R^6$ is fluoro.

5. The method of claim 1, wherein
Y is phenyl substituted with 1, 2, or 3 substituents $R^5$;
Q is phenyl substituted with 1, 2, or 3 substituents $R^6$;
$R^1$ is H or methyl;
$R^2$ is H and
each $R^5$ is independently halogen.

6. The method of claim 1, wherein the compound of formula (I), or a salt thereof, is administered via an external device.

7. The method of claim 1, wherein the volume of the pour-on formulation is about 10 ml to about 100 mL.

8. The method of claim 1, wherein the concentration of the compound of formula (I) is about 5% (w/v) to about 20% (w/v).

9. The method of claim 1, wherein the pour-on formulation comprises N-methylpyrrolidone, dimethyl isosorbide or a $C_8$ to $C_{12}$ triglyceride or a $C_8$-$C_{12}$ esters of propylene glycol, or a combination thereof.

10. The method of claim 1, wherein the method is at least 70% effective against *Haematobia irritans* 24 hours after infestation for at least 22 days.

11. The method of claim 1, wherein the method is at least 90% effective against *Haematobia irritans* 24 hours after infestation for at least 22 days.

12. The method of claim 1, wherein the compound of formula (I) has the structure of formula (II):

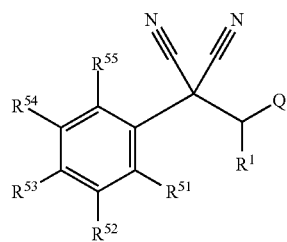

wherein:
Q is 4-ethynylphenyl;
$R^1$, $R^{51}$, $R^{52}$, $R^{54}$ and $R^{55}$ are each hydrogen; and
$R^{53}$ is fluoro.

* * * * *